United States Patent
Ichikawa et al.

(10) Patent No.: US 7,361,340 B2
(45) Date of Patent: Apr. 22, 2008

(54) ANTIBODY AGAINST TUMOR SPECIFIC ANTIGEN AS TARGET

(75) Inventors: Kimihasa Ichikawa, Tokyo (JP); Shu Takahashi, Tokyo (JP); Toshinori Agatsuma, Tokyo (JP); Keisuke Fukuchi, Tokyo (JP); Takehiro Hirai, Tokyo (JP)

(73) Assignee: Sankyo Co., Ltd., Tokyo (JP)

( * ) Notice: Subject to any disclaimer, the term of this patent is extended or adjusted under 35 U.S.C. 154(b) by 0 days.

(21) Appl. No.: 11/223,812

(22) Filed: Sep. 9, 2005

(65) Prior Publication Data

US 2006/0127405 A1 Jun. 15, 2006

Related U.S. Application Data

(63) Continuation of application No. PCT/JP2004/003048, filed on Mar. 9, 2004.

(30) Foreign Application Priority Data

Mar. 10, 2003 (JP) .............................. 2003-063648

(51) Int. Cl.
*A61K 39/395* (2006.01)
*C07K 16/30* (2006.01)

(52) U.S. Cl. ............................... 424/130.1; 530/388.1; 530/388.8

(58) Field of Classification Search ...................... None
See application file for complete search history.

(56) References Cited

U.S. PATENT DOCUMENTS

| | | | | |
|---|---|---|---|---|
| 5,728,821 A | | 3/1998 | Yelton et al. | 536/23.53 |
| 5,792,456 A | | 8/1998 | Yelton et al. | 424/133.1 |
| 2003/0124579 A1 | | 7/2003 | Mack et al. | 435/6 |
| 2003/0228319 A1 | * | 12/2003 | Frantz et al. | 424/155.1 |
| 2004/0151665 A1 | * | 8/2004 | Young et al. | 424/1.49 |
| 2005/0170368 A1 | * | 8/2005 | Ashkenazi et al. | 435/6 |

FOREIGN PATENT DOCUMENTS

WO  WO 01/09187 A2  2/2001

OTHER PUBLICATIONS

Fu et al (EMBO Journal, 1996, vol. 15, pp. 4392-4401).*
Brennan et al (Journal of Autoimmunity, 1989, vol. 2 suppl., pp. 177-186).*
Zimmer (Cell Motility and the Cytoskeleton, 1991, vol. 20, pp. 325-337).*
Eriksson et al. (Diabetologia, 1992, vol. 35, pp. 143-147).*
Dillman (Annals of Internal Medicine, 1989 111:592-603).*
Gura (1997, Science 278:1041-1042).*
Tockman et al (Cancer Res., 1992, 52:2711s-2718s).*
Wistow et al., Expressed sequence tag analysis of human RPE/choroid for the NEIBank Project: Over 6000 non-redundant transcripts, novel genes and splice variants; *Molecular Vision 2002*(8): pp. 205-220, Jun. 15, 2002.
Mammalian Gene Collection Program Team (contributed by Francis S. Collins), "Generation and initial analysis of more than 15,000 full-length human and mouse cDNA sequences," *PNAS 99*(26): pp. 16899-16903, Dec. 24, 2002.
Longo et al., "Regulatory role of tetraspanin CD9 in tumor-endothelial celll interaction during transendothelial invasion of melanoma cells," *BLOOD 98*(13): pp. 3717-3726, Dec. 15, 2001.
Azorsa et al., "A general approach to the generation of monoclonal antibodies against members of the tetraspanin superfamily using recombinant GST fusion proteins," *Journal of Immunological Methods 229*: pp. 35-48, 1999.

* cited by examiner

*Primary Examiner*—Karen A. Canella
*Assistant Examiner*—Catherine Joyce
(74) *Attorney, Agent, or Firm*—Dorsey & Whitney LLP

(57) ABSTRACT

The present invention relates to a method of detecting cancer by use of an oncogene, a method of screening for an active compound useful to treat and/or prevent cancer, and a pharmaceutical composition for treatment and/or prevention of cancer. More specifically, the present invention provides a method of detecting cancer based on the expression of the human oculospanin gene as a marker and a pharmaceutical composition containing an antibody capable of specifically recognizing human oculospanin and having cytotoxic activity against cancer cells.

2 Claims, 5 Drawing Sheets

**: $p<0.001$

**: $p<0.001$

**: $p<0.001$

**: $p<0.001$

*: $p<0.01$

Lane 1 : pDEST40 NM_031945 transformed cells
Lane 2 : Control untransformed cells ial Application No. PCT/JP2004/003048, filed Mar. 9, 2004, which claims the benefit under 35 U.S.C. 365(c) of Japanese Application No. 2003-063648, filed Mar. 10, 2003.

SEQUENCE LISTING

```
<160> NUMBER OF SEQ ID NOS: 6

<210> SEQ ID NO 1
<211> LENGTH: 1065
<212> TYPE: DNA
<213> ORGANISM: Homo sapiens
<220> FEATURE:
<221> NAME/KEY: exon
<222> LOCATION: (1)..(1065)

<400> SEQUENCE: 1 atg gag gag ggg gag agg agc ccc tta ctg tcc cag gaa act gca ggc      48
Met Glu Glu Gly Glu Arg Ser Pro Leu Leu Ser Gln Glu Thr Ala Gly
1               5                   10                  15
```

-continued

| | |
|---|---|
| cag aag ccc ctc tct gtg cac agg cca ccc acc tca ggc tgc cta ggt<br>Gln Lys Pro Leu Ser Val His Arg Pro Pro Thr Ser Gly Cys Leu Gly<br>20 25 30 | 96 |
| cca gtg ccc agg gag gac cag gcg gag gcc tgg ggc tgc agc tgc tgt<br>Pro Val Pro Arg Glu Asp Gln Ala Glu Ala Trp Gly Cys Ser Cys Cys<br>35 40 45 | 144 |
| ccc ccg gag acc aag cac cag gcc ttg agt ggc act ccc aag aaa gga<br>Pro Pro Glu Thr Lys His Gln Ala Leu Ser Gly Thr Pro Lys Lys Gly<br>50 55 60 | 192 |
| cca gcc cct tcc ctc tcc cca ggg agc agc tgc gtc aag tat ctg atc<br>Pro Ala Pro Ser Leu Ser Pro Gly Ser Ser Cys Val Lys Tyr Leu Ile<br>65 70 75 80 | 240 |
| ttc ctc tcc aac ttc ccc ttc tcc ctg ctg ggg ctg ctg gcc ctg gcc<br>Phe Leu Ser Asn Phe Pro Phe Ser Leu Leu Gly Leu Leu Ala Leu Ala<br>85 90 95 | 288 |
| atc ggg ctc tgg ggc ctg gct gtc aag ggg tct ctg gga agt gat ctg<br>Ile Gly Leu Trp Gly Leu Ala Val Lys Gly Ser Leu Gly Ser Asp Leu<br>100 105 110 | 336 |
| ggg ggg ccc ctg ccc aca gac ccc atg ctg ggg ctg gca ctg gga ggg<br>Gly Gly Pro Leu Pro Thr Asp Pro Met Leu Gly Leu Ala Leu Gly Gly<br>115 120 125 | 384 |
| ctg gtg gtc agc gca gcg agc ctg gct ggc tgc ctg ggc gcc ctc tgc<br>Leu Val Val Ser Ala Ala Ser Leu Ala Gly Cys Leu Gly Ala Leu Cys<br>130 135 140 | 432 |
| gag aac acc tgc ctg tta cgt ggc ttc tcc ggg ggc atc ctt gcc ttc<br>Glu Asn Thr Cys Leu Leu Arg Gly Phe Ser Gly Gly Ile Leu Ala Phe<br>145 150 155 160 | 480 |
| ctg gtg ctt gag gcc gtg gcg ggg gcc ctg gtg gtg gcc ctc tgg ggc<br>Leu Val Leu Glu Ala Val Ala Gly Ala Leu Val Val Ala Leu Trp Gly<br>165 170 175 | 528 |
| ccg ctg caa gac agc ctg gag cac acc ctg cgt gtg gcc atc gcc cac<br>Pro Leu Gln Asp Ser Leu Glu His Thr Leu Arg Val Ala Ile Ala His<br>180 185 190 | 576 |
| tac cag gac gac cca gac ctg cgc ttc ctc ctc gac caa gtc cag ctc<br>Tyr Gln Asp Asp Pro Asp Leu Arg Phe Leu Leu Asp Gln Val Gln Leu<br>195 200 205 | 624 |
| ggg ctg agg tgc tgc gga gct gcc tcc tac cag gac tgg cag cag aac<br>Gly Leu Arg Cys Cys Gly Ala Ala Ser Tyr Gln Asp Trp Gln Gln Asn<br>210 215 220 | 672 |
| ctg tac ttt aac tgc agc tcc ccc ggg gtg cag gcc tgc agc ctt ccc<br>Leu Tyr Phe Asn Cys Ser Ser Pro Gly Val Gln Ala Cys Ser Leu Pro<br>225 230 235 240 | 720 |
| gcc tcc tgc tgc atc gac ccc cgc gaa gat gga gcc tct gtc aac gac<br>Ala Ser Cys Cys Ile Asp Pro Arg Glu Asp Gly Ala Ser Val Asn Asp<br>245 250 255 | 768 |
| cag tgc ggc ttc ggg gtc ctg cgc ctg gat gcg gac gca gct cag aga<br>Gln Cys Gly Phe Gly Val Leu Arg Leu Asp Ala Asp Ala Ala Gln Arg<br>260 265 270 | 816 |
| gtg gtg tac ctg gag ggc tgc ggc ccg ccg ctc cgg cgg tgg ctg cgc<br>Val Val Tyr Leu Glu Gly Cys Gly Pro Pro Leu Arg Arg Trp Leu Arg<br>275 280 285 | 864 |
| gcg aac ctg gct gcc tcg ggc ggc tac gca atc gcg gtg gtg ctg ctg<br>Ala Asn Leu Ala Ala Ser Gly Gly Tyr Ala Ile Ala Val Val Leu Leu<br>290 295 300 | 912 |
| cag ggc gcg gag ctc ctg ctg gcc gcc cgg cta ctc ggg gcc ctc gct<br>Gln Gly Ala Glu Leu Leu Leu Ala Ala Arg Leu Leu Gly Ala Leu Ala<br>305 310 315 320 | 960 |
| gcc cgc agt ggg gcg gcg tac ggc ccc gga gcg cgc ggg gag gac cgc<br>Ala Arg Ser Gly Ala Ala Tyr Gly Pro Gly Ala Arg Gly Glu Asp Arg | 1008 |

```
                    325                 330                 335
gct ggc ccc cag agc ccc agc ccc ggc gcc ccg ccc gct gcc aaa ccc     1056
Ala Gly Pro Gln Ser Pro Ser Pro Gly Ala Pro Pro Ala Ala Lys Pro
            340                 345                 350 gcc cgg ggc                                                         1065
Ala Arg Gly
        355

<210> SEQ ID NO 2
<211> LENGTH: 355
<212> TYPE: PRT
<213> ORGANISM: Homo sapiens

<400> SEQUENCE: 2

Met Glu Glu Gly Glu Arg Ser Pro Leu Leu Ser Gln Glu Thr Ala Gly
1               5                   10                  15

Gln Lys Pro Leu Ser Val His Arg Pro Thr Ser Gly Cys Leu Gly
            20                  25                  30

Pro Val Pro Arg Glu Asp Gln Ala Glu Ala Trp Gly Cys Ser Cys Cys
        35                  40                  45

Pro Pro Glu Thr Lys His Gln Ala Leu Ser Gly Thr Pro Lys Lys Gly
    50                  55                  60

Pro Ala Pro Ser Leu Ser Pro Gly Ser Ser Cys Val Lys Tyr Leu Ile
65                  70                  75                  80

Phe Leu Ser Asn Phe Pro Phe Ser Leu Leu Gly Leu Ala Leu Ala
                85                  90                  95

Ile Gly Leu Trp Gly Leu Ala Val Lys Gly Ser Leu Gly Ser Asp Leu
            100                 105                 110

Gly Gly Pro Leu Pro Thr Asp Pro Met Leu Gly Leu Ala Leu Gly Gly
        115                 120                 125

Leu Val Val Ser Ala Ala Ser Leu Ala Gly Cys Leu Gly Ala Leu Cys
    130                 135                 140

Glu Asn Thr Cys Leu Leu Arg Gly Phe Ser Gly Gly Ile Leu Ala Phe
145                 150                 155                 160

Leu Val Leu Glu Ala Val Ala Gly Ala Leu Val Val Ala Leu Trp Gly
                165                 170                 175

Pro Leu Gln Asp Ser Leu Glu His Thr Leu Arg Val Ala Ile Ala His
            180                 185                 190

Tyr Gln Asp Asp Pro Asp Leu Arg Phe Leu Leu Asp Gln Val Gln Leu
        195                 200                 205

Gly Leu Arg Cys Cys Gly Ala Ala Ser Tyr Gln Asp Trp Gln Gln Asn
    210                 215                 220

Leu Tyr Phe Asn Cys Ser Ser Pro Gly Val Gln Ala Cys Ser Leu Pro
225                 230                 235                 240

Ala Ser Cys Cys Ile Asp Pro Arg Glu Asp Gly Ala Ser Val Asn Asp
                245                 250                 255

Gln Cys Gly Phe Gly Val Leu Arg Leu Asp Ala Asp Ala Ala Gln Arg
            260                 265                 270

Val Val Tyr Leu Glu Gly Cys Gly Pro Pro Leu Arg Arg Trp Leu Arg
        275                 280                 285

Ala Asn Leu Ala Ala Ser Gly Gly Tyr Ala Ile Ala Val Val Leu Leu
    290                 295                 300

Gln Gly Ala Glu Leu Leu Leu Ala Ala Arg Leu Leu Gly Ala Leu Ala
305                 310                 315                 320

Ala Arg Ser Gly Ala Ala Tyr Gly Pro Gly Ala Arg Gly Glu Asp Arg
```

-continued

```
                    325                 330                 335
Ala Gly Pro Gln Ser Pro Ser Pro Gly Ala Pro Pro Ala Ala Lys Pro
            340                 345                 350

Ala Arg Gly
        355
```

<210> SEQ ID NO 3
<211> LENGTH: 1601
<212> TYPE: DNA
<213> ORGANISM: Homo sapiens
<220> FEATURE:
<221> NAME/KEY: exon
<222> LOCATION: (65)..(1129)

<400> SEQUENCE: 3

```
cacagaggag ccagcgaacc tctcccggcg cctgttctgg gggctttctg ttccagcgtc        60 aagg atg gag gag ggg gag agg agc ccc tta ctg tcc cag gaa act gca       109
     Met Glu Glu Gly Glu Arg Ser Pro Leu Leu Ser Gln Glu Thr Ala
     1               5                   10                  15 ggc cag aag ccc ctc tct gtg cac agg cca ccc acc tca ggc tgc cta       157
Gly Gln Lys Pro Leu Ser Val His Arg Pro Pro Thr Ser Gly Cys Leu
                20                  25                  30 ggt cca gtg ccc agg gag gac cag gcg gag gcc tgg ggc tgc agc tgc       205
Gly Pro Val Pro Arg Glu Asp Gln Ala Glu Ala Trp Gly Cys Ser Cys
            35                  40                  45 tgt ccc ccg gag acc aag cac cag gcc ttg agt ggc act ccc aag aaa       253
Cys Pro Pro Glu Thr Lys His Gln Ala Leu Ser Gly Thr Pro Lys Lys
        50                  55                  60 gga cca gcc cct tcc ctc tcc cca ggg agc agc tgc gtc aag tat ctg       301
Gly Pro Ala Pro Ser Leu Ser Pro Gly Ser Ser Cys Val Lys Tyr Leu
    65                  70                  75 atc ttc ctc tcc aac ttc ccc ttc tcc ctg ctg ggg ctg ctg gcc ctg       349
Ile Phe Leu Ser Asn Phe Pro Phe Ser Leu Leu Gly Leu Leu Ala Leu
80                  85                  90                  95 gcc atc ggg ctc tgg ggc ctg gct gtc aag ggg tct ctg gga agt gat       397
Ala Ile Gly Leu Trp Gly Leu Ala Val Lys Gly Ser Leu Gly Ser Asp
                100                 105                 110 ctg ggg ggg ccc ctg ccc aca gac ccc atg ctg ggg ctg gca ctg gga       445
Leu Gly Gly Pro Leu Pro Thr Asp Pro Met Leu Gly Leu Ala Leu Gly
            115                 120                 125 ggg ctg gtg gtc agc gca gcg agc ctg gct ggc tgc ctg ggc gcc ctc       493
Gly Leu Val Val Ser Ala Ala Ser Leu Ala Gly Cys Leu Gly Ala Leu
        130                 135                 140 tgc gag aac acc tgc ctg tta cgt ggc ttc tcc ggg ggc atc ctt gcc       541
Cys Glu Asn Thr Cys Leu Leu Arg Gly Phe Ser Gly Gly Ile Leu Ala
    145                 150                 155 ttc ctg gtg ctt gag gcc gtg gcg ggg gcc ctg gtg gtg gcc ctc tgg       589
Phe Leu Val Leu Glu Ala Val Ala Gly Ala Leu Val Val Ala Leu Trp
160                 165                 170                 175 ggc ccg ctg caa gac agc ctg gag cac acc ctg cgt gtg gcc atc gcc       637
Gly Pro Leu Gln Asp Ser Leu Glu His Thr Leu Arg Val Ala Ile Ala
                180                 185                 190 cac tac cag gac gac cca gac ctg cgc ttc ctc ctc gac caa gtc cag       685
His Tyr Gln Asp Asp Pro Asp Leu Arg Phe Leu Leu Asp Gln Val Gln
            195                 200                 205 ctc ggg ctg agg tgc tgc gga gct gcc tcc tac cag gac tgg cag cag       733
Leu Gly Leu Arg Cys Cys Gly Ala Ala Ser Tyr Gln Asp Trp Gln Gln
        210                 215                 220 aac ctg tac ttt aac tgc agc tcc ccc ggg gtg cag gcc tgc agc ctt       781
Asn Leu Tyr Phe Asn Cys Ser Ser Pro Gly Val Gln Ala Cys Ser Leu
```

```
              225                 230                 235
ccc gcc tcc tgc tgc atc gac ccc cgc gaa gat gga gcc tct gtc aac      829
Pro Ala Ser Cys Cys Ile Asp Pro Arg Glu Asp Gly Ala Ser Val Asn
240                 245                 250                 255 gac cag tgc ggc ttc ggg gtc ctg cgc ctg gat gcg gac gca gct cag      877
Asp Gln Cys Gly Phe Gly Val Leu Arg Leu Asp Ala Asp Ala Ala Gln
                260                 265                 270 aga gtg gtg tac ctg gag ggc tgc ggc ccg ccg ctc cgg cgg tgg ctg      925
Arg Val Val Tyr Leu Glu Gly Cys Gly Pro Pro Leu Arg Arg Trp Leu
            275                 280                 285 cgc gcg aac ctg gct gcc tcg ggc ggc tac gca atc gcg gtg gtg ctg      973
Arg Ala Asn Leu Ala Ala Ser Gly Gly Tyr Ala Ile Ala Val Val Leu
        290                 295                 300 ctg cag ggg gcg gag ctc ctg ctg gcc gcc cgg cta ctc ggg gcc ctc     1021
Leu Gln Gly Ala Glu Leu Leu Leu Ala Ala Arg Leu Leu Gly Ala Leu
    305                 310                 315 gct gcc cgc agt ggg gcg gcg tac ggc ccc gga gcg cac ggg gag gac     1069
Ala Ala Arg Ser Gly Ala Ala Tyr Gly Pro Gly Ala His Gly Glu Asp
320                 325                 330                 335 cgc gct ggc ccc cag agc ccc agc ccc ggc gcc ccg ccc gct gcc aaa     1117
Arg Ala Gly Pro Gln Ser Pro Ser Pro Gly Ala Pro Pro Ala Ala Lys
                340                 345                 350 ccc gcc cgg ggc tgagcgcacg ccccgaggtc cgagaccgcc acgcacaggg         1169
Pro Ala Arg Gly
            355 atacagggg cgcctccgcc cggctaaaaa gcgctgcctg cgccgccgcc gccgcctgat    1229
ttcgctcggg cttcgggtga cttcgccgca ggacctaccc agctcgctca cttcgctcgc   1289
tccgcgtccc ccatgccagc ccccaacgca gggcgcccgg cgaagccacg ggactggcgg   1349
gaggagcacg cggggccgga ggaaatcctg gagctgaccc tcacctccga gccccactc    1409 ccacccagc cgcacagttc ccacctcctg gcacctccct ccctggggc cgccacccct     1469 tctgggctcg tgatggtgga gctaaggtcc aggcctctcc ctcccgagtg catttttggg   1529
gagatagtaa atgttttatt cgggtgtatc attcatacag taaagacacc aatcttcaaa   1589
aaaaaaaaaa aa                                                       1601

<210> SEQ ID NO 4
<211> LENGTH: 355
<212> TYPE: PRT
<213> ORGANISM: Homo sapiens

<400> SEQUENCE: 4

Met Glu Glu Gly Glu Arg Ser Pro Leu Leu Ser Gln Glu Thr Ala Gly
1               5                   10                  15

Gln Lys Pro Leu Ser Val His Arg Pro Pro Thr Ser Gly Cys Leu Gly
                20                  25                  30

Pro Val Pro Arg Glu Asp Gln Ala Glu Ala Trp Gly Cys Ser Cys Cys
            35                  40                  45

Pro Pro Glu Thr Lys His Gln Ala Leu Ser Gly Thr Pro Lys Lys Gly
        50                  55                  60

Pro Ala Pro Ser Leu Ser Pro Gly Ser Ser Cys Val Lys Tyr Leu Ile
65                  70                  75                  80

Phe Leu Ser Asn Phe Pro Phe Ser Leu Leu Gly Leu Leu Ala Leu Ala
                85                  90                  95

Ile Gly Leu Trp Gly Leu Ala Val Lys Gly Ser Leu Gly Ser Asp Leu
            100                 105                 110
```

```
Gly Gly Pro Leu Pro Thr Asp Pro Met Leu Gly Leu Ala Leu Gly Gly
        115                 120                 125

Leu Val Val Ser Ala Ala Ser Leu Ala Gly Cys Leu Gly Ala Leu Cys
        130                 135                 140

Glu Asn Thr Cys Leu Leu Arg Gly Phe Ser Gly Gly Ile Leu Ala Phe
145                 150                 155                 160

Leu Val Leu Glu Ala Val Ala Gly Ala Leu Val Val Ala Leu Trp Gly
        165                 170                 175

Pro Leu Gln Asp Ser Leu Glu His Thr Leu Arg Val Ala Ile Ala His
        180                 185                 190

Tyr Gln Asp Asp Pro Asp Leu Arg Phe Leu Leu Asp Gln Val Gln Leu
        195                 200                 205

Gly Leu Arg Cys Cys Gly Ala Ala Ser Tyr Gln Asp Trp Gln Gln Asn
        210                 215                 220

Leu Tyr Phe Asn Cys Ser Ser Pro Gly Val Gln Ala Cys Ser Leu Pro
225                 230                 235                 240

Ala Ser Cys Cys Ile Asp Pro Arg Glu Asp Gly Ala Ser Val Asn Asp
                245                 250                 255

Gln Cys Gly Phe Gly Val Leu Arg Leu Asp Ala Asp Ala Gln Arg
        260                 265                 270

Val Val Tyr Leu Glu Gly Cys Gly Pro Pro Leu Arg Arg Trp Leu Arg
        275                 280                 285

Ala Asn Leu Ala Ala Ser Gly Gly Tyr Ala Ile Ala Val Val Leu Leu
        290                 295                 300

Gln Gly Ala Glu Leu Leu Leu Ala Ala Arg Leu Leu Gly Ala Leu Ala
305                 310                 315                 320

Ala Arg Ser Gly Ala Ala Tyr Gly Pro Gly Ala His Gly Glu Asp Arg
                325                 330                 335

Ala Gly Pro Gln Ser Pro Ser Pro Gly Ala Pro Pro Ala Ala Lys Pro
                340                 345                 350

Ala Arg Gly
        355

<210> SEQ ID NO 5
<211> LENGTH: 27
<212> TYPE: DNA
<213> ORGANISM: Artificial
<220> FEATURE:
<223> OTHER INFORMATION: PCR sense primer for OCSP

<400> SEQUENCE: 5
caccatggag gagggggaga ggagccc                                        27

<210> SEQ ID NO 6
<211> LENGTH: 23
<212> TYPE: DNA
<213> ORGANISM: Homo sapiens

<400> SEQUENCE: 6
gccccgggcg ggtttggcag cgg                                           23
```

ANTIBODY AGAINST TUMOR SPECIFIC ANTIGEN AS TARGET

This application is a continuation of International Application No. PCT/JP2004/003048, filed Mar. 9, 2004, which claims the benefit under 35 U.S.C. 365(c) of Japanese Application No. 2003-063648, filed Mar. 10, 2003.

TECHNICAL FIELD

The present invention relates to an antibody useful in cancer treatment, a pharmaceutical composition for treating cancer characterized in that it contains the antibody as an active ingredient, a method of detecting cancer and a cancer detection kit.

BACKGROUND ART

Tumor cells are known to express antigenic proteins which are intrinsic to the particular type of tumor cells (hereinafter sometimes referred to as a "tumor-associated antigens"). Attempts have been made to develop new therapies for treating tumors by targeting tumor-associated antigens. Monoclonal antibodies that elicit an antigen-antibody response specific to such tumor-associated antigens are known to induce various types of in vivo immune responses (antibody-dependent cell-mediated cytotoxicity (ADCC) and complement-dependent cytotoxicity (CDC), etc.) to attack cancer cells, thereby inducing cell death. Monoclonal antibodies useful for tumor treatment have been developed.

However, the range of monoclonal antibodies useful for tumor treatment is limited. The monoclonal antibodies presently available are capable of treating only a few types of tumors including metastatic breast cancer, acute leukemic myelosis, intractable chronic lymphoma, non-Hodgkin's lymphoma, and multiple myeloma. Development of monoclonal antibodies applicable to treatment of other tumors is desirable.

To obtain a monoclonal antibody useful for tumor treatment, it is necessary to identify a protein specifically expressed in a tumor cell and obtain a monoclonal antibody against this protein antigen.

Human oculospanin protein was obtained as an Expressed Sequence Tag (EST) clone derived from a gene expressed on the retinal pigment epithelium and the ocular choroidal membrane (Molecular Vision (2002) 8, 25-220). The human oculospanin gene has an open reading frame of 1068 bp. Human oculospanin consists of 355 amino acids and is estimated to have a molecular weight of 36.4 kDa based on the DNA sequence. However, the relationship between human oculospanin and tumors is still unknown.

DISCLOSURE OF THE INVENTION

The present invention provides a method for detecting cancer by finding a gene specifically expressed in a cancer cell and detecting expression of the gene, a cancer detection kit for use in the detection method, an antibody which specifically binds an expression product of the gene, an antibody having cytotoxic activity and a pharmaceutical composition for treating cancer containing the antibody as an active ingredient.

The present inventors have identified a gene specifically expressed in human cancer tissue and found that the expression level of human oculospanin gene, which is of unknown function, is significantly higher in melanoma cells. Based on this finding, they succeeded in providing a method of detecting cancer using the gene, a detection kit for cancer, and a pharmaceutical composition for treating cancer containing an anti-human oculospanin antibody, thereby accomplishing the present invention.

More specifically, the present invention provides:

(1) An antibody which specifically binds to human oculospanin and has cytotoxic activity against a cell expressing that protein;

(2) An antibody which specifically binds to a protein comprising an amino acid sequence represented by Sequence ID No. 2 of the sequence listing and/or an amino acid sequence represented by Sequence ID No. 4 of the sequence listing and which has cytotoxic activity against a cell expressing these protein(s);

(3) An antibody according to section (1) or (2), characterized in that the cytotoxic activity is antibody-dependent cell-mediated cytotoxicity;

(4) An antibody according to section (1) or (2), characterized in that the cytotoxic activity is complement-dependent cytotoxicity;

(5) An antibody according to section (1) or (2), characterized in that the cytotoxic activity is complement-dependent cell-mediated cytotoxicity;

(6) An antibody according to section (1) or (2), characterized in that the cytotoxic activity is apoptosis induction;

(7) An antibody according to any one of sections (1) to (6), characterized in that the antibody is a monoclonal antibody;

(8) An antibody according to section (7), characterized in that the antibody is produced by mouse hybridoma O3B8-2C9-4F3 (FERM BP-08627);

(9) An antibody according to any one of sections (1) to (8), characterized in that the antibody is humanized;

(10) An antibody according to any one of sections (1) to (7), characterized in that the antibody is a complete human antibody;

(11) An antibody according to any one of sections (1) to (10), characterized in that the antibody is an IgG antibody;

(12) A method of detecting cancer, comprising the following steps 1) to 4) of:

1) extracting a total RNA fraction from a specimen taken from a test subject;

2) extracting a total RNA fraction from a specimen taken from a healthy subject;

3) measuring the expression level of a polynucleotide represented by the following a) or b) in the total RNA fractions derived from steps 1) and 2):

a) a polynucleotide comprising the nucleotide sequence represented by Sequence ID No. 1 of the sequence listing;

b) a polynucleotide which hybridizes with a polynucleotide comprising a nucleotide sequence complementary to that of the polynucleotide according to a) under stringent conditions; and 4) analyzing the difference in expression level of the polynucleotide between the total RNA fractions derived from step 1) and step 2), measured in the step 3) and thereby detecting cancer in the test subject of step 1);

(13) A method of detecting cancer, comprising the steps 1) to 3) of:

1) measuring the expression level of a protein comprising an amino acid sequence represented by Sequence ID No. 2 of the sequence listing and/or the expression level of a protein comprising an amino acid sequence represented by Sequence ID No. 4, in a specimen taken from a test subject;

2) measuring the expression level of at least one of the proteins according to step 1) in a specimen taken from a healthy subject; and 3) analyzing a difference in expression level between the protein detected in step 1) and the protein detected in step 2), and thereby detecting cancer in the test subject;

(14) A method according to either section 12 or 13, characterized in that the cancer is skin cancer;

(15) A method according to either section 12 or 13, characterized in that the cancer is melanoma;

(16) A method according to any one of sections (12), (14) or (15), characterized in that the expression level of the polynucleotide is measured by Northern blotting, dot blotting, slot blotting, RT-PCR, ribonuclease protection assay or a run-on assay;

(17) A method according to any one of sections (12), (14) or (15), characterized in that the expression level of the polynucleotide is measured using a gene chip or array prepared from DNAs comprising complementary DNAs derived from the specimen or partial sequences of the complementary DNAs;

(18) A method according to any one of sections (13) to (15) characterized in that the expression level of the protein is measured using an antibody or a ligand which specifically binds to the protein;

(19) A method according to any one of sections (13) to (15) characterized in that the expression level of the protein is measured by Western blotting, dot blotting, slot blotting or enzyme-linked immunosorbent assay (ELISA method);

(20) A detection kit for cancer comprising at least one component selected from the following 1) to 3):

1) an oligonucleotide primer 15 to 30 bases in length for specifically amplifying a polynucleotide comprising a nucleotide sequence represented by Sequence ID No. 1 of the sequence listing;

2) a polynucleotide probe of not less than 15 contiguous nucleotides capable of hybridizing with a polynucleotide comprising the nucleotide sequence represented by Sequence ID No. 1 of the sequence listing under stringent conditions, and thereby detecting the polynucleotide; and 3) an immobilized specimen having a polynucleotide comprising the nucleotide sequence represented by Sequence ID No. 1 of the sequence listing immobilized thereon;

(21) A detection kit for cancer comprising at least one of the following components 1) and 2):

1) an antibody capable of specifically binding to a protein comprising an amino acid sequence represented by Sequence ID No. 2 of the sequence listing and/or an amino acid sequence represented by Sequence ID No. 4 of the sequence listing, and thereby detecting the protein(s);

2) a secondary antibody capable of binding to an antibody according to section 1) above;

(22) A kit according to sections (20) or (21), characterized in that the cancer is skin cancer;

(23) A kit according to sections (20) or (21), characterized in that the cancer is melanoma;

(24) A pharmaceutical composition for treating cancer comprising at least one of the antibodies according to sections (1) to (11);

(25) A pharmaceutical composition for treating cancer comprising an oligonucleotide having a nucleotide sequence complementary to a nucleotide sequence represented by Sequence ID No. 1 of the sequence listing or a partial sequence of the nucleotide sequence of Sequence ID No. 1.

(26) A pharmaceutical composition according to section (24) or (25), characterized in that the cancer is skin cancer; and

(27) A pharmaceutical composition according to section (24) or (25), characterized in that the cancer is melanoma.

BEST MODE FOR CARRYING OUT THE INVENTION

Figure 1:
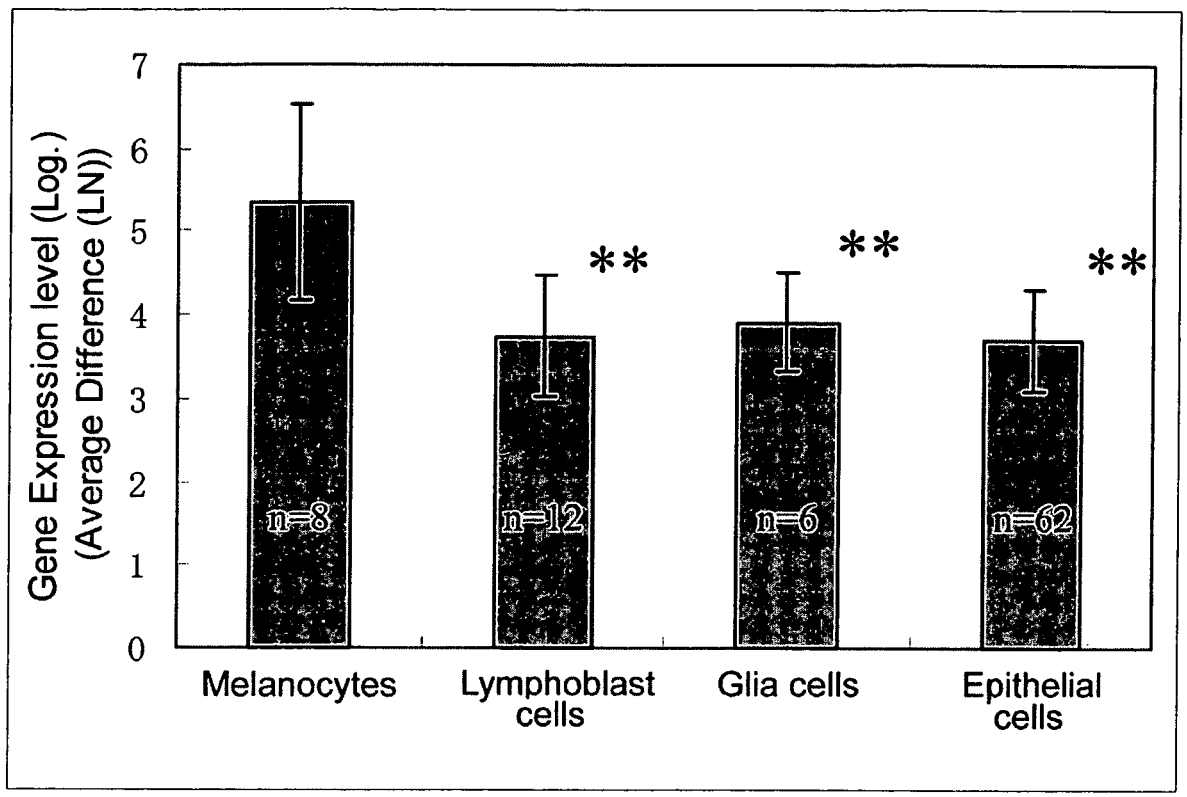
FIG. 1, the upper figure, is a graph showing the expression level of the human oculospanin gene in various types of cells; and the lower figure is a graph showing the expression level of the human oculospanin gene in a healthy person's skin samples and in melanoma samples.
Figure 1:
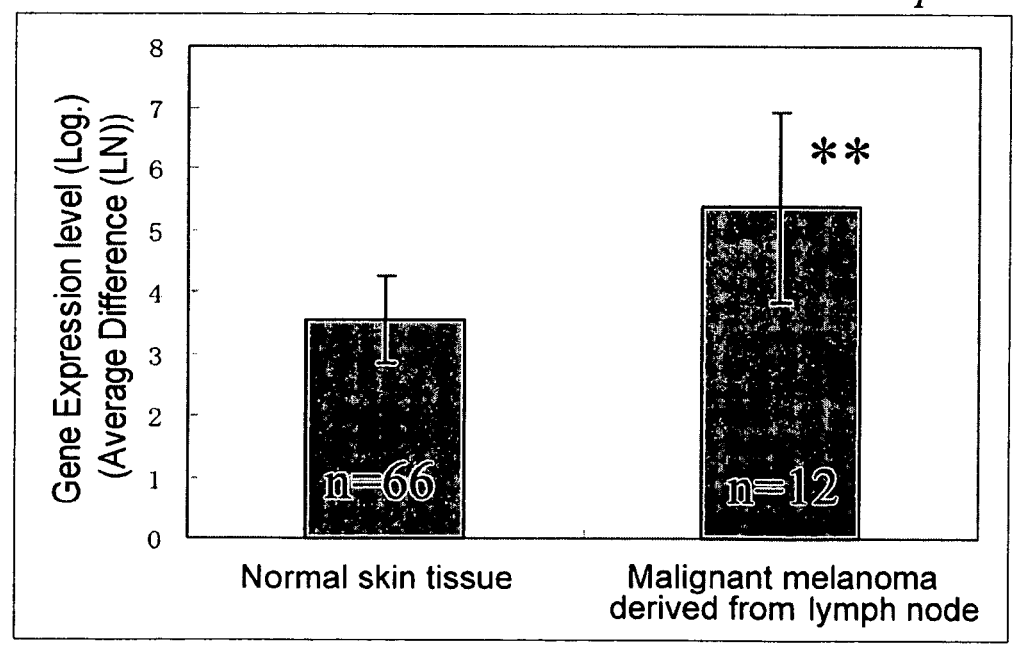

In the specification of the present invention, a compound having a cancer therapeutic effect is a compound having an activity in suppressing cancer growth and/or an activity of reducing cancer. In the specification of the present invention, the terms "cancer" and "tumor" have the same meaning. The term "gene" as used herein includes not only DNA, but also mRNA thereof, cDNA and cRNA thereof. Accordingly, the term "human oculospanin gene" as used herein includes DNA, mRNA, cDNA, and cRNA of the human oculospanin gene. The term "polynucleotide" as used herein has the same meaning as that of a nucleic acid and thus includes DNA, RNA, probe, oligonucleotide and primer. The terms "polypeptide" and "protein" are used indistinguishably herein. The term "RNA fraction" as used herein refers to a fraction containing RNA. Furthermore, the term "cell" used herein includes a cell within an animal body and a cultured cell. The term "canceration of a cell" used herein refers to the abnormal proliferation of cells, which is caused by their lack of sensitivity to contact inhibition and their scaffold independent-proliferation. A cell exhibiting such abnormal proliferation is referred to as a "cancer cell". In the specification, a protein having the same function as that of human oculospanin, such as canceration activity, is also referred to as a "human oculospanin". Note that the term "oncogene" as used in the present invention includes a precancerous gene and a proto-oncogene other than the oncogene.

The term "cytotoxicity" used herein refers to a pathological change to a cell caused by any reason. Therefore, cytotoxicity includes not only externally inflicted direct damage, but also various structural and functional changes that may occur within a cell, which include DNA cleavage, dimerization of bases, chromosomal cleavage, malfunction of cellular mitotic apparatus, and a reduction in enzymatic activities. The term "cytotoxic activity" used herein refers to any activity that causes cytotoxicity, as mentioned above.

The term "hybridizes under stringent conditions" refers to hybridization which is performed at 68° C. in a commercially available hybridization solution, namely ExpressHyb (manufactured by Clontech), or hybridization which is performed at 68° C. in the presence of NaCl at 0.7 to 1.0 M using a filter having DNA immobilized thereon, followed by washing at 68° C. with 0.1 to 2×SSC solution (1×SSC solution contains 150 mM NaCl and 15 mM sodium citrate), resulting in hybridization. The above term also includes hybridization under conditions equivalent to those above.

1. Human Oculospanin (1) Confirmation of Specific Expression of the Human Oculospanin Gene As a result of analyzing expression levels of the human oculospanin gene in various types of human cells, it was found that the gene is expressed at a significantly higher expression level in melanocytes compared to other tissues. Furthermore, the present inventors found that the level of expression of the human oculospanin gene in melanoma is significantly higher than in normal melanocytes. To explain more specifically, they found the following: when the level of expression of human oculospanin in melanocytes, lymphoblasts and glia cells, and epithelial cells is compared, the expression level in melanocytes is found to be significantly higher. Furthermore, when the level of expression of human oculospanin in normal skin cells is compared to that in melanoma, the expression level is significantly higher in the melanoma. From these findings, it can be concluded that human oculospanin may be involved in canceration of cells and/or in proliferation of cancer cells. This suggests that the canceration state and/or proliferation state of cancer cells caused by excessive expression of human oculospanin can be determined by measuring the level of expression of human oculospanin in individual cells and/or tissues. An example of such cancer is skin cancer, in particular, melanoma. However, this finding is applicable to cancers other than skin cancer, provided that human oculospanin is expressed in the cancer at a significantly higher level than in other tissues.

The nucleotide sequence of the open reading frame (ORF) of the human oculospanin gene is represented by Sequence ID No. 1 of the sequence listing and the amino acid sequence thereof is represented by Sequence ID No. 2. Furthermore, cDNA of the human oculospanin gene has been registered with GenBank as *Homo sapiens* oculospanin (OCSP) mRNA under Accession No. NM_031945. The cDNA nucleotide sequence registered at GenBank is represented by Sequence ID No. 3 of the sequence listing. The ORF is represented by nucleotide Nos. 65 to 1129 of Sequence ID No. 3. Furthermore, the amino acid sequence of human oculospanin registered at GenBank is represented by Sequence ID No. 4 of the sequence listing. A protein comprising an amino acid sequence having one or several amino acids replaced, deleted from or added to the amino acid sequence of human oculospanin and exhibiting the same biological activity as that of human oculospanin is also included herein as a human oculospanin.

2. Method of Detecting Cancer

Human oculospanin, since it is highly expressed in cancer cells, especially, melanoma, is thought to be involved in canceration of cells, particularly skin cells, and/or proliferation of cancer cells. The term "specimen" refers to a sample taken from a test subject or a clinical specimen, and includes samples of tissues, excrement or the like, such as samples of blood, body fluids, prostate gland, testes, penis, bladder, kidney, oral cavity, pharynx, lip, tongue, gingival, nasopharynx, esophagus, stomach, small intestine, large intestine, colon, liver, gall bladder, pancreas, nose, lung, bone, soft tissue, skin, breast, uterus, ovary, brain, thyroid, lymph node, muscle, and adipose tissue. In the present invention, skin and lymph node are preferred tissue samples.

(1) Method of Detecting Cancer using the Level of Expression of the Human Oculospanin Gene.

A method of detecting cancer by using the level of expression of the human oculospanin gene specifically comprises the following steps 1) to 4):

1) a step of extracting a total RNA fraction from a specimen taken from a test subject;
2) a step of extracting a total RNA fraction from a specimen taken from a healthy person;
3) a step of measuring the level of expression of the human oculospanin gene in the total RNA fractions according to steps 1) and 2); and
4) a step of analyzing the difference in the level of expression of the gene between the total RNA fraction derived from steps 1) and 2), measured in step 3) and thereby detecting cancer of the test subject of step 1).

The individual steps will be explained more specifically as follows.

a) Step 1): Extracting a Total RNA Fraction from a Specimen Taken from a Test Subject.

In extracting the total RNA fraction from a specimen, human tissue is obtained by an appropriate method satisfying the ethical standards for experimentation. The tissue obtained is dissolved directly in an RNA extraction solvent (containing a ribonuclease inhibitor, such as phenol). Alternatively, cells of the tissue obtained are collected by abrading them using a scraper so as not to break the cells, or gently extracting them from the tissue using a proteolytic enzyme such as trypsin, and then immediately subjecting the cells to an RNA extraction step.

Examples of RNA extraction methods that may be used include: guanidine thiocyanate/cesium chloride ultracentrifugation methods, guanidine thiocyanate/hot phenol methods, guanidine hydrochloride methods, and acidic guanidine thiocyanate/phenol/chloroform methods (Chomczynski, P. and Sacci, N., Anal. Biochem. (1987), 162, 156-159). Of these, acidic guanidine thiocyanate/phenol/chloroform methods are particularly suitable. Alternatively, a commercially available RNA extraction reagent, such as ISOGEN (manufactured by Nippon Gene Co., Ltd.) or TRIZOL reagent (manufactured by Gibco BRL) may be used in accordance with the protocol provided with the reagent.

From the total RNA fraction obtained, if necessary, it is preferred that mRNA alone is purified and used. Any suitable purification method can be used. For example, mRNA can be purified by adsorbing mRNA onto a biotinylated oligo (dT) probe, attaching the mRNA to paramagnetic particles having streptavidin immobilized thereon via binding of biotin to streptavidin, washing the particles, and eluting mRNA. Alternatively, mRNA may be purified by adsorbing mRNA onto an oligo (dT) cellulose column and eluting the mRNA therefrom. However, an mRNA purification step is not essential in methods of the present invention. Provided that expression of a desired polynucleotide can be detected, a total RNA fraction may be used, as can be done in the later steps.

b) Step 2): Extracting a Total RNA Fraction from a Specimen Taken from a Healthy Person.

In the present invention, a healthy person means a person who does not have cancer. The determination as to whether or not a person is healthy can be made by measuring the concentration of human oculospanin and determining whether or not the concentration value measured falls within a predetermined range for a healthy person. Alternatively, the correlation between the expression level of human oculospanin and the degree of cancer formation can be investigated in advance, and then, determination of whether or not a test subject is a healthy person can be made by measuring the expression level of human oculospanin in a specimen taken from the test subject. The preparation of a total RNA fraction from a healthy person can be performed in the same manner as described in Step 1) above.

c) Step 3): Measuring the Level of Expression of the Human Oculospanin Gene in a Total RNA Fraction According to Steps 1) and 2).

The level of expression of the human oculospanin gene is represented by the expression level of a polynucleotide that can hybridize with a polynucleotide which comprises the nucleotide sequence represented by Sequence ID No. 1 of the sequence listing or a polynucleotide which comprises a nucleotide sequence complementary to the nucleotide sequence represented by Sequence ID No. 1 of the sequence listing, under stringent conditions.

The expression level of the human oculospanin gene, can be determined using an immobilized specimen, this and other methods are described below.

(a) Assay using Immobilized Samples
(i) Immobilized Samples
The following are examples of immobilized samples.
i) Gene Chips A gene chip may be used on which there is immobilized either an anti-sense oligonucleotide, which is synthesized based on an EST (expressed sequence tag) sequence from a database, or an mRNA sequence. Examples of such gene chips include gene chips manufactured by Affymetrix (Lip Shutz, R. J. et al., Nature Genet. (1999), 21, supplement, 20-24), but are not limited thereto, and may be prepared based on any known method. When mRNA derived from a human cell is analyzed, a gene chip derived from human sequences is preferably used. For example, the human sequences U95 set or U133 set manufactured by Affymetrix may be used. However, suitable gene chips are not limited to these and a gene chip derived from, for example, an animal species closely related to a human may be used.

ii) Arrays or Membrane Filters on Which There is Immobilized a cDNA or RT-PCR Product Prepared From Total Human RNA or Total RNA, Taken From a Specific Tissue of a Human Subject.

The cDNA or RT-PCR product can be a clone obtained by performing a reverse transcription reaction and PCR using a primer prepared based on a sequence from a database such as a human EST database. The cDNA or RT-PCR product may have been selected previously by use of a subtraction method (Diatchenki, L, et al., Proc. Natl, Acad. Sci, USA (1996) 93, 6025-6030) or a differential display method (Liang, P., et al., Nucleic Acids Res., (1992) 23, 3685-3690) based on total RNA in which the expression level differs between a person having a tumor and a person having no tumor. The array or filter may be one which is commercially available, such as those provided by IntelliGene (manufactured by Takara Bio). Alternatively, the cDNA or RT-PCR product may be immobilized using a commercially available spotter such as GMS417 arrayer (manufactured by Takara Bio) to make an array or a filter.

(ii) Preparation of a Probe and Analysis

Not a specific mRNA clone but all of the expressed mRNA are labeled and used as a labeled probe. Crude mRNA (unpurified) may be used as a starting material for preparing a probe; however, preferably poly $(A)^+$ RNA is used which has been purified by the aforementioned method. A method of preparing a labeled probe and a method of detecting and analyzing the probe using various types of immobilized sample are further described as follows.

i) Gene Chip Manufactured by Affymetrix

A biotin-labeled cRNA probe is prepared in accordance with the protocol (Affymetrix's Expression Analysis Technical Manual) provided with the GeneChip manufactured by Affymetrix. Subsequently, hybridization and analysis is performed to detect and analyze light emitted from adipic acid using an Affymetrix analyzer (GeneChip Fluidics Station 400) in accordance with the protocol (Expression Analysis Technical Manual) provided with the GeneChip manufactured by Affymetrix.

ii) Array

In order to detect cDNA, a label must be attached to the cDNA when it is prepared from poly $(A)^+$ RNA using a reverse transcriptase reaction. To obtain fluorescently labeled cDNA, d-UTP labeled with a fluorescent dye such as Cy3 or Cy5 may be included in the reaction mixture. If poly$(A)^+$ RNA derived from a melanoma cell and poly $(A)^+$ RNA derived from a cell used as a control are labeled with different dyes, then both types of poly $(A)^+$ RNAs may be used simultaneously in a mixture. When a commercially available array is used, e.g. an array manufactured by Takara Bio Co., Ltd. hybridization and washing are preformed in accordance with the protocol provided and then a fluorescent signal is detected using a fluorescent signal detector (for example, the GMS418 array scanner manufactured by Takara Bio Co., Ltd.) and thereafter subjected to analysis. The choice of array for use as described herein is not limited to those which are commercially available. An home-made array and an array specifically prepared in-house may be used.

iii) Membrane Filter

When preparing cDNA from poly $(A)^+$ RNA by reverse transcription, a labeled probe can be prepared by adding a radioisotope (for example, d-CTP) to the reaction. Hybridization is performed in accordance with customary methods. More specifically, hybridization can be performed using the Atlas system (manufactured by Clontech), which is a microarray formed using a commercially available filter, after hybridization the microarray is washed. Thereafter, detection and analysis are performed using an analyzer (for example, Atlas Image manufactured by Clontech).

In any one of the methods i) to iii), a probe derived from human tissue is hybridized with the immobilized samples of the same lot. The probe which is used can be charged, but the hybridization conditions used are kept the same. When fluorescently labeled probes are used, if the probes are labeled with different fluorescent dyes, then probes of different types can be added simultaneously in the form of a mixture and hybridized with the immobilized samples. Thereafter, fluorescent intensity can be read simultaneously (Brown, P. O. et al., Nature Genet., (1999) 21, supplement, p. 33-37).

(b) Other Measurement Methods

In addition to the measurement methods mentioned above, there are subtraction cloning methods (see Experimental Medicine, Supplementary Volume, New Genetic Engineering Handbook, published by Yodosha Co., Ltd. (1996), p32-35); differential display methods (Basic Biochemical Experimental Method 4, nucleic acid/gene experiment, II. Applied series, Tokyo Kagakudojin (2001), p125-128); and methods using a reporter gene: chloramphenicol acetyltransferase (such as a pCAT3-Basic vector manufactured by Promega), β-galactosidase (such as a pβgal-Basic vector manufactured by Promega), secreted alkaline phosphotase (such as pSEAP2-Basic manufactured by Clontech); or green-fluorescent protein (such as pEGFP-1 manufactured by Clontech). However, the choice of measurement method is not limited to these methods.

Step 4) Analyzing the Difference in the Level of Expression of the Gene Between the Total RNA Fraction Derived from Steps 1) and 2), Measured in Step 3) and Detecting Cancer in a Test Subject of Step 1).

The difference in the level of expression of human oculospanin between a specimen derived from a healthy person and a specimen derived from a test subject is analyzed. If a specimen shows a significantly high expression level of human oculospanin, it is determined that the possibility of having cancer, particularly skin cancer, and more particularly melanoma, is high, that is, cancer can be detected. The term "significantly high expression level" refers to the case where, when analysis is preformed by using GeneChip (manufactured by Affymetrix) and microarray Suite Ver. 3.0. (manufactured by Affymetrix), an average difference value of a gene derived from a melanoma cell is significantly high compared to that of a normal melanocyte.

Alternatively, the level of expression of human oculospanin is measured, and then assessed to determine whether or not the measured concentration value falls within a predetermined range for a healthy person. If the value exceeds the range, the subject has cancer. The diagnosis of cancer can be made in this manner. Otherwise, the correlation between the level of expression of the human oculospanin gene and the degree of cancer formation in a healthy person is previously investigated, and then, the expression level of human oculospanin gene of a specimen taken from the test subject is measured. Also, in this manner, whether or not a test subject is a healthy person or not can be determined.

(3) Method of Detecting Cancer by Using the Level of Expression of Human Oculospanin (Protein Expression Level).

More specifically, a method of detecting cancer using the level of expression of human oculospanin can be a method including the steps 1) to 3) below.
1) measuring the level of expression of human oculospanin protein in a specimen taken from a subject;
2) measuring the level of expression of the same protein as described in step 1) in a specimen taken from a healthy person; and,
3) analyzing the difference between the level of expression of the protein measured in steps 1) and 2) and thereby detecting that a subject has cancer.

The individual steps are described in more detail as follows:

a) Measuring the Expression Level of Human Oculospanin Protein in a Specimen Taken from a Subject.

(i) Preparation of a Sample from a Specimen for Protein Measurement.

The specimen is subjected to high-speed centrifugation as necessary to remove insoluble substances, and then prepared as a sample for ELISA/RIA and Western blot.

To prepare a sample for ELISA/RIA, skin or lymph node tissue taken from a subject is used directly, or diluted appropriately in a buffer solution before use. For Western blotting (electrophoresis), a solution extracted from skin or lymph node tissue can be used directly as the sample, or diluted appropriately with a buffer solution, and mixed with a sample buffer solution (manufactured by Sigma) containing 2-mercaptoethanol for SDS-polyacrylamide gel electrophoresis. For dot or slot blotting, a solution extracted from skin or lymph node tissue can be used undiluted or diluted appropriately in a buffer solution, the samples are directly adsorbed to a membrane using a blotting device.

(b) Immobilization of Sample

A protein in the sample thus obtained can be specifically detected by precipitating the protein using a procedure such as immunoprecipitation or ligand binding, either without additional immobilization or after direct immobilization thereof. For immobilizing a protein, a membrane used can be one such as is used in Western blotting, dot blotting or slot blotting. Examples of such membranes include nitrocellulose membranes (for example, as manufactured by BioRad), nylon membranes such as Hybond-ECL (manufactured by Amersham Pharmacia), cotton membranes such as blot absorbent filters (for example, as manufactured by BioRad) and polyvinylidene difluoride (PVDF) membranes (for example, manufactured by BioRad).

To detect and quantify a protein using an ELISA or RIA method, a sample or a diluted sample solution (for example, diluted with phosphate buffered saline (hereinafter referred to as "PBS") containing 0.05% sodium azide) is dispensed into a 96-well plate, such as an Immunoplate, Maxisorp, (manufactured by Nunc) and incubated without agitation at a temperature in the range of 4° C. to room temperature overnight, or at 37° C. for 1 to 3 hours, thereby allowing the protein to adsorb the bottom surface of the wells to immobilize the protein.

Antibody against human oculospanin can be obtained using a customary method (see, for example, New Biochemical Experimental Course 1, Protein 1, p. 389-397, 1992), which comprises immunizing an animal with human oculospanin or a polypeptide arbitrarily selected from the amino acid sequences of human oculospanin, taking the antibody produced in the body and purifying it. Alternatively, a monoclonal antibody can be obtained in accordance with a method well known in the art (for example, Kohler and Milstein, Nature 256, 495-497, 1975, Kennet, R. ed., Monoclonal Antibody, p. 365-367, 1980, Prenum Press, N, Y.), which comprises fusing an antibody-producing cell producing an antibody against human oculospanin with a myeloma cell to form a hybridoma cell.

Human oculospanin protein for use as an antigen can be obtained by introducing a human oculospanin gene into a host cell by gene manipulation. To explain more specifically, human oculospanin protein may be obtained by preparing a vector capable of expressing the human oculospanin gene, introducing the vector into the host cell, expressing the gene, and purifying the expressed human oculospanin protein.

(c) Measurement of the Level of Expression of Human Oculospanin.

The level of expression of human oculospanin can be represented by the level of expression of a protein comprising the amino acid sequence represented by Sequence ID No. 2 of the sequence listing.

The expression level can be measured by a method known in the art, such as a Western blotting or a dot/slot blotting method, using anti-human oculospanin antibody.

b) Step 2; Measuring the Expression Level of the Same Protein as Described in Step 1 in a Specimen Taken from a Healthy Person.

Measurement of the level of expression of human oculospanin in a specimen taken from a healthy person can be performed in the same manner as described in step 1) above.

c) Step 3; Analyzing the Difference Between the Level of Expression of the Protein Measured in Steps 1) and 2) and Thereby Detecting that a Subject has Cancer.

The difference in the level of expression of human oculospanin between the specimens from a healthy person and a test subject is analyzed. As a result, if a specimen exhibits a significantly high expression level of human oculospanin, it can be determined that there is a high probability of a subject having cancer, particularly, skin cancer, and more particularly, melanoma. In this manner, cancer can be detected.

Alternatively, cancer can be detected by measuring the concentration of human oculospanin and analyzing whether or not the measured concentration value falls within the predetermined range for a healthy person. In this case, if the concentration value of a subject is higher than the range for a healthy person, it is determined that the subject has cancer. Furthermore, by investigating the correlation between the level of expression of human oculospanin and the degree of cancer formation in a healthy person, it is possible to determine whether or not a subject is healthy based on the level of expression of human oculospanin in a specimen taken from the subject.

3. Investigation of the Human Oculospanin Gene and Human Oculospanin

The human oculospanin gene and human oculospanin are expressed at a significantly high level in melanocytes in normal human tissues, and they are, expressed at a significantly higher level in melanoma than in normal melanocytes.

In a method of examining the function of human oculospanin, full-length cDNA is first taken from a human cDNA library, derived from cells expressing human oculospanin, by a known method such as a colony hybridization method. Then, the full-length cDNA is introduced into a mouse or a human cell, highly-expressed therein, and assessment is carried out to investigate whether or not the cDNA affects the cell.

To express cDNA in an animal, a method may be used in which the full-length cDNA obtained is introduced into a virus vector and the vector is administered to the animal. Examples of gene transfection using a virus vector include methods of introducing cDNA by integrating it into a DNA virus or an RNA virus, such as a retrovirus, adeno virus, adeno-associated virus, herpes virus, vaccinia virus, pox virus, or polio virus. Of these, methods using retrovirus, adeno virus, adeno-associated virus and vaccinia virus are preferred.

Examples of non-viral gene transfection include administering an expression plasmid directly into the muscle (DNA vaccination), liposome treatment, lipofection, microinjection, calcium phosphate treatment, electroporation and the like. Of these, DNA vaccination and liposome treatment are preferred.

Furthermore, by transfecting full-length cDNA into cultured cells, such as muscle cells, liver cells, or adipose cells derived from human, mouse or rat; or into primary muscle cells, liver cells, adipose cells or skin cells, and expressing the cDNA therein at a high level, it is possible to examine the functions of a target cell, more specifically, production and intake of sugars and lipids, control of glycolipid metabolism such as glycogen accumulation, or to see if there is any effect on the morphology of a cell. Conversely, by introducing into a cell an antisense nucleic acid to the total RNA of a gene to be examined, it is possible to examine the effects produced on the function and morphology of the target cell.

To introduce a full-length cDNA into an animal or a cell, the cDNA is integrated into a vector containing appropriate promoter sequences and transformation is carried out to transform the host cell with the vector. The expression promoter for use with a vertebrate cell may have a promoter that is typically located upstream of the gene to be expressed, an RNA splicing site, a polyadenylation site, a transcription termination sequence, etc. Furthermore, if necessary, a replication initiation point may be present. Examples of such an expression vector include, but are not limited to, pSV2dhfr having an early promoter of simian virus 40 (SV40) (Subramani, S. et al., Mol. Cell. Biol., (1981), 1, p854-864), retrovirus vectors pLNCX, pLNSX, pLXIN, pSIR (manufactured by Clontech), and cosmid vector pAxCw (manufactured by Takara Bio). These expression vectors can be integrated into a simian cell, such as a COS cell (Gluzman, Y. Cell (1981), 23, p. 175-182, ATCC: CRL-1650), a dihydrofolic acid reductase defective strain (Urlaub, G. and Chasin, L. A. Proc. Natl. Acad. Sci. USA (1980), 77, p. 4126-4220) of a Chinese hamster ovary cell (CHO cell, ATCC:CCL-61), human embryonic kidney derived 293 cell (ATCC: CRL-1573) and the like, by methods including a diethylaminoethyl (DEAE)-dextran method (Luthman, H and Magnusson, G., Nucleic Acids Res. (1983), 11, p. 1295-1308), a calcium phosphate-DNA co-precipitation method (Graham, F. L. and van der Eb, A. J. Virology (1973), 52, p. 456-457), and an electroporation method (Neumann, E. et al., EMBO J. (1982), 1, p. 841-845). However, the integration method and cell are not limited to those specifically described. In this manner, a desired transformant can be obtained.

Furthermore, using gene manipulation in a healthy animal, a transgenic animal can be obtained which highly expresses the desired gene. This can be used to examine the effects on cell morphology. Alternatively, the state of cells may be examined by preparing a knockout animal by knocking out the target gene in an animal having melanoma.

4. Human Oculospanin Gene and/or Human Oculospanin Detection Kit

The human oculospanin gene and/or human oculospanin can be detected using a kit containing at least one component selected from the group consisting of materials 1) to 5) below.

1) an oligonucleotide primer having a continuous sequence of 15 to 30 bases in length for specifically amplifying a polynucleotide comprising the nucleotide sequence represented by Sequence ID No. 1 of the sequence listing;
2) a polynucleotide probe having a continuous sequence of not less than 15 nucleotides capable of hybridizing with a polynucleotide comprising the nucleotide sequence represented by Sequence ID No. 1 of the sequence listing under stringent conditions, thereby enabling detection of the polynucleotide;
3) an immobilized specimen in which a polynucleotide comprising the nucleotide sequence represented by Sequence ID No. 1 of the sequence listing is immobilized;
4) An antibody which specifically binds to a protein comprising the amino acid sequence represented by Sequence ID No. 2 of the sequence listing, thereby enabling detection of the protein; and
5) A secondary antibody capable of binding to an antibody according to section 4) above.

The primer according to section 1) above can be easily constructed based on the nucleotide sequence of the human oculospanin gene (the nucleotide sequence represented by Sequence ID No. 1 of the sequence listing) by a customary method, for example, by a method using commercially available primer construction software (e.g., Wisconsin GCG package Version 10.2) and subjected to amplification. As an example of such a primer, more specifically, a primer for amplifying a polynucleotide comprising the nucleotide sequence represented by Sequence ID No. 1 of the sequence listing, use can be made of the combination of an oligonucleotide comprising the nucleotide sequence represented by Sequence ID No. 5 of the sequence listing and an oligonucleotide comprising the nucleotide sequence represented by Sequence ID No. 6 of the sequence listing. The probe according to section 2) above is a polynucleotide capable of hybridizing specifically with human oculospanin and being 100 to 1500 bases in length, preferably 300 to 600 bases in length. These primers and probes may be tagged with an appropriate label (such as an enzyme label, radioactive label, or fluorescent label) or may have a linker added thereto.

The immobilized specimen according to section 3) above can be prepared by immobilizing a probe according to section 2) onto a solid phase such as a glass plate, a nylon membrane, or the like. A method of preparing such an immobilized specimen is described in Section "2. Method of detecting cancer", Paragraph "(1) Method of detecting cancer using the level of expression of the human oculospanin gene, Sub paragraph "(1) Method of using an immobilized specimen". Examples of immobilized specimens include gene chips, cDNA arrays, oligo-array, and membrane filters.

A kit according to the present invention may contain a thermostable DNA polymerase, dNTPs (a mixture of dATP, dCTP, dGTP and dTTP) and a buffer solution. Examples of thermostable DNA polymerases include Taq DNA polymerase, LA Taq DNA polymerase (manufactured by Takara Shuzo Co., Ltd.), Tth DNA polymerase, and Pfu DNA polymerase. The type of buffer solution can be selected in accordance with the DNA polymerase which is to be used and $Mg^{2+}$ can be added, as needed.

The antibodies according to sections 4) and 5) above can be prepared by a method described in Section "2. Method of detecting cancer", Paragraph "(3) Method of detecting cancer by using the level of expression of human oculospanin (expression level of protein)" or a method described in Section "5. Preparation of anti-human oculospanin antibody". The antibody may be tagged with an appropriate label (such as an enzyme label, radioactive label, or fluorescent label).

A kit according to the present invention can be used for detection of a human oculospanin gene and/or human oculospanin protein, thereby determining the presence or absence of cancer and screening for a substance capable of suppressing cancer growth.

5. Preparation of an Anti-Human Oculospanin Antibody (1) Preparation of Antigen.

An antigen for preparing an anti-human oculospanin antibody can be a polypeptide comprising human oculospanin, a partial amino acid sequence thereof having a partial and continuous amino acid sequence comprising at least 6 bases, or derivatives thereof having an arbitrary amino acid sequence or a carrier added these.

Human oculospanin protein can be directly purified from human tumor tissues or cells, synthesized in vitro, or produced in host cells by gene manipulation. More specifically, in producing human oculospanin by gene manipulation, a human oculospanin gene is integrated into an expression vector, and thereafter the human oculospanin is synthesized in a solution containing enzymes, substrates and energy substances required for its transcription and translation. Alternatively, a prokaryotic or eukaryotic host cell can be transformed with the expression vector and then human oculospanin can be isolated. The nucleotide sequence of human oculospanin cDNA is described in: Graeme Wistow, Steven L. Bernstein, M. Keith Wyatt, Robert N. Fariss, Amita Behal, Jeffrey W. Touchman, Gerard Bouffard, Don Smith, and Katherine Peterson (2002), Expressed sequence tag analysis of human RPE/choroids for the NEIBank Project: Over 6000 non-redundant transcripts, novel genes and splice variants, Molecular Vision 8:205-220, and registered in the GenBank under Accession No. NM_031945. The ORF of the cDNA is shown in Sequence ID No. 1 of the sequence listing. The human oculospanin cDNA can be obtained from a cDNA library expressing human oculospanin by using a primer for specifically amplifying human oculospanin cDNA from the cDNA library as a template through a polymerase chain reaction (hereinafter referred to as the "PCR", (see Saiki, R. K., et al., (1988), Science 239, 487-49) herein termed a "PCR method".

The in vitro synthesis for a polypeptide can be preformed using, for example, the rapid translation system (RTS) manufactured by Roche Diagnostics; however, suitable synthesis methods are not limited to this particular method. In the case of RTS, the desired gene is cloned into an expression vector, under the control of a T7 promoter, and the expression vector is added to an in vitro reaction system. Consequently, mRNA is first transcribed from template DNA by T7 RNA polymerase and then translation is performed by ribosomes in a solution containing *Escherichia coli* lysate. In this manner, a target polypeptide can be synthesized in the reaction solution (Biochemica, 1, 20-23 (2001), Biochemica, 2, 28-29 (2001)).

Examples of suitable prokaryotic hosts include *Escherichia coli* and *Bacillus subtilis*. To transform a desired gene into these host cells, the host cells are transformed with a plasmid vector derived from a species compatible with the host, and containing a replicon, that is, a replication initiation point, and a regulatory sequence. Furthermore, it is preferred that the vector has a sequence capable of imparting a selectable phenotype to the cell to be transformed.

As a host cell an *Escherichia coli* strain, for example, a K12 strain can be used and pBR322 and pUC series plasmids can generally be used as vectors. However, the choice of host cell and vector is not limited thereto and any suitable known strain and vector may be used.

Promoters suitable for use in *Escherichia coli*, include the tryptophan (trp) promoter, lactose (lac) promoter, tryptophan lactose (tac) promoter, lipoprotein (lpp) promoter, and polypeptide chain extension factor Tu (tufB) promoter and the like. Any one of these promoters may be used for producing the desired polypeptide.

As a host cell, a *Bacillus subtilis* strain can be used, for example, the 207-25 strain is preferred. The vector pTUB 228 (Ohmura, K. et al., (1984), J. Biochem. 95, 87-93) can be used; however, the choice of *Bacillus subtilis* host and vector is not limited to this particular combination. By linking a DNA sequence encoding a signal peptide sequence for *Bacillus subtilis* α-amylase, the protein of interest can be expressed and secreted from the cell.

Examples of eukaryotic host cells include vertebrate, insect and yeast cells. Examples of vertebrate cells include, but are not limited to, a simian cell, COS cell (Gluzman, Y. (1981), Cell 23, 175-182, (ATCC CRL-1650)), mouse fibroblast cell NIH3T3 (ATCC No. CRL-1658), and a dihydrofolic acid reductase defective strain (Urlaub, G. and Chasin, L. A. (1980), Proc., Natl. Acad. Sci, USA 77, 4126-4220) of Chinese hamster ovary cell (CHO cell, (ATCC CCL-61)).

An expression promoter for use with a vertebrate cell, can be one having a promoter located upstream of the gene to be expressed, an RNA splicing site, a polyadenylation site, and a transcription termination sequence. Furthermore, a replication initiation site may be present. Examples of the suitable expression vectors include, but are not limited to, pCDNA3.1 (manufactured by Invitrogen) having an early promoter of a cytomegalo virus and pSV2dhfr (Subramani, S. et al., (1981), Mol. Cell. Biol. 1, 854-864) having an SV40 early promoter.

When using a COS cell or NIH3T3 cell as the host cell, suitable expression vectors have an SV40 replication initiation site, capable of self-proliferating in the COS cell or NIH3T3 cell and additionally may have a transcription promoter, transcription termination signal, and RNA splicing site. The expression vector may be integrated into the COS cell or NIH3T3 cell by DEAE-dextran treatment (Luthman, H and Magnusson, G. (1983), Nucleic Acids Res. 11, p. 1295-1308), calcium phosphate-DNA co-precipitation (Graham, F. L. and van der Eb, A. J. (1973), Virology, 52, p. 456-457), electroporation (Neumann, E. et al., (1982), EMBO J. 1, p. 841-845) or others. In this manner, a desired transformant cell can be obtained. Furthermore, when a CHO cell is used as a host cell, if a vector capable of expressing a neo gene functioning as an antibiotic G418 resistance marker, such as pRSVneo (Sambrook, J. et al., (1989): Molecular Cloning A Laboratory Manual "Cold Spring Harbor Laboratory, N.Y.) or pSV2neo (Southern, P. J., and Berg, P. (1982), J. Mol. Appl. Genet. 1, 327-341) is co-transfected with the expression vector, and then a G418 resistant colony is selected, a transformed cell stably producing the desired polypeptide can be obtained.

The transformant obtained in the manner mentioned above can be cultured in accordance with a customary method to obtain the desired polypeptide expressed within the cell or secreted outside the cell and thus present in the culture medium. As a culture medium, various types of media customarily used can be selected appropriately depending upon the type of host cell employed. More specifically, for COS cells, RPMI 1640 medium or Dulbecco's Modified Eagle's medium (hereinafter referred to as "DMEM") may be used. If necessary, serum components such as fetal calf serum may be added to the medium.

A recombinant protein produced within a cell or secreted outside a transformant cell and present in the culture medium can be separated and purified by various known separation methods on the basis of the physical properties and chemical properties of the protein. Examples of such separation methods include treatment with a general protein precipitating agent, ultrafiltration, molecular sieve chromatography (gel filtration), adsorption chromatography, ion-exchange chromatography, affinity chromatography, various types of liquid chromatographic methods such as high-performance liquid chromatography (HPLC), dialysis and combinations of these methods. If a hexa-his tag is fused to the recombination protein which is expressed, the recombinant protein can be efficiently purified by a nickel affinity column. If the aforementioned methods are used in combination, a large amount of a desired polypeptide can be obtained with a high purity and in a high yield.

(2) Production of Anti-Human Oculospanin Monoclonal Antibody

An example of an antibody which specifically binds to human oculospanin, is a monoclonal antibody which specifically binds to human oculospanin. A method suitable for obtaining such monoclonal antibody is as follows:

To produce the monoclonal antibody, the steps necessary required include:

(a) purifying the biomacromolecule which is to be used as an antigen;

(b) immunizing an animal by injecting the antigen into the animal, taking a blood sample and checking the antibody titer to determine the time at which the spleen should be excised, and preparing antibody producing cells;

(c) preparing bone myeloma cells (hereinafter referred to as "myeloma");

(d) fusing the antibody-producing cells and the myeloma;

(e) selecting hybridomas producing a desired antibody;

(f) segregating (cloning) them into single cell clones;

(g) optionally, culturing the hybridoma to produce a large amount of monoclonal antibody or raising an animal having the hybridoma transplanted therein; and (h) analyzing the physiological activity and binding specificity of the monoclonal antibody thus produced, or characteristics of the monoclonal antibody as a labeling agent.

The method of producing a monoclonal antibody is described in more detail below in accordance with the steps mentioned above. However, methods of producing monoclonal antibody are not limited to the method described. For example, an antibody-producing cell other than a spleen cell and myeloma.

(a) Purification of the Antigen

As the antigen, human oculospanin protein prepared according to the aforementioned method or a part (fragment) thereof can be used. Alternatively, the antigen used can be a membrane fraction prepared from a recombinant cell expressing human oculospanin or a recombinant cell expressing human oculospanin, or a chemically synthesized peptide fragment of a protein according to the present invention obtained by a method known to those skilled in the art.

(b) Preparation of an Antibody Producing Cell

An antigen obtained in step (a) is mixed with Freund's complete or incomplete adjuvant or an auxiliary agent such as potassium aluminum sulfate. The mixture is used as an immunogen and is injected into an animal. A suitable experimental animal would be an animal known to be suitable for use in a hybridoma preparation method. Specific examples of such animals include mice, rats, goats, sheep, cows and horses. However, in view of the availability of myeloma cells which are to be fused with the antibody-producing cells taken from the animal, mice or rats are preferred as the animals to be immunized. The choice of strains of mice or rats used in practice is not particularly limited. Examples of suitable mouse strains include A, AKR, BALB/c, BDP, BA, CE, C3H, 57BL, C57BR, C57L, DBA, FL HTH, HTI, LP, NZB, NZW, RF, R III, SJL, SWR, WB, and 129. Examples of rat strains include Low, Lewis, Spraque, Daweley, ACl, BN, and Fischer. These mice and rats are available from experimental animal-raising distributors such as Clea Japan Inc., Charles River Japan Inc., Japan SLC Inc., and The Jackson Laboratories. In view of fusion compatibility with myeloma cells as discussed later, "BALB/c" as a mouse line and "Low" as a rat line are particularly preferred as the immunized animal. In consideration of homology of an antigen between a human and a mouse, a mouse having a reduced biological function for removing autoantibody, in other words, a mouse suffering from autoimmune disease is preferably used. Note that a mouse or a rat which is to be immunized is preferably 5 to 12 weeks old, more preferably 6 to 8 weeks old.

An animal can be immunized with human oculospanin or a recombinantly produced version thereof by known methods, such as the methods specifically described in, for example, Weir, D. M. Handbook of Experimental Immunology Vol. I. II. III., Blackwell Scientific Publications, Oxford (1987), Kabat, E. A. and Mayer, M. M., Experimental Immunochemistry, Charles C Thomas Publisher Springfield Illinois (1964), etc. Of these immunization methods, a method preferably used in the present invention is, for example, performed as follows. First, an antigen, that is, a membrane protein fraction, or a cell expressing an antigen, is injected into an animal intradermally or intraperitoneally. To improve immunization efficiency, both injection methods can be used together. More specifically, when the intradermal injection is performed in the first half of the injections and the intraperitoneal injection is performed in the second half of the injections or only the last time, the immunization efficiency can be particularly increased. The dosing regimen of the antigen differs depending upon the type and individual differences, etc. of the animal body to be immunized. However, the antigen is preferably injected 3 to 6 times at intervals of 2 to 6 weeks, and more preferably 3 to 4 at intervals of 2 to 4 weeks. It is preferred not to excessively increase the number of dosings, because then the antigen may be wasted. Also, it is preferred not to overly extend the length of the dosing interval, because the activity of the cells decreases due to aging of the animal. The dose of the antigen differs depending upon the type and individual differences, etc. of the animal body; however, the dose generally falls within the range of about 0.05 to 5 ml, preferably about 0.1 to 0.5 ml. Booster immunization is performed 1 to 6 weeks after the antigen is administered, preferably after 2 to 4 weeks, more preferably after 2 to 3 weeks. If the booster immunization is performed after more than 6th weeks or within 1 week, the booster immunization will be less effective. Note that the dose of the antigen to be injected as a booster differs depending upon the type and size of the animal body; however, for example, for mice, it generally falls within the range of about 0.05 to 5 ml, preferably about 0.1 to 0.5 ml, and more preferably about 0.1 to 0.2 ml. It is preferable not to administer an unnecessarily large amount of antigen because then the immunization effect decreases and it is unfavorable to the animal to be immunized.

One to 10 days, preferably, 2 to 5 days, more preferably 2 to 3 days after the booster immunization, spleen cells or lymphocytes containing antibody-producing cells are removed from the immunized animal under aseptic conditions. At this time, an antibody titer is determined. If an animal having a sufficiently high antibody titer is used as the supply source for the antibody-producing cells, the efficiency of the following operations can be enhanced. As a method of determining the antibody titer to be used herein, various types of known technologies are appropriate, such as RIA methods, ELISA methods, fluorescent antibody methods, and passive blood cell agglutination reaction methods. In view of detection sensitivity, speed, accuracy, and the possibility of automatic operation, RIA methods and ELISA methods are preferred.

The determination of an antibody titer according to the present invention can be performed by an ELISA method as follows. First, the purified or partially purified antigen is adsorbed onto a solid surface such as 96-well plate for ELISA. Then, solid surface having no antigen adsorbed thereon is covered with a protein unrelated to the antigen, such as bovine serum albumin (hereinafter referred to as "BSA"). After washing the surface, the surface is brought into contact with a serially-diluted sample (e.g., mouse serum) serving as a primary antibody, thereby allowing a monoclonal antibody contained in the sample to bind to the antigen. Furthermore, a secondary antibody, that is, an enzyme-labeled antibody against a mouse antibody, is added to bind to the mouse antibody. After washing the resultant complex, a substrate for the enzyme is added and the change in absorbance, which occurs due to a colour change induced by degradation of the substrate, is measured to calculate the antibody titer.

Antibody-producing cells are separated from the spleen cells or lymphocytes in accordance with known methods (for example, described in Kohler et al., Nature, 256, 495, 1975; Kohler et al., Eur J. Immunol., 6, 511, 1977; Milstein et al., Nature, 266, 550, 1977; Walsh, Nature, 266, 495, 1977). More specifically, in the case of spleen cells, the antibody-producing cells can be separated by a general method which comprises homogenizing tissue, filtering the homogenized through a stainless steel mesh, and suspending the cells obtained in Eagle's Minimum Essential Medium (MEM).

(c) Preparation of Bone Myeloma Cells (Hereinafter Referred to as "Myeloma")

The choice of myeloma cells which are to be used for cell fusion is not particularly limited and suitable cells can be selected from known cell strains. For convenience when hybridoma are selected from fused cells, it is preferable to use a HGPRT (Hypoxanthine-guanine phosphoribosyl transferase) defective strain whose selection procedure has been established. More specifically, examples of HGPRT defective strains include X63-Ag8(X63), NS1-Ag4/1(NS1), P3X63-Ag8.U1(P3U1), X63-Ag8.653(X63.653), P2/0-Ag14(SP2/0), MPC11-45.6TG1.7(45.6TG), F0, S149/5XXO and BU.1 derived from mice, 210.RSY3.Ag.1.2.3 (Y3) derived from rat; and U266AR(SKO-007), GM1500·GTG-A12(GM1500), UC729-6, LICR-LOW-HMy2(HMy2), and 8226AR/N1P4-1(NP41) derived from humans. These HGPRT defective strains are available from the American Type Culture Collection (ATCC), etc.

These strains are subcultured in an appropriate medium such as 8-azaguanine medium [RPMI-1640 supplemented with glutamine, 2-mercaptoethanol, gentamicin, and fetal calf serum (hereinafter referred to as "FCS") and further 8-azaguanine is added thereto]; Iscove's Modified Dulbecco's Medium (hereinafter referred to as "IMDM"), or Dulbecco's Modified Eagle Medium (hereinafter referred to as "DMEM"). In this case, 3 to 4 days before performing the cell fusion operation, the cells are transferred to a regular medium [for example, ASF104 medium (manufactured by Ajinomoto Co. Inc.) containing 10% FCS] and subcultured therein to obtain not less than $2 \times 10^7$ cells by the day of cell fusion.

(d) Cell Fusion

Fusion between antibody-producing cells and myeloma cells is appropriately performed in accordance with known methods (including: Weir, D. M. Handbook of Experimental Immunology Vol. I. II. III., Blackwell Scientific Publications, Oxford (1987), Kabat, E. A., and Mayer, M. M. Experimental Immunochemistry, Charles C Thomas Publisher, Springfield, Ill. (1964)), under conditions such that the survival rate of cells is not excessively reduced. Examples of such methods include chemical methods in which antibody-producing cells and myeloma cells are mixed in a high concentration polymer solution, for example, polyethylene glycol; and physical methods using electric stimulation. Of these methods, the chemical method is more specifically explained as follows. When polyethylene glycol is used as the high concentration polymer solution, antibody-producing cells and myeloma cells are mixed in a solution of polyethylene glycol having a molecular weight of 1,500 to 6,000, more preferably, 2,000 to 4,000, at a temperature of 30 to 40° C., preferably 35 to 38° C., for 1 to 10 minutes, more preferably 5 to 8 minutes.

(e) Selection of Hybridoma Populations

The method of selecting hybridoma obtained by cell fusion is not particularly restricted. Usually, use is made of the HAT (hypoxanthine, aminopterin, thymidine) selection method [Kohler et al., Nature, 256, 495 (1975); Milstein at al., Nature 266, 550 (1977)]. This is an effective method when hybridoma are obtained using myeloma cells of a HGPRT defective strain incapable of surviving in the presence of aminopterin. More specifically, by culturing unfused cells and hybridoma in HAT medium, only hybridoma having aminopterin resistance are selected and allowed to remain and proliferate.

(f) Segregation to Single Cell Clone (Cloning)

As a cloning method for hybridoma, known methods such as a methylcellulose method, soft agarose method, or limiting dilution method can be used [see, for example, Barbara, B. M. and Stanley, M. S.: Selected Methods in Cellular Immunology, W. H. Freeman and Company, San Francisco (1980)]. Examples of a cloning method include a limiting dilution method in which hybridoma cells are diluted so as to contain a single hybridoma cell per well of a plate and cultured; a soft agarose method in which hybridoma cells are cultured in a soft agarose medium and colonies are recovered; a method of taking individual hybridoma cells by means of a micro manipulator and culturing them; and a so-called "clone sorter method" in which hybridoma cells are separated one by one by means of a cell sorter. Of these methods, the limiting dilution method is preferred. In this method, a fibroblast cell strain derived from a rat fetus or feeder cells such as healthy mouse spleen cells, thymus gland cells, or ascites cells are seeded. Hybridoma cells are diluted in medium to provide a dilution ratio of 0.2 to 0.5 cells per 0.2 ml. The diluted hybridoma suspension solution is transferred into wells to provide 0.1 ml per well and continuously cultured for about 2 weeks with changes of about ⅓ of the medium with fresh medium at predetermined time intervals (for example, every 3 days). In this manner, hybridoma clones can be proliferated.

The hybridoma cells in the well for which antibody titer has been confirmed are subjected to repeat cloning by the limiting dilution method, 2 to 4 times. Hybridoma cells, with an antibody titer which is confirmed to be stable, are selected as anti-human oculospanin monoclonal antibody producing hybridoma strains. One of the cloned hybridoma strains thus obtained is designated as "O3B8-2C9-4F3" and this has been deposited at the International Patent Organism Depositary of the National Institute of Advanced Industrial Science Technology (located at Tsukuba Central 6, 1-1-1 Higashi, Tsukuba, Ibaraki, Japan) as of Feb. 17, 2004 under deposition No. FERM BP-08627.

(g) Preparation of Monoclonal Antibody by Culturing Hybridoma Cells.

The hybridoma cells thus selected are cultured to efficiently obtain monoclonal antibody. However, prior to culturing, it is desirable that a hybridoma cell producing a desired monoclonal antibody is screened. The screening is performed by a known method.

The determination of antibody titer can be performed in the present invention by, for example, an ELISA method in accordance with the following procedure. First, purified or partially purified human oculospanin or cells expressing human oculospanin are adsorbed onto a solid surface of a 96-well plate for ELISA. Then, the solid surface having no antigen adsorbed thereon is covered with a protein unrelated to the antigen, for example, bovine serum albumin (hereinafter referred to as "BSA"). After washing the surface, the surface is brought into contact with a serially-diluted sample (for example, mouse serum) as a first antibody, thereby allowing binding of an anti-human oculospanin antibody in the sample to the antigen. Furthermore, an antibody against the mouse antibody and labeled with an enzyme, serving as a secondary antibody, is added to bind to the mouse antibody. After washing the resultant complex, a substrate for the enzyme is added and the change of absorbance, which occurs due to the colour change induced by degradation of the substrate, is determined to calculate the antibody titer. In this way, the antibody titer is calculated. Note that such a screening operation can be performed after or before cloning of the hybridoma cell as mentioned above.

A hybridoma obtained by the aforementioned method can be stored in a frozen state in liquid nitrogen or in a refrigerator at 80° C. or less.

After completion of cloning, hybridoma are transferred from HT medium to a general medium and cultured. Large-scale culture is performed by rotation culture using a large culture bottle or by spinner culture. The supernatant obtained from the large-scale culture is purified by a known method to those skilled in the art, such as gel filtration, to obtain a monoclonal antibody which specifically binds to a protein according to the present invention. The hybridoma can be injected into the abdominal cavity of a mouse of the same line as the hybridoma (for example, BALB/c) or a Nu/Nu mouse to proliferate the hybridoma. In this way, ascites fluid containing a large amount of the monoclonal antibody according to the present invention can be obtained. When hybridoma cells are injected into the abdominal cavity, if a mineral oil such as 2,6,10,14-tetramethyl pentadecane (pristine) has (3 to 7 days before) been administered previously, the ascites fluid can be obtained in a larger amount. To explain more specifically, an immunosuppressive agent is previously injected into the abdominal cavity of a mouse of the same strain as the hybridoma. Twenty days after inactivation of the T cells, $10^6$ to $10^7$ of hybridoma clone cells are suspended in a serum-free medium (0.5 ml) and the suspension is injected into the abdominal cavity. When the abdomen is expanded and filled with the ascites fluid, the ascites fluid is taken. By virtue of this method, the monoclonal antibody can be obtained at a concentration 100-fold higher than that of the culture medium.

A monoclonal antibody obtained in the aforementioned method can be purified by the methods described in, for example, Weir, D. M.: Handbook of Experimental Immunology Vol. I, II, III, Blackwell Scientific Publications, Oxford (1978). To explain more specifically, examples of such methods include ammonium sulfate precipitation methods, gel-filtration methods, ion exchange chromatographic methods, and affinity chromatographic methods. Of these, the ammonium sulfate precipitation method, if it is repeated 3 to 4 times, preferably 3 to 6 times, successfully purifies the monoclonal antibody. However, in this method, the yield of the purified monoclonal antibody is extremely low. Therefore, the monoclonal antibody is crudely purified by performing the ammonium sulfate precipitation method once or twice and then subjected to at least one method, and preferably two methods, selected from gel filtration, ion exchange chromatography, and affinity chromatography and the like. In this way, highly purified monoclonal antibody can be obtained in a high yield. The ammonium sulfate precipitation method may be performed in the following combination and in the following order: a) ammonium sulfate precipitation method—ion exchange chromatographic method-gel filtration method; b) ammonium sulfate precipitation method—ion exchange chromatographic method—affinity chromatographic method; and c) ammonium sulfate precipitation method—gel filtration method—affinity chromatographic method, etc. Of these combinations, to obtain the monoclonal antibody with a high purity in a high yield, combination c) is particularly preferable.

As a simple purification method, a commercially available antibody purification kit (for example, MAbTrap GII kit manufactured by Pharmacia) and the like can be used.

The monoclonal antibody thus obtained has high antigen specificity for human oculospanin.

(h) Analysis of Monoclonal Antibody

The monoclonal antibody thus obtained is checked for isotype and subclass thereof as follows. Suitable identification methods include the Ouchterlony method, ELISA methods and RIA methods. The Ouchterlony method is simple; although, if monoclonal antibody is obtained at low concentration it must be concentrated. Alternatively, when an ELISA method or RIA method is used, the culture supernatant can be directly reacted with an antigen adsorption solid phase. In addition, if various types of antibodies corresponding to immunoglobulin isotypes and subclasses are used as secondary antibodies, the isotype and subclass of the monoclonal antibody can be identified. As a further simple method, a commercially available identification kit (for example, Mouse Typer kit manufactured by BioRad) and the like can be used.

The quantification of a protein can be performed by the Folin Lowry assay based on the adsorption at 280 nm [1.4 (OD280)=Immunoglobulin 1 mg/ml].

(3) Preparation of Humanized Anti-Human Oculospanin Antibody

Immunoglobulin G (hereinafter simply referred to as "IgG") consists of two light polypeptide chains (hereinafter referred to as "light chains") each having a molecular weight of about 23,000 and two heavy chains (hereinafter referred to as "heavy chains") each having a molecular weight of about 50,000. Each of the heavy chains and light chains has a repeat structure, in which an amino acid sequence formed of about 110 residues are conserved, this constitutes a basic unit (hereinafter referred to as a "domain") of the three dimensional structure of IgG. The heavy chain and light chain constitute 4 and 2 independent continuous domains, respectively. In both the heavy chain and the light chain, the variation in the amino terminal domain between different antibodies is greater than the variation in the other domains. This domain is called a variable domain (hereinafter referred to as a "V domain"). At the amino terminus of IgG, the V domains of the heavy chain and light chain are complementarily associated to form a variable region. In contrast, the remaining domains constitute a constant domain. The constant domain has a sequence intrinsic to each animal species. For example, the constant region of mouse IgG differs from that of human IgG. Therefore, mouse IgG is recognized as a foreign substance by the human immune system. As a result, a human anti-mouse antibody response (hereinafter referred to as "HAMA") is raised (see Schroff et al., Cancer Res., 45, 879-85 (1985). Because of this, mouse antibody cannot be administered repeatedly to a human subject. To administer such an antibody to a human, it is necessary to modify the antibody molecules so as not to cause the HAMA response whilst maintaining the specificity of the antibody.

According to the results of X-ray crystallography, a domain has a longitudinal cylindrical structure in which two layers of antiparallel β-sheets each formed of 3 to 5 β chains are superposed. In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. The portions other than the CDRs of the variable region generally play a role in supporting the structure of the CDR, and are thus called the "framework". Kabat et al. collected numerous primary sequences of the variable regions of heavy chains and light chains. Based on the degree of conservation of the sequences, they classified individual primary sequences into the CDR and the framework and made a list thereof (see SEQUENCES OF IMMUNOLOGICAL INTEREST, 5th edition, N1H publication, No. 91-3242, E. A. Kabat et al.). Furthermore, the frameworks are classified into a plurality of subgroups based on common features of the amino acid sequences. Furthermore, it was found that there is a corresponding framework between a human and a mouse.

From studies of the structural features of IgG, a method of preparing a humanized antibody has been conceived as described below.

Initially, a chimeric antibody was proposed in which the variable region of an antibody derived from a mouse is connected to a constant region derived from a human (see Proc. Natl. Acad. Sci. U.S.A. 81, 6851-6855, (1984)). However, such a chimeric antibody still contains many non-human amino acid residues. Therefore, when the chimeric antibody is administered over a long period of time, a HAMA response may possibly be induced (see Begent et al., Br. J. Cancer, 62, 487, (1990)).

As a method for further reducing the amino acid residues derived from a non-human mammalian source, which may possibly cause a HAMA response in humans, a method of integrating only the CDR portion into a human-derived antibody was proposed (see Nature, 321, 522-525, (1986)). However, to maintain immunoglobulin activity against an antigen, transplantation of the CDR alone was generally insufficient.

Chothia et al., found the following based on data obtained by X-ray crystallography in 1987: (i) in the amino acid sequence of the CDR, there is a site which binds directly to an antigen and a site responsible for maintaining the structure of the CDR itself, and the three dimensional structures of the CDR that can be adopted are classified into a plurality of typical patterns (canonical structures); and (ii) the classes of canonical structures are determined not only by the CDR, but also by the type of amino acid present in a specific site of the framework portion (see J. Mol. Biol., 196, 901-917, (1987)).

Based on these findings, it was suggested that when the CDR transplantation method is employed, amino acid residues of a part of the framework must be transplanted into a human antibody in addition to the sequence of the CDR (see Japanese National Publication of International Patent Application No. 4-502408).

Generally, a non-human mammalian-derived antibody from which the CDR is to be transplanted is defined as a "donor", whereas the human antibody into which the CDR is transplanted is defined as an "acceptor". The present invention follows these definitions.

A point which should be considered in carrying out the CDR transplantation is that the activity of the immunoglobulin molecule is maintained by preserving the CDR structure as much as possible. To achieve this, attention must be paid to the following two points:

(i) which subgroup of antibodies the acceptor is selected from; and (ii) which amino acid residue is selected from the framework of the donor.

Queen et al. proposed a design method for transplanting an amino acid residue into an acceptor together with the CDR sequence when the amino acid residue of the framework of the donor corresponds to at least one of the following references (see Japanese National Publication of International Patent Application No. 4-502408).

(a) the amino acid is rarely present at the position within the framework of an acceptor, whereas the corresponding amino acid of a donor is usually present at the equivalent position;

(b) the amino acid is present near one of the CDRs; and (c) it is predicted that the amino acid has a side chain atom within about 3 angstroms from the CDR in its three dimensional immunoglobulin model and that the side main atom can interact with an antigen or the CDR of a humanized antibody.

DNA encoding a heavy chain or light chain of the anti human oculospanin monoclonal antibody of the present invention can be obtained by preparing mRNA from a hybridoma cell producing the anti-human oculospanin monoclonal antibody, converting the mRNA into cDNA using reverse transcriptase, and isolating each DNA encoding the heavy chain or light chain of the antibody.

In extracting mRNA, the guanidine thiocyanate—hot phenol method, and guanidine thiocyanate guanidine—hydrochloride method may be employed; however, the guanidine thiocyanate cesium chloride method is also suitable. Preparation of mRNA from a cell is performed by first preparing total RNA and purifying the mRNA using a poly(a)$^+$ RNA purification carrier such as oligo (dT) cellulose or oligo (dT) latex beads or directly purifying mRNA from a cell lysate by use of the carrier. For preparing total RNA, use may be made of the alkaline sucrose density-gradient centrifugation method [see Dougherty, W. G. and Hiebert, E. (1980) Virology 101, 466-474], the guanidine thiocyanate-phenol method, the guanidine thiocyanate-trifluoro-cesium method, and the phenol SDS method and the like; however, the method using guanidine thiocyanate and cesium chloride is also suitable [see Chirgwin, J. M., et al. (1979) Biochemistry 18, 5294-5299].

After a single-stranded cDNA is synthesized by a reverse transcriptase reaction using the poly(a)$^+$ RNA obtained as mentioned above as a template, double-stranded cDNA can be synthesized from the single-stranded cDNA. This method may be the S1 nuclease method [see Efstratiadis, A., et al. (1976) Cell, 7, 279-288], the Gubler/Hoffmann method [see Gubler, U. and Hoffman, B. J. (1983) Gene 25, 263-269], the Okayama/Berg method [see Okayama, H. and Berg, P. (1982) Mol. Cell. Biol. 2, 161-170] or others; however, suitably used in the present invention is the so-called RT-PCR method in which a polymerase chain reaction (hereinafter referred to as a "PCR") [see Saiki, R. K., et al. (1988) Science 239, 487-49] is performed using a single-stranded cDNA as a template.

The double-stranded cDNA thus obtained is integrated into a cloning vector to obtain a recombinant vector, which is then introduced into a microorganism, such as *Escherichia coli*, to form a transformant. The transformant can be selected by using tetracycline resistance or ampicillin resistance as a marker. *Escherichia coli* can be transformed by the Hanahan method [see Hanahan, D. (1983) J. Mol. Biol. 166, 557-580], more specifically, by preparing a competent cell in the presence of calcium chloride, magnesium chloride or rubidium chloride, and adding the recombinant DNA vector to the competent cell. Note that when a plasmid is used as a vector, the plasmid must have any one of the drug resistance genes as mentioned above. Needless to say, a cloning vector other than a plasmid, such as a lambda group phage, may be used.

As a method of selecting a strain having a cDNA, which encodes each of the subunits of a desired anti-human oculospanin monoclonal antibody from the transformant strain obtained above, any of the methods described below can be employed. When a desired cDNA is specifically amplified by the RT-PCR method, such operation of the method can be skipped.

(a) Method Using a Polymerase Chain Reaction

When the amino acid sequence of a desired protein has been elucidated in its entirety or in part, oligonucleotide primers of a sense strand and an antisense strand corresponding to a part of the amino acid sequence are synthesized. Then, the polymerase chain reaction [Saiki, R. K., et al. (1988) Science 239, 487-49] is preformed by using these primers in combination to amplify a DNA fragment encoding heavy chain and light chain subunits of a desired anti-human oculospanin antibody. As the template DNA used herein, use may be made of cDNA synthesized from mRNA of a hybridoma producing the anti-human oculospanin monoclonal antibody by a reverse transcriptase reaction.

The DNA fragment thus prepared can be directly integrated into a plasmid vector by use of a commercially available kit, etc. Alternatively, the DNA fragment may be used for selecting a desired clone by labeling the fragment with $^{32}$P, $^{35}$S, or biotin, and performing colony hybridization or plaque hybridization by using it as a probe.

For example, a method of examining a partial amino acid sequence of each subunit of the anti-human oculospanin monoclonal antibody of the present invention is preferably performed by isolating each subunit by use of a known method such as electrophoresis or column chromatography and then analyzing the N-terminal amino acid sequence of each subunit using an automatic protein sequencer (for example, PPSQ-10, manufactured by Shimadzu Corporation).

A method of isolating cDNA encoding each subunit of the anti-human oculospanin monoclonal antibody protein from the desired transformant obtained as mentioned above is performed in accordance with a known method [see Maniatis, T., et al. (1982) in "Molecular Cloning A Laboratory Manual" Cold Spring Harbor Laboratory, N.Y.], and more specifically, can be performed by separating fractions corresponding to vector DNA from a cell and excising a DNA region encoding a desired subunit from the vector DNA (plasmid DNA).

(b) Screening Method Using a Synthesized Oligonucleotide Probe

When the whole or part of the amino acid sequence of a desired protein is elucidated (any sequence is taken from any region of the desired protein as long as it is a specific sequence having a plurality of contiguous amino acids), an oligonucleotide is synthesized (in this case, use may be made of either a nucleotide sequence presumed based on the degree of frequency of codons in use or a plurality of nucleotide sequences of conceivable nucleotide sequences in combination; in the latter case, the number of types of nucleotide sequences can be reduced by integrating inosine) so as to correspond to the amino acid sequence, used as a probe (labeled with $^{32}$P, $^{35}$S or biotin); hybridized with a nitrocellulose filter on which the DNA of a transformant strain is denatured and immobilized, and then the positive strain obtained is isolated.

The sequence of the DNA thus obtained can be determined by the Maxam—Gilbert chemical modification method [see Maxam, A. M. and Gilbert, W. (1980) in "Methods in Enzymology" 65, 499-576] and the dideoxynucleotide chain termination method [Messing, J. and Vieira, J. (1982) Gene 19, 269-276].

Recently, an automatic base sequence determination system using a fluorescent dye has been widely used (for example, sequence robots "CATALYST 800" and model 373ADNA sequencer, etc. manufactured by PerkinElmer Japan Co., Ltd.)

Using such a system also makes it possible to efficiently and safely determine a DNA nucleotide sequence. Based on the data of the present invention thus determined including the nucleotide sequence of DNA and the N-terminal amino acid sequences of the heavy chain and light chain, it is possible to determine the entire amino acid sequence of the heavy chain and light chain of the monoclonal antibody of the present invention.

The heavy chain and light chain of immunoglobulin each constitute a variable region and a constant region. The variable region further constitutes complementarity-determining regions (hereinafter referred to as "CDR", there are 3 sites in each of the heavy chain and light chain) and framework regions adjacent to these CDRs (4 sites in each of the heavy chain and light chain).

The amino acid sequence of the constant region is common to antibodies belonging to the same immunoglobulin class regardless of the type of antigen. In the variable region, the amino acid sequence of a CDR is intrinsic to each antibody. However, according to a study comparing amino acid sequence data of numerous antibodies, it is known that the position of the CDR and the length of a framework sequence are similar between the subunits of different antibodies as long as they belong to the same subgroup [see Kabat, E. A., et al. (1991) in "Sequence of Proteins of Immunological Interest Vol. II": U.S. Department of Health and Human Services]. Therefore, it is possible to determine the position of the CDRs and framework regions and further the constant region in each amino acid sequence, by comparing the amino acid sequences of the heavy chain and the light chain of the anti-human oculospanin monoclonal antibody of the present invention with the known amino acid sequence data. Note that the chain length of $FRH_1$, that is, the framework region located at the side proximal to the N terminus, is sometimes shorter than the general length of 30 amino acids. In some cases, the framework region is known to have a minimum of 18 amino acids [see Kabat et al. cited above]. From this, in the antibody of the present invention, the chain length of the framework region at the N-terminus of the heavy chain is set at 18 to 30 amino acids, preferably 30 amino acids, as long as the function of the anti human oculospanin antibody is not impaired.

In summary, only by artificially modifying a peptide having the same amino acid sequence as each of the CDRs of light chains or heavy chains or a partial contiguous amino acid sequence thereof, as determined above, thereby approximating the structure to the tertiary structure of the CDR actually taken from within the anti-human oculospanin antibody molecule, a binding activity capable of binding to human oculospanin can be imparted to the CDR [see, for example, U.S. Pat. No. 5,331,573]. Hence, a peptide containing the same amino acid sequence as that of a CDR or a partial amino acid sequence thereof is also included as being a molecule of the present invention.

A modified amino acid sequence can be prepared by deleting at least one or more amino acids from its original amino acid sequence in accordance with cassette mutagenesis [see Toshimitu Kishimoto, "New Biochemical Experimental Lecture 2, Nucleic acid III, Recombinant DNA technique", p 242-251].

Such various types of DNA sequences can be produced in accordance with a customary method for chemically synthesizing a nucleic acid, for example, the phosphite triester method [see Hunkapiller, M., et al. (1984) Nature 310, 105-111]. Note that codons corresponding to a desired amino acid are already known per se. Any codon may be selected. Alternatively, which codon is used can be determined in accordance with a customary method by considering the frequency with which codons are used by the host cell. The partial modification of the nucleotide sequences of codons, may be performed in accordance with a customary method, more specifically, in accordance with a site-specific mutagenesis method [see Mark, D. F., et al. (1984) Proc. Natl. Acad. Sci. USA 81, 5662-5666] using a synthetic oligonucleotide primer encoding a desired modification.

Furthermore, it is possible to check whether a certain type of DNA can hybridize with DNA encoding a heavy chain or light chain of an anti-human oculospanin monoclonal antibody of the present invention by subjecting the DNA to the following experiment performed using a probe DNA labeled with $[\alpha\text{-}^{32}P]dCTP$, in accordance with the random primer method [see Feinberg, A. P. and Vogelstein, B. (1983) Anal. Biochem. 132, 6-13] or the nick translation method [see Maniatis, T., et al. (1982) in "Molecular Cloning A laboratory Manual" Cold Spring Harbor Laboratory, NY].

To explain more specifically, the DNA to be checked is adsorbed onto, for example, a nitrocellulose or nylon membrane. After it is denatured with alkali, if necessary, the membrane is heated or UV-irradiated, thereby immobilizing the DNA onto the membrane. The membrane is soaked in a pre-hybridization solution containing 6×SSC (1×SSC contains 0.15M sodium chloride, 0.015 trisodium citrate solution) and 5% Denhardt's solution, and 0.1% sodium dodecylsulfate (SDS), and maintained at 55° C. for 4 hours or more. Subsequently, the probe prepared in advance is added to the pre-hybridization solution so as to have a final specific activity of $1 \times 10^6$ cpm/ml and the temperature is maintained at 60° C. overnight. Thereafter, the membrane is washed with 6×SSC at room temperature for 5 minutes several times, further washed with 2×SSC for 20 minutes and subjected to autoradiography.

Using the aforementioned methods, DNA which hybridizes with the DNA encoding a heavy chain or light chain of the humanized anti-human oculospanin antibody of the present invention can be isolated from a random cDNA library or a genomic library [see Maniatis, T., et al. (1982) in "Molecular Cloning A Laboratory Manual" Cold Spring Harbor Laboratory, NY].

Each of the DNA sequences obtained in the aforementioned manner can be integrated into an expression vector, which can be then introduced into a prokaryotic or eukaryotic host cell. In this way, the gene (having the DNA) can be expressed in the host cell. The expression method is the same as the method described in Section "5. Preparation of anti-human oculospanin antibody", Paragraph "(1) Preparation of antigen" set forth above.

A fraction containing an anti-human oculospanin antibody protein produced within or outside the transformant cell can be treated by various known protein isolation procedures based on the use of physical and/or chemical properties to isolate and purify the protein. Examples of these methods include treatment with a protein precipitation agent generally used, ultrafiltration, chromatography, such as molecular sieve chromatography (gel filtration), adsorption chromatography, ion-exchange chromatography, and affinity chromatography, or high performance liquid chromatography (HPLC), dialysis, and combinations thereof.

To humanize the anti-human oculospanin monoclonal antibody, the amino acid sequence of a variable region must be designed such that the entire CDR sequence and a partial amino acid sequence of the FR sequence determined are transplanted into a human antibody framework, as follows:

Conventionally, in designing a humanized antibody, an acceptor subgroup is selected based on the following guidelines.

a) the natural combination of a heavy chain and light chain of a known human antibody having a naturally occurring amino acid sequence is used as it is;

b) although the combination of a heavy chain and a light chain as a subgroup is maintained; the heavy chain and the light chain may be derived from different human antibodies. The heavy chain and the light chain which are to be used may be selected from amino acid sequences with high identity to those of the heavy chain and light chain of the donor, respectively, and the consensus sequences. In the present invention, the aforementioned guidelines may be employed. However, there are alternative methods as follows:

c) regardless of consideration of the combination of the subgroup, a method may be employed for selecting FRs of the heavy chain and light chain with high identity to those of a donor from the library of primary sequences of a human antibody. In these selection methods, the degree of identity of the amino acids of the FR region between a donor and an acceptor can be set at 70% or more. By employing such a method, it is possible to reduce the number of amino acid residues of an antibody to be transplanted from a donor, thereby inducing less HAMA response.

There is an operation (hereinafter referred to as "molecular modeling") for predicting the tertiary structure of an antibody molecule from its primary sequence; however, the accuracy of prediction of this operation is limited. Therefore, the role of an amino acid residue appearing only rarely in the subgroup to which the donor belongs cannot be sufficiently specified. It is generally difficult to determine which amino acid residue of a donor or an acceptor should be selected for such a position of the amino acid residue in accordance with the method described above by Queen and co-workers. However, in accordance with the selection method (c), it is possible to reduce the frequency with which such determination must be made.

The present inventors have further improved such humanization methods by providing a novel method of identifying an amino acid derived from the FR of a donor and important for maintaining the structure and function of a CDR of the donor.

After a human acceptor molecule for each of a light chain and heavy chain is selected, the amino acid residue to be transferred from the FR of a donor is selected by the method mentioned below.

In the amino acid sequences of the donor and the acceptor, when the corresponding amino acid residues of their FRs differ from each other, it must be determined which amino acid residue should be selected. When making such a selection, care must be taken so as not to damage the tertiary structure of the CDR derived from the donor.

Queen et al. have proposed, in the Japanese National Publication of International Patent Application No. 4-502408, a method of transplanting an amino acid residue on the FR into an acceptor together with a CDR sequence, if it satisfies at least one of the following conditions,.

1) The amino acid is rarely present at the position within a human FR region of an acceptor, whereas the corresponding amino acid of a donor is usually present at the equivalent position;

2) the amino acid is located extremely close to one of the CDRs;

3) it is predicted that the amino acid has a side chain atom within about 3 angstroms from the CDR in its three dimensional immunoglobulin model and the side chain atom can interact with an antigen or the CDR of a humanized antibody.

In the above, a residue satisfying requirement 2) above often exhibits the property of requirement 3). Therefore, in the present invention, requirement 2) is omitted and two requirements are newly set. More specifically, in the present invention, if the amino acid residue on the donor's FR to be transferred together with the CDR satisfies the following:

a) the amino acid is rarely present at the position within an FR region of an acceptor, whereas the corresponding amino acid of a donor is usually present at the equivalent position;

b) in the tertiary structure model, the amino acid presumably interacts with a constituent amino acid atom of the CDR and an antigen or the CDR loop to be transplanted;

c) the position mentioned above is that of a canonical class determination residue; or d) the position is that which forms a contact surface between a heavy chain and a light chain, then the amino acid residue is transplanted from the FR of the donor.

In requirement a), in accordance with the Kabat list mentioned above, an amino acid found at a frequency of 90% or more at a position in the same subclass of antibody is defined as "usually present", whereas an amino acid found at a frequency of less than 10% is defined as "rarely present".

In requirement c), as to whether or not "the position mentioned above is a canonical class determining residue", the determination can be made uniquely in accordance with Chothia's list as mentioned above.

In requirements b) and d), molecular modeling of the antibody's variable region must be performed in advance. As software for molecular modeling, any commercially available software may be used; however, preferably AbM (manufactured by Oxford Molecular Limited Company) is used.

The accuracy of prediction by molecular modeling is somewhat limited. Therefore, in the present invention, by considering X-ray crystallographic data for variable regions of various antibodies, the reliability of the structure predicted by molecular modeling can be evaluated in two steps.

In the tertiary structure of the variable region constructed by the molecular modeling software, such as AbM, if the distance between two atoms is shorter than a value of the sum of the van der Waals radius of two atoms plus 0.5 angstroms, the two molecules are assumed to be in van der Waals contact. On the other hand, if the distance between atoms having polarity, such as amide nitrogen or carbonyl oxygen, of the main and side chains, is shorter than a distance of an average hydrogen binding distance, 2.9 angstroms plus 0.5 angstroms, it is assumed that hydrogen bonding may exist between the atoms. Furthermore, if the distance between the oppositely charged atoms is shorter than a distance of 2.85 angstroms plus 0.5 angstroms, it is assumed that an ionic bond is formed between the atoms.

On the other hand, from X-ray crystallographic experimental results for variable regions of various antibodies, as the position on the FR at which contact with the CDR can be found with a high frequency regardless of the subgroup, the following positions can be specified: in the light chain, the 1, 2, 3, 4, 5, 23, 35, 36, 46, 48, 49, 58, 69, 71, and 88th positions, and in the heavy chain, 2, 4, 27, 28, 29, 30, 36, 38, 46, 47, 48, 49, 66, 67, 69, 71, 73, 78, 92, 93, 94, and 103rd positions (numerals all represent amino acid numbers defined in the documents described by Kabat et al. The same definition will be also applied below). When the same standard as that of the molecular modeling is applied, the amino acid residues of these positions are confirmed to be in contact with the amino acid residues of the CDR in the $2/3$ portion of the known antibody's variable region. Based on the findings, the sentence: "b) In the tertiary structure model, the amino acid presumably interacts with a constituent amino acid atom of the CDR and an antigen or the CDR loop to be transplanted" means as follows.

In molecular modeling, if a position in the FR which is expected to be in contact with the CDR agrees with any one of the positions at which the contact between the FR and the CDR is reported to frequently occur according to experimental detection by X-ray crystallography, selection of the amino acid residue from, the donor is preferred. In other cases, requirement b) is not taken into consideration.

The sentence: "d) the position is that which forms a contact surface between the heavy chain and the light chain" means the following requirement. From the X-ray crystallographic experimental results for the variable regions of various antibodies, it is confirmed that heavy chain-light chain contact is frequently observed at the 36, 38, 43, 44, 46, 49, 87, 98th amino acid residues in the light chain and at the 37, 39, 45, 47, 91, 103, and 104th amino acid residues in the heavy chain. In cases where the possibility of heavy chain-light chain contact is predicted in the molecule modeling and the contact position agrees with any one of the aforementioned positions, transplantation of the amino acid residue from the donor is preferably performed. In other cases, requirement d) is not taken into consideration.

The DNA encoding variable regions of the heavy chain and light chain of a humanized anti-human oculospanin antibody of the present invention can be produced by the methods described below.

For example, a plurality of polynucleotide fragments comprising a partial nucleotide sequence of the DNA, of 60 to 70 nucleotides in length, are chemically synthesized alternately from the sense and antisense strands. Thereafter, individual polynucleotide fragments are annealed and ligated using DNA ligase. In this way, it is possible to obtain a DNA having DNA encoding variable regions of the heavy chain and light chain of a desired humanized anti-human oculospanin antibody.

In another method, DNA encoding the total amino acid sequence of the variable region of an acceptor is extracted from human lymphocytes, replacement of nucleotides is performed in the region encoding a CDR by a method known to those skilled in the art to introduce a restriction enzyme cleavage sequence. After the region is cleaved with the corresponding restriction enzyme, the nucleotide sequence encoding a CDR of the donor is synthesized and ligated using DNA ligase. In this way, it is possible to obtain the DNA encoding variable regions of the heavy chain and light chain of a desired humanized anti-human oculospanin antibody.

Furthermore, in the present invention, it is possible to obtain DNA comprising DNA encoding variable regions of the heavy chain and light chain of a desired humanized anti-human oculospanin antibody, preferably in accordance with the overlap extension PCR method (Horton et al., Gene, 77, 61-68, (1989)) described below.

To explain more specifically, two different DNA sequences, which encode two different amino acid sequences, respectively and which are desired to be ligated to each other, are designated as (A) and (B), for the sake of convenience. A sense primer of 20 to 40 nucleotides (hereinafter referred to as a "primer (C)") to be annealed to the 5' side of the DNA sequence (A) and an antisense primer of 20 to 40 nucleotides (hereinafter referred to as a "primer (D)") to be annealed to the 3' side of the DNA sequence (B) are chemically synthesized. Furthermore, a chimeric-type sense primer (hereinafter referred to as "primer (E)) is formed by ligating a nucleotide sequence of 20 to 30 nucleotides to the 3' side of the DNA sequence (A) and a nucleotide sequence of 20 to 30 nucleotides is ligated to the 5' side of the DNA sequence (B). An antisense primer (hereinafter referred to as "primer (F)) complementary to the primer (E) is synthesized. When a PCR is performed by using appropriate vector DNA containing DNA (A) as a substrate, sense primer (C) and the chimeric-type antisense primer (F), DNA in which the 20 to 30 nucleotides of the 5' end of DNA (B) is attached to the 3' end of the DNA (A) can be obtained (the DNA newly formed is designated as DNA (G)). Similarly, when a PCR is performed by using appropriate vector DNA containing DNA (B) as a substrate, antisense primer (D) and the chimeric-type sense primer (E), DNA in which 20 to 30 nucleotides of the 3' end of DNA (A) is attached to the 5' end of the DNA (B) can be obtained (the DNA newly formed is designated as DNA (H)). In the DNAs (G) and (H), the 40 to 60 nucleotides on the 3' side of the DNA (G) form a sequence complementary to that formed by the 40 to 60 nucleotides on the 5' side of the DNA (H). The amplified DNA (G) and (H) are mixed and subjected to PCR, DNA (G) and (H) are formed into a single strand in a first denaturation reaction. Although most chains of DNA revert to their original states following an annealing reaction, a part of DNA forms into a hetero-double-stranded DNA by the annealing of the complementary nucleotide sequence region. A protruding single stranded part is filled in by a subsequent extension reaction to obtain a chimeric type DNA (hereinafter referred to as DNA (I)) formed of DNA (A) and DNA (B) ligated to each other. DNA (I) can be amplified by performing PCR using DNA (I) as a substrate, the sense primer (C) and the antisense primer (D). In the present invention, DNA encoding a CDR region of a heavy chain and light chain of an anti-human oculospanin mouse monoclonal antibody, DNA encoding an FR region of human immunoglobulin IgG, furthermore DNA encoding a secretion signal of human immunoglobulin IgG may be used as DNA (A) and (B), on a case-by-case basis, and subjected to the ligation reaction mentioned above.

Note that codons corresponding to a desired amino acid are known per se and can be arbitrarily chosen. More specifically, the codons can be determined in accordance with a customary method in consideration of the frequency with which the codon is used by a host. A part of nucleotide sequence of the codons may be modified in accordance with a customary method such as site-specific mutagenesis (see, Mark, D. F., et al. (1984) Proc. Natl. Acad. Sci. USA 81, 5662-5666) using a synthetic oligonucleotide primer encoding a desired modification. Therefore, if each primer is designed so as to introduce a point mutation and thereafter chemically synthesized, it is possible to obtain DNA encoding variable regions of a heavy chain and light chain of a desired anti-human oculospanin antibody.

By integrating each of the DNAs of the present invention thus obtained into an expression vector, a prokaryotic or eukaryotic host cell can be transformed. Furthermore, by introducing an appropriate promoter and a sequence related to phenotypic expression into these vectors, each gene can be expressed in the corresponding host cell.

By virtue of the method mentioned above, a recombinant anti-human oculospanin antibody can be manufactured easily with high purity and in high yield.

(4) Preparation of Anti-Human Oculospanin Complete Human Antibody

The complete human antibody refers to a human antibody having only the gene sequence of an antibody derived from a human chromosome. The anti-human oculospanin complete human antibody can be obtained by a method using a human antibody-producing mouse having a human chromosome fragment containing the genes for a heavy chain and light chain of a human antibody [see Tomizuka, K. et al., Nature Genetics, 16, p. 133-143, 1997; Kuroiwa, Y. et al., Nuc. Acids Res., 26, p. 3447-3448, 1998; Yoshida, H. et al., Animal Cell Technology: Basic and Applied Aspects vol. 10, p. 69-73 (Kitagawa, Y., Matuda, T. and Iijima, S. eds.), Kluwer Academic Publishers, 1999; Tomizuka, K. et al., Proc. Natl. Acad. Sci. USA, 97, 722-727, 2000, etc.] or obtained by a method for obtaining a human antibody derived from a phage display selected from a human antibody library [see Wormstone, I. M. et al., Investigative Ophthalmology & Visual Science. 43(7), p. 2301-8, 2002; Carmen, S. et al., Briefings in Functional Genomics and Proteomics, 1 (2), p. 189-203, 2002; Siriwardena, D. et al., Ophthalmology, 109(3), p. 427-431, 2002, etc.]

As a method of confirming whether or not the recombinant anti-human oculospanin antibody thus prepared specifically binds to human oculospanin, the ELISA method used in evaluating the antibody titer of an immunized mouse is suitably employed.

6. A Pharmaceutical Composition Containing an Anti-Human Oculospanin Antibody

From the anti-human oculospanin antibodies obtained by a method described in Section "5. Preparation of anti-human oculospanin antibody", antibody neutralizing the biological activity of human oculospanin or an antibody specifically damaging a cancer cell expressing human oculospanin can be obtained. These antibodies can inhibit the biological activity of human oculospanin in the living body, in other words, canceration of a cell. Therefore, they can be used as a medicament, in particular, as a therapeutic agent for cancer. The activity of an anti-human oculospanin antibody in neutralizing a biological activity of human oculospanin in vitro can be determined by the ability to inhibit canceration of a cell in which human oculospanin is overexpressed. To explain more specifically, the inhibitory activity can be determined by culturing mouse fibroblast cell strain, NIH3T3, which overexpresses human oculospanin, adding an anti-human oculospanin antibody to the culture system in various concentrations. In this way, the inhibitory activities against focus formation, colony formation and spheroid growth can be determined. The cytotoxic activity of an anti-human oculospanin antibody against a cancer cell in vitro can be determined by antibody-dependent cytotoxic activity, complement-dependent cytotoxicity or complement-dependent cell-mediated cytotoxicity exhibited by the anti-human oculospanin antibody against a cell overexpressing human oculospanin. To be more specific, 293T cells overexpressing human oculospanin are cultured; then, an anti-human oculospanin antibody is added at various concentrations to the culture system. Mouse spleen cells are further added to the culture system and cultured for an appropriate time. Thereafter, the ratio of induction of cell death for the cells overexpressing human oculospanin is determined. The effect of an anti-human oculospanin antibody in cancer treatment can be determined in vivo by using an experimental animal, more specifically, by administering the anti-human oculospanin antibody to a transgenic animal overexpressing human oculospanin and determining a change in the cancer cells.

An antibody thus obtained for neutralizing the biological activity of human oculospanin or an antibody specifically damaging cancer cells expressing human oculospanin is useful as a medicament, especially as a pharmaceutical composition for use in cancer treatment or as an antibody for use in immunological diagnosis of such a disease. As the type of cancer, skin cancer and melanoma, a kind of skin cancer, may be mentioned; but cancers that can be treated or diagnosed in accordance with the invention are not limited to these examples.

The present invention provides a pharmaceutical composition containing an anti-human oculospanin antibody in an amount useful for treatment, a pharmaceutically acceptable diluent, carrier, solubilizer, emulsifier, preservative and/or an auxiliary agent.

A substance to be used as a pharmaceutically acceptable preparation in a pharmaceutical composition according to the present invention is preferably non-toxic to a patient to which the pharmaceutical composition is to be administered, in view of the dose and concentration.

A pharmaceutical composition according to the present invention can contain substances, suitable for inclusion in a preparation, which are capable of changing, maintaining, and stabilizing pH, osmotic pressure, viscosity, transparency, isotonic condition, aseptic condition, stability, solubility, release rate, absorbtion rate, and permeability. Examples of such substances for inclusion in a preparation include, but are not limited to, amino acids such as glycine, alanine, glutamine, asparagine, arginine, and lysine; antioxidant agents such as anti-bacterial agents, ascorbic acid, sodium sulfate and sodium hydrogen sulfite; buffering agents such as phosphate, citrate, borate buffers, hydrocarbonate, Tris-HCl solution; fillers such as mannitol and glycine; chelating agents such as ethylenediamine tetraacetate (EDTA); complex forming agents such as caffeine, polyvinylpyrrolidine, β-cyclodextrin and hydroxypropyl-β-cyclodextrin; thickening agents such as glucose, mannose, and dextrin; carbohydrates such as monosaccharides, disaccharides, glucose, mannose, dextrin; hydrophilic polymers such as colorants, flavors, diluents, emulsifiers, polyvinylpyrrolidine; preservatives such as low molecular weight polypeptides, base-forming counter ions, benzalkonium chloride, benzoate, salicylic acid, thimerosal, phenethyl alcohol, methylparaben, propylparaben, chlorhexidine, sorbic acid, and hydrogen peroxide; solvents such as glycerin, propylene glycol, and polyethylene glycol; sugar alcohols such as mannitol and sorbitol; polysorbates such as suspending agents, PEG, sorbitan ester, polysorbate 20, and polysorbate 80; surfactants such as Triton, tromethamine, lecithin, cholesterol; stability-enhancing agents such as sucrose, and sorbitol; elasticity-enhancing agents; transport agents, diluents; excipients; and/or pharmaceutical auxiliary agents such as sodium chloride, potassium chloride, mannitol/ sorbitol. The amount of these substances added to a preparation is preferably 0.01 to 100 times, more preferably 0.1 to 10 times the weight of the anti-human oculospanin antibody.

Those skilled in the art can appropriately determine the formulation suitable for preparation of a pharmaceutical composition depending upon the disease and administration route.

The excipient and carrier used in a pharmaceutical composition may be a liquid or solid substance. Examples of a suitable excipient and carrier may include injectable solutions, saline, artificial cerebral spinal fluid and other substances usually used for parenteral administration. Furthermore, neutral saline and saline containing serum albumin may be used as a carrier. A pharmaceutical composition may contain a Tris buffer of pH 7.0 to 8.5 and an acetate buffer of pH 4.0 to 5.5, which may be supplemented with sorbitol and other compounds. A pharmaceutical composition according to the present invention having a selected composition is prepared with a requisite purity in appropriate drug form, or as a lyophilized product or a liquid product. To describe this more specifically, a pharmaceutical composition containing the anti-human oculospanin antibody can be formed into a lyophilized product using an appropriate excipient such as sucrose.

A pharmaceutical composition according to the present invention can be prepared for parenteral use or for oral use for gastrointestinal absorption. The composition and concentration of a preparation can be chosen depending upon the administration method. As an anti-human oculospanin antibody contained in a pharmaceutical composition according to the present invention exhibits higher affinity for human oculospanin; in other words, the higher the affinity of anti-human oculospanin antibody for human oculospanin, as expressed by the dissociation constant (Kd value), that is, the lower the Kd value, the higher the efficacy of the pharmaceutical composition of the present invention at a lower dose. Therefore, based on this, the dose amount of the pharmaceutical composition of the present invention to a person can be determined. The humanized anti-human oculospanin antibody may be administered to a person as a single dose at an interval of 1 to 30 days in an amount of about 0.1 to 100 mg/kg.

Examples of forms of a pharmaceutical composition of the present invention may include injections such as drip infusions, suppository agents, pernasal agents, sublingual agents, and percutaneous absorption agents.

7. Search for a Substance Having Direct Interaction

According to another aspect, the present invention is directed to a drug design approach for obtaining a substance capable of inhibiting the activity of human oculospanin based on the tertiary structure of the protein. This approach is known as a rational drug design method and is used to search for a compound capable of efficiently inhibiting or activating a function, such as enzymatic activity or binding to a ligand, cofactor or DNA. As an example of such a compound, a protease inhibitor serving as anti-HIV agent presently marketed is well known. In analyzing the three-dimensional structure of human oculospanin according to the present invention, a generally well known method such as X-ray crystallography or nuclear magnetic resonance conceivably can be used. Furthermore, in searching for or designing a substance for inhibiting the function of human oculospanin, a computer-aided drug design method (CADD) can be used. As an example of this case, a low molecular weight compound (International Publication WO 99/58515) inhibiting the action of AP-1 is known which is expected to act as a novel genomic drug for treating chronic rheumatoid arthritis. By virtue of such a method, it is possible to obtain a substance inhibiting the function of human oculospanin by directly binding to the human oculospanin or by inhibiting the interaction between the human oculospanin and other factors.

Furthermore, according to another aspect, the present invention relates to a polypeptide associated with human oculospanin of the present invention, in other words, a partner protein for controlling the activity of human oculospanin. More specifically, the present invention relates to a screening method for such a partner protein for controlling the activity of human oculospanin.

One aspect of such a screening method comprises a step of bringing a test protein sample into contact with human oculospanin, thereby selecting a protein binding to the human oculospanin. Such a method includes purification of a protein by making use of its affinity for purified human oculospanin. To describe more specifically, first, a sequence formed of 6 histidines is bound to human oculospanin as an affinity tag. The resultant human oculospanin is incubated in a cell extract solution (that is, a fraction passed through a column charged with nickel-agarose) at 4° C. for 12 hours. Then, a nickel-agarose carrier is separately added to the mixture and the mixture is incubated at 4° C. for one hour. After the nickel-agarose carrier is sufficiently washed with a washing buffer, 100 mM imidazole is added to the mixture to elute a protein specifically binding to human oculospanin and contained in the cell extract solution. The purified protein is analyzed to determine its structure. A protein that can be purified as described above includes a protein which binds directly to human oculospanin and a protein forming a complex as a subunit with a protein which binds directly to human oculospanin, but having no binding activity for human oculospanin, thus binding indirectly to human oculospanin [see Experimental Medicine, Supplementary volume, Biomanual series 5, "Transcriptional factor investigation method" pp 215-219 (published by Yodosha Co., Ltd.)].

As alternative methods, there is a cloning method in accordance with Far-Western blot (Experimental Medicine, Supplementary volume, New Genetic Engineering Handbook, pp76-81, published by Yodosha Co., Ltd.), and a two-hybrid system using a yeast or a mammalian cell (Experimental Medicine, Supplementary volume, New Genetic Engineering Handbook, pp66-75, published by Yodosha Co., Ltd.), and "Checkmate mammalian two hybrid system" (manufactured by Promega). However, the present invention is not limited to use of these methods.

If cDNA of a partner protein directly or indirectly interacting with human oculospanin in this manner is available, it can be used in functional screening of a substance inhibiting the interaction between human oculospanin and the partner protein. More specifically, a fusion protein of human oculospanin with glutathione-S-transferase can be prepared. The fusion protein is allowed to bind to a microplate covered with anti-glutathione-S-transferase antibody and a biotinylated partner protein is brought into contact with the fusion protein. The binding of the partner protein with the fusion protein can be detected using alkaline phosphatase conjugated with streptavidin. When the biotinylated partner protein is added, test substances are added at the same time to select a substance which promotes or inhibits the binding of the fusion protein and the partner protein. By this method, a substrate directly acting on the fused protein or a substance directly acting on the partner protein can be obtained.

When the fused protein binds indirectly to the partner protein via another factor, the assay is performed in the presence of a cell extraction solution containing this factor. In this case, a substance, which may act upon the factor, may be selected.

When the partner protein obtained has the activity of suppressing the function of human oculospanin, it is possible to screen an anti-cancer agent, for example, a useful candidate substance as a therapeutic agent for prostate cancer, in accordance with a test method using an expression vector comprising the human oculospanin gene, as described above. Furthermore, when the obtained partner protein has the activity of suppressing the function of human oculospanin, a polynucleotide having a nucleotide sequence encoding such a suppressor can be used in gene therapy for cancer.

Such a polynucleotide can be obtained by analyzing the amino acid sequence of the identified inhibitor, synthesizing an oligonucleotide probe comprising a nucleotide sequence encoding the amino acid sequence and screening a cDNA library or genomic library. Furthermore, in the case where a peptide having inhibitory activity against a function of human oculospanin is derived from an artificial peptide library synthesized at random, DNA comprising a nucleotide sequence encoding the amino acid sequence of the peptide can be chemically synthesized.

In gene therapy, a gene encoding such an inhibitor is integrated, for instance, into a virus vector and a patient can be infected with a virus (attenuated) comprising the resultant recombinant virus vector. In the body of the patient, an anti-cancer factor is produced and functions to suppress proliferation of cancer cells. In this manner, it is possible to treat cancer.

As a method of introducing a gene therapeutic agent into a cell, both a gene transfection using a virus vector and a non-viral gene transfection can be used [Nikkei Science, 4, (1994), p. 20-45; Experimental Medicine, Extra number, 12 (15) (1994); Experimental Medicine, Supplementary volume, "Basic Technology of Gene Therapy" Yodosha, Co., Ltd. (1996)].

Examples of gene transfection using a virus vector include methods of integrating DNA encoding an inhibitor or a mutated version of the DNA into DNA virus or using a RNA virus such as retrovirus, adenovirus, adeno-associated virus, herpes virus, vaccinia virus, pox virus, polio virus, or sindbis virus and introducing the virus vector into a body. Of these, methods using retrovirus, adenovirus, adeno-associated virus, and vaccinia virus are particularly preferred. Examples of non-viral gene transfection include a method of administering an expression plasmid directly into the muscle (DNA vaccination method), liposome treatment, lipofection, microinjection, calcium phosphate treatment, and an electroporation method. Of these, DNA vaccination and liposome treatment are preferred.

To use a gene therapeutic agent as a medicine in practice, there is an in vivo method for introducing DNA directly into the body, and an ex vivo method which comprises taking a certain type of cells out of the body, introducing DNA into the cells, and returning the cells into the body [Nikkei Science, 4, (1994), p. 20-45; The Pharmaceutical Monthly, 36(1), 23-48 (1994); Experiment Medicine, Extra number 12 (15) (1994)].

When the gene therapeutic agent is administered in accordance with the in vivo method, it is administered through an appropriate administration route, such as a vein, artery, subcutaneous tissue, intradermal tissue, or muscle, which differs depending upon the type of disease and symptoms. When the agent is administered in accordance with an in vivo method, the gene therapeutic agent is generally prepared in the form of an injection; however if necessary, a customarily used carrier may be added. Furthermore, when the agent is prepared in the form of a liposome or membrane-fused liposome (Sendai virus-liposome, etc.), the liposome agent may be supplied as a suspension agent, lyophilized agent, or centrifugally concentrated and lyophilized agent.

A complementary sequence to the nucleotide sequence represented by Sequence ID. No. 1 or a complementary sequence to a partial sequence of this nucleotide sequence can be used as a so-called antisense therapy. As an antisense molecule, use may be made of DNA partially complementary to the nucleotide sequence represented by Sequence ID No. 1 of the sequence listing and formed generally of 15 to 30 mer. Also, use may be made of a stable DNA derivative such as a phosphorothioate derivative, methyphosphonate derivative, or morpholino derivative of the DNA, or a stable RNA derivative such as 2'-O-alkyl RNA. Such an antisense molecule can be introduced into a cell by a method known in the art of the present invention, for example by injecting an extremely small amount of the antisense molecule, by forming a liposome capsule, or by expressing it by use of a vector having an antisense sequence. Such an antisense therapy is useful for treating a disease caused by excessive activity of a protein encoded by the nucleotide sequence represented by Sequence ID No. 1 of the sequence listing.

A composition containing the antisense oligonucleotide useful as a medicine can be prepared by a known method including mixing a pharmaceutically acceptable carrier. Examples of such a carrier and the preparation method are described in Applied Antisense Oligonucleotide Technology (1998 Wiley-Liss, Inc.). A preparation containing an antisense oligonucleotide can be administered orally by mixing with a pharmaceutically acceptable appropriate excipient or diluent, in the form of tablets, capsules, granules, powder or syrup, or administered parenterally in the form of an injection, suppository, patch, or external preparation. These preparations can be prepared by a known method using additives:

excipients including organic excipients such as sugar derivatives (e.g., lactose, white sugar (sucrose), glucose, mannitol, and sorbitol); starch derivatives (e.g., corn starch, potato starch, a starch, and dextrin); cellulose derivatives (e.g., crystalline cellulose); Arabic gum; dextran; and pullulan; and inorganic excipients such as silicate derivatives (e.g., soft anhydrous silicic acid, synthesized aluminium silicate, calcium silicate, and magnesium aluminate metasilicate); phosphates (e.g., calcium hydrogen phosphate); carbonates (e.g., calcium carbonate), and sulfates (e.g., calcium sulfate);

lubricant agents including metal stearates (e.g., stearic acid, calcium stearate, and magnesium stearate); talc; colloidal silica; waxes (e.g., beeswax and spermaceti wax), boric acid; adipic acid; sulfates (e.g., sodium sulfate), glycol; fumaric acid; sodium benzoate; DL leucine; lauryl sulfates (e.g., sodium lauryl sulfate and magnesium lauryl sulfate); silicates (e.g., anhydrous silicate, silicate hydrate); and starch derivatives mentioned above; binding agents including hydroxypropylcellulose, hydroxypropyl methylcellulose, polyvinyl pyrrolidone, macrogol, and the same compounds as mentioned as excipients; disintegrating agents including cellulose derivatives (e.g., low substitution degree hydroxypropylcellulose, carboxymethylcellulose, carboxymethylcellulose calcium, inner-cross-linked carboxymethylcellulose sodium; and chemically modified starch celluloses (e.g., carboxymethylstarch, carboxymethylstarch sodium, and cross-linked polyvinyl pyrrolidone); emulsifying agents including colloid silica (bentnite and bee gum), metal hydroxides (e.g., magnesium hydroxide and aluminium hydroxide), anionic surfactants (e.g., sodium lauryl sulfate and calcium stearate); cationic surfactants (e.g., benzalkonium chloride) and non-ionic surfactants (e.g., polyoxyethylene alkylether, polyoxyethylene sorbitan fatty acid ether, and sucrose fatty acid ester); stabilizing agents including paraoxy benzoates (e.g., methyl paraben, propyl paraben); alcohols (e.g., chloro butanol, benzyl alcohol, and phenylethyl alcohol); benzalkonium chloride; phenols (e.g., phenol and cresol); thimerosal; dehydro acetate; and sorbic acid; flavoring agents including sweeteners, acidic flavors and flavors generally used; and diluents.

As a method of introducing a compound of the present invention into a patient, a colloidal dispersion system may be used in addition to the aforementioned methods. The colloidal dispersion system is expected to contribute to increasing the stability of the compound in the body and efficiently transporting the compound to a specific organ, tissue or cell. The choice of colloidal dispersion system is not particularly limited as long as it is generally used, and for example, a lipid-based dispersion system may be used which includes polymer complexes, nanocapsules, microspheres, beads, or oil-in-water emulsifiers, micelles, micelle mixtures, or liposomes. A preferable colloidal dispersion system consists of multiple liposomes or vesicles of an artificial membrane, which is effective in efficiently transferring a compound to a specific organ, tissue or cell (Mannino et al., Biotechniques, 1988, 6, 682; Blume and Cevc, Biochem. et Biophys. Acta, 1990, 1029, 91; Lappalainen et al., Antiviral Res., 1994, 23, 119; Chonn and Cullis, Current Op. Biotech., 1995, 6, 698).

A unilamellar liposome ranging from 0.2 to 0.4 μm in size is capable of encapsulating a large proportion of macromolecules contained in an aqueous buffer. A compound can be encapsulated in such an aqueous inner membrane and transported to the brain cells in biological active form (Fraley et al., Trends Biochem. Sci., 1981, 6, 77). The liposome is generally composed of a mixture of a lipid, particularly a phospholipid, more particularly a phospholipid having a high phase transition temperature, with one or more types of steroid, in particular, cholesterol. Examples of a lipid useful for producing a liposome include phosphatidyl compounds such as phosphatidyl glycerol, phosphatidyl choline, phosphatidylserine, sphingolipid, phosphatidylethanolamine, cerebroside, and ganglioside. Of these, particularly useful is diacylphosphatidyl glycerol in which a lipid moiety has 14 to 18 carbon atoms, in particular, 16 to 18 carbon atoms and is saturated (that is, no double bond is present within the C14-C18 carbon atom chain). Typical phospholipids include phosphatidyl choline, dipalmitoyl phosphatidyl choline and distearoyl phosphatidyl choline.

The colloidal dispersion system containing liposomes can be used for passive or active targeting. Passive targeting can be attained using a tendency inherent to liposomes, which tend to distribute in the reticuloendothelial system of an organ containing sinusoids. Alternatively, active targeting can be attained by modifying a liposome, for example, by binding a specific ligand thereto, such as viral protein coat (Morishita et al., Proc. Natl. Acad. Sci. (U.S.A.), 1993, 90, 8474), a monoclonal antibody (or its appropriate binding portion), sugar, glycolipid, or protein (or its appropriate oligopeptide fragment); or alternatively, by modifying the composition of the liposome in order to distribute it in organs or cell types other than those where liposomes are naturally localized. The surface of the colloidal dispersion system can be modified in various methods for targeting. In a delivery system using a liposome as a targeting means, to maintain a ligand for use in targeting by keeping tight association with a lipid bilayer, a lipid group is integrated into the lipid bilayer of the liposome. To bind a lipid chain to the targeting ligand, various linking groups can be used. Examples of such a targeting ligand binding to a specific cell surface molecule predominantly found on the cell to which an oligonucleotide according to the present invention is desired to be delivered include (1) hormone, growth factor or an appropriate oligopeptide fragment thereof binding to a specific cellular receptor predominantly expressed by a cell to which delivery is desired; and (2) a polyclonal antibody, monoclonal antibody, or an appropriate fragment thereof (e.g., Fab; F (ab)'2) specifically binding to an antigenic epitope predominantly found on a target cell. Two or more bio activators can be formed into a complex within a single liposome and administered. A medicinal agent for improving intracellular stability and/or targeting ability of the contents can be added to the colloidal dispersion system.

Although a therapeutic gene of the present invention can be used in an amount varying with symptom intensity, age, etc. In the case of peroral administration, the lowermost limit per dose is 1 mg (preferably 30 mg) and the uppermost limit per dose is 2,000 mg (preferably 1,500 mg). In the case of injection, the lowermost limit per dose is 0.1 mg (preferably 5 mg) and the uppermost limit per dose is 1,000 mg (preferably 500 mg). Such a dose can be administered subcutaneously, intramuscularly or intravenously.

Now, the present invention will be more specifically described in detail by way of Examples, which should not be construed as limiting the present invention. Note that individual operations regarding gene manipulation in the following Examples are performed in accordance with the methods described in "Molecular Cloning" (by Sambrook, J., Fritsch, E. F. and Maniatis, T., published by Cold Spring Harbor Laboratory Press 1989), or performed using commercially available reagents or kits in accordance with the protocols thereof.

EXAMPLE 1

Screening of a Gene Specifically Expressed in a Cancer Cell

Expression profile analysis was performed, using an EST probe (Affymetrix GeneChip HG-133 probe 223795_at: manufactured by Affymetrix) having a nucleotide sequence partially overlapping with the sequence represented by Sequence ID No. 1 of the sequence listing, by use of the data base (GeneExpress Software System Release 1.4.2) provided by Genelogic company.

Expression of the human oculospanin gene in various cells was quantitatively compared by considering its transcription. As a result, the expression levels in 8 melanocyte samples were to found to be significantly high, compared to the levels in other cells samples, including 12 blood-cell samples, 6 glia cell samples, 62 epithelial cell samples (P values thereof were <0.0001,=0.0007, and <0.0001 sequentially in order, FIG. 1, upper panel).

Next, the expression levels of the human oculospanin gene were compared in samples derived from tissue. More specifically, the amount of transcription was compared with respect to 66 skin samples from healthy individuals and 33 melanoma samples. As a result, the amount of transcription in the melanoma samples was found to be significantly high (P value=0.000 1, FIG. 1, lower panel). Furthermore, when skin samples from 66 healthy individuals were compared with 12 melanoma samples derived from the melanoma skin tissue, the amount of transcription in the melanoma samples was found to be significantly higher (P value=0.007, FIG. 2, upper panel).

Figure 2:
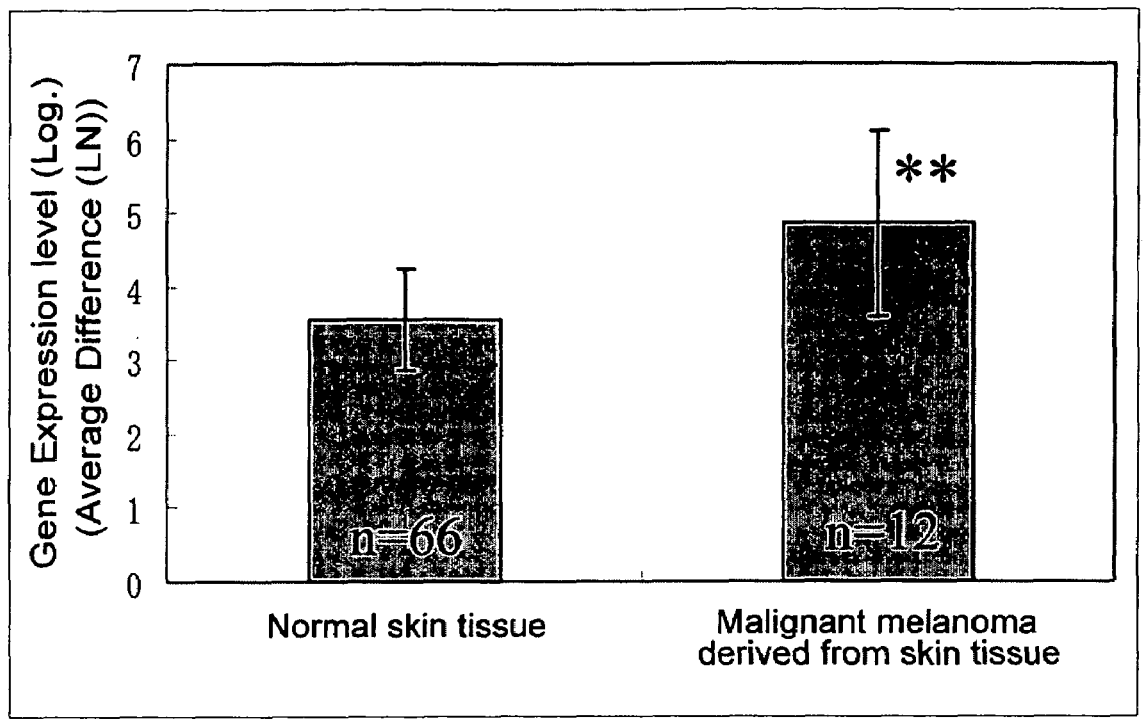
FIG. 2, the upper figure, is a graph showing the expression level of the human oculospanin gene in a healthy person's skin samples and in melanoma samples derived from skin tissue; and the lower figure is a graph showing the expression level of the human oculospanin gene in a healthy person's skin samples and in melanoma samples derived from lymph node tissue.
Figure 2:
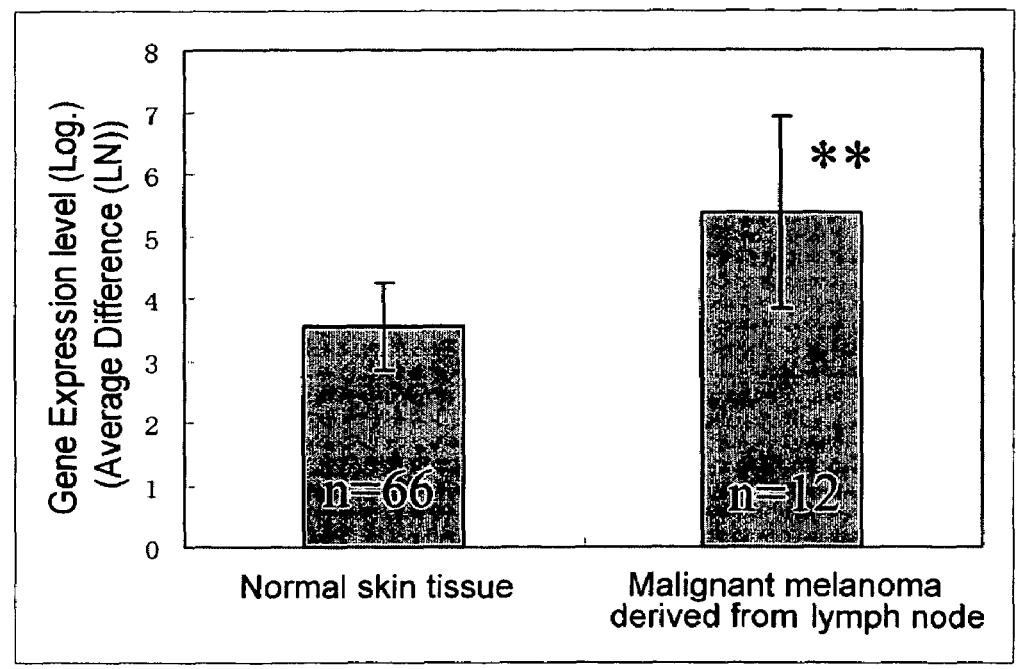

When 66 healthy person's skin samples were compared to 12 melanoma samples derived from lymph node tissue, the amount of transcription in the melanoma samples was found to be significantly higher (P value=0.0003, FIG. 2, lower panel).

Figure 3:
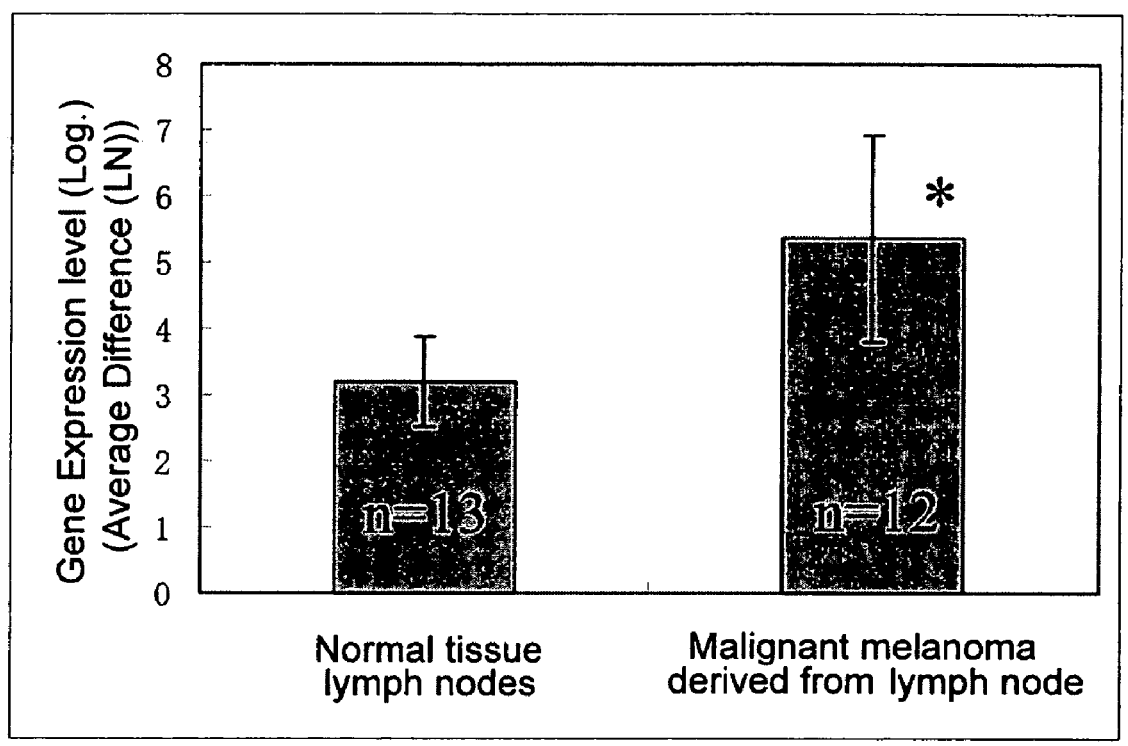
FIG. 3 is a graph showing the expression level of the human oculospanin gene in samples derived from a healthy person's lymph node and in melanoma samples derived from lymph node tissue.

Furthermore, when 13 healthy person's samples derived from lymph node were compared to 12 melanoma samples derived from lymph node tissue, the amount of transcription in the melanoma samples was found to be significantly higher (P value=0.0011, the panel of FIG. 3).

EXAMPLE 2

Acquisition of the Human Oculospanin Gene and Construction of Expression Plasmid a) PCR Reaction As a primer for amplifying human oculospanin cDNA by PCR, oligonucleotides having the following sequences were synthesized in accordance with a customary method.
5'-CACCATGGAGGAGGGGGAGAGGAGCCC-3'
(Primer 1, Sequence ID No. 5of the sequence listing)
5'-GCCCCGGGCGGGTTTGGCAGCGG-3' (Primer 2, Sequence ID No. 6 of the sequence listing)

Note that Primer 1 is an oligonucleotide constructed by adding 4 bases, CACC, as a KOZAK sequence, upstream of the initiation codon of the human oculospanin gene, in other words, an oligonucleotide constructed by adding the 4 bases, the CACC sequence, to the 5' side of the nucleotide sequence consisting of nucleotides No. 1 to 23 of the Sequence ID No. 1 of the sequence listing. The CACC sequence, since it forms a chain complementary to the 3' terminus of the vector when it is integrated into the cloning vector pENTR/D-TOPO, makes it possible to integrate the gene into the vector whilst maintaining the orientation of the gene. Primer 2 is an oligonucleotide composed of a chain complementary to a nucleotide sequence consisting of nucleotides No. 1043 to 1065 of the sequence ID No. 1 of the sequence listing.

The PCR reaction was performed using PLATINUM Pfx DNA polymerase (manufactured by Invitrogen) in accordance with the protocol provided. More specifically, to 0.1 μl of the first strand cDNA obtained, 1.5 μl of each of 10 pmol/μl synthetic primer 1 and synthetic primer 2, 5 μl of 10×Pfx Amplification Buffer, 1.5 μl of 10 mM dNTP Mix, 1 μl of 50 mM MgSO$_4$, 0.5 μg of PLATINUM Pfx DNA polymerase, 10 μl of 10×PCRx Enhancer Solution, and 28.9 μl of sterilized water were added to prepare 50 μl of a PCR reaction solution. The PCR reaction was performed using a Peltier Thermal Cycler TPC-200 DNA Engine (manufactured by MJ Research), first by heating the PCR solution at 94° C. for 2 minutes, repeating 5 times a thermal cycle consisting of reactions at 94° C. for 30 seconds and 65° C. for 2 minutes; 5 times a thermal cycle consisting of reactions at 94° C. for 30 seconds, 60° C. for 40 seconds, and 68° C. for one minute and 20 seconds; 5 times a thermal cycle consisting of reactions at 94° C. for 30 seconds, 55° C. for 40 seconds, and 68° C. for one minute and 20 seconds; 35 times a thermal cycle consisting of reactions at 94° C. for 30 seconds, 50° C. for 40 seconds, and 68° C. for one minute and 20 seconds and finally maintaining the PCR solution at 68° C. for 10 minutes, and then storing the solution at 4° C. A desired cDNA was obtained by subjecting the reaction product to 1.5% agarose gel electrophoresis, confinning amplification of the NM__031945 cDNA (1069 bp), and purifying the DNA from the agarose gel using the S.N.A.P. UV-Free Gel Purification Kit (manufactured by Invitrogen) in accordance with the protocol provided. The concentration of cDNA thus purified was determined by use of 1D Image Analysis Software Version 3.5 (Kodak Digital Science EDAS290; manufactured by Kodak) with reference to a 1 kb DNA Ladder which was used as a concentration reference.

b) Cloning of the Human Oculospanin cDNA into the PENTR/D-TOPO Vector

The NM__031945 cDNA obtained in Example 2a) was cloned into the pENTR/D-TOPO vector using the pENTR Directional TOPO Cloning Kit (manufactured by Invitrogen) in accordance with the protocol provided. More specifically, NM__031945 cDNA was mixed with the pENTR/D-TOPO vector, having Topoisomerase bound thereto, in the reaction buffer supplied with the kit and incubated at room temperature for 30 minutes. OneShot TOP10 Chemically Competent *E. coli* (manufactured by Invitrogen) was transformed using the reaction product obtained and cultured on an LB agar medium containing 50 μg/ml kanamycin. The resultant *E. coli* colonies, which exhibited resistance to kanamycin, were selected and cultured, in a liquid TB medium containing 1 ml of 50 μg/ml kanamycin, at 37° C. overnight. Plasmid DNA was isolated and purified by using a Montage Plasmid Miniprep$_{96}$ Kit (manufactured by Millipore). Then, the plasmid DNA thus obtained was subjected to a reaction using the BigDye Terminator v3.0 Cycle Sequencing Ready Reaction Kit in accordance with the protocol provided, the nucleotide sequence was analyzed using an ABI PRISM 3100 DNA Analyzer (manufactured by Applied Biosystems). As a result, it was confirmed that cDNA (Sequence ID No. 1 of the sequence listing) having an open reading frame of the nucleotide represented by GenBank ACCESSION NO.NM__031945 was integrated into the pENTR/D-TOPO vector.

Next, the gene was transferred to an expression vector, pcDNA3.1 /DEST40 (manufactured by Invitrogen), using the GATEWAY™ system. To explain more specifically, 4 μl of GATEWAY™ LR Clonase™ Enzyme Mix (manufactured by Invitrogen), 4 μl of LR Reaction Buffer, 0.3 μg of pENTR/D-TOPO-NM__031945, and 0.3 μg of pcDNA3.1/ DEST40 were mixed and made up to a 20 μl reaction solution in TE buffer. The reaction solution was allowed to react at 25° C. for one hour. After the reaction, 2 μl of proteinase K was added and a reaction was performed at 37° C. for 10 minutes. Using the resulting reaction product, OneShot TOP10 Chemically Competent *E. coli* (manufactured by Invitrogen) were transformed and cultured in a LB agar medium containing 50 μg/ml of ampicillin. The resulting *E. coli* colonies, exhibiting ampicillin resistance, were selected and cultured in 100 ml of liquid LB medium containing 50 μg/ml ampicillin at 37° C. overnight, and plasmid DNA (pcDNA3.1-DEST40-NM__031945) was isolated and purified by use of Plasmid MAXI Kit (manufactured by QIAGEN).

EXAMPLE 3

Introduction of the Human Oculospanin Gene into Cells, Confirmation that the Human Oculospanin Gene Product is Expressed, and Preparation of a Membrane Fraction from Human Oculospanin Expressing Cells for use as an Immunogen a) Transfection of NIH3T3 Cells with the Plasmid pcDNA3.1-DEST40-NM_031945

NIH3T3 cells were transfected with plasmid pcDNA3.1-DEST40-NM_031945 obtained in Example 2 as follows. The transfection of the NIH3T3 cells was performed by lipofection using the Lipofectamine™ 2000 Reagent manufactured by Invitrogen. To explain more specifically, first, NIH3T3 cells were grown in a 6 well plate up to a semi-confluent state. Next, the cells were washed once with antibiotic-free DMEM containing 10% fetal calf serum, then 200 μl of antibiotic-free DMEM containing 10% fetal calf serum was added to the cells. Then, to a 1.5 ml Eppendorf tube, 100 μl of serum-free medium (DMEM) and 2 μg of plasmid DNA (pcDNA3.1-DEST40-NM_031945) recovered in the aforementioned manner were added and mixed. To another 1.5 ml Eppendorf tube, 96 μl of serum-free medium (DMEM) and 4 μl of Lipofectamine™ 2000 Reagent were added and mixed. The DNA solution and the Lipofectamine solution were mixed and allowed to stand still at room temperature for 20 minutes. Thereafter, the DNA-Lipofectamine solution mixture was added to the cells and cultured at 37° C. in 5% $CO_2$. After 4 hours, 1 ml of DMEM containing 10% fetal calf serum was added to the cells which were cultured at 37° C. overnight in 5% $CO_2$.

b) Confirmation of Expression of the Plasmid pcDNA3.1-DEST40-NM_031945 in NIH3T3 Cells The cell culture product thus obtained was recovered. The negative control containing no cDNA or NIH3T3 cells transfected with the pcDNA3.1-DEST40-NM_031945 obtained were washed with a PBS (−) buffer solution (manufactured by Invitrogen). The cells were dispersed in a sample buffer solution (manufactured by BioRad) containing 2-mercaptoethanol for use in SDS polyacrylamide electrophoresis (SDS-PAGE). SDS-PAGE was performed using 12.5% polyacrylamide gel (e PAGEL E-T12.5L; manufactured by ATTO corporation) under reducing conditions.

After electrophoresis, bands were transferred from the polyacrylamide gel to a Polyvinylidene Difluoride(PVDF) membrane (manufactured by Millipore) by use of a gel-membrane transfer apparatus (NP7513 manufactured by Marysol) in a transfer buffer solution (192 mM glycine, 20% methanol, 25 mM Tris) under the following conditions: 4° C., 120 minutes and 200 mA.

Figure 4:
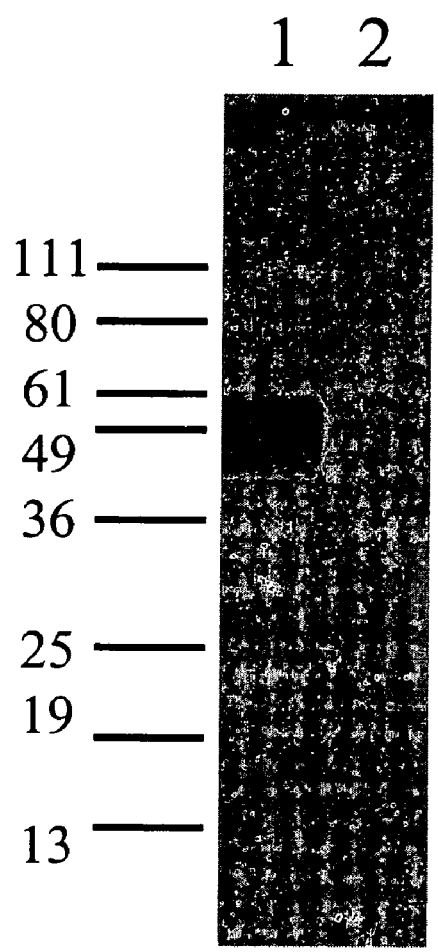
FIG. 4 shows expression of human oculospanin gene products in NIH3T3 cells.

After transfer, the PVDF membrane was subjected to Western blot analysis using an anti-V5-tag antibody (manufactured by Invitrogen). To explain more specifically, first, the PVDF membrane was blocked using blockace (manufactured by Yukijirushi Co.,) once at room temperature for 30 minutes, and put in a plastic bag (trade name: Hybribag manufactured by Cosmo Bio). To the bag, the anti-V5-tag antibody (1000-fold dilution) and 5 ml of blockace were added and the bag was shaken at room temperature for one hour. After one hour, the membrane was removed and washed with PBS containing 0.05% Tween 20 (hereinafter referred to as "0.05% Tween 20-PBS) once at room temperature for 15 minutes and twice for 5 minutes. Thereafter, the membrane was transferred to a new plastic bag. To the bag, 30 ml of a solution containing a horseradish peroxidase labeled anti-rabbit IgG antibody (manufactured by Amersham Pharmacia) diluted 5000 fold with 0.05% Tween 20-PBS, was added and shaken at room temperature for one hour. After one hour, the membrane was taken out and washed with 0.05% Tween 20-PBS once for 15 minutes and four times for 5 minutes. After washing, the membrane was placed on a wrapping film and a band having the anti-V5-tag antibody bound thereto was detected by use of ECL Western blotting detection solution (manufactured by Amersham Pharmacia). The membrane was placed on the wrapping film and soaked in the ECL Western blotting detection solution for one minute and then exposed to an X-ray film (one minute). As a result, a band specific to the NIH3T3 cells having plasmid pcDNA3.1-DEST40-NM_031945 DNA introduced therein was detected due to the presence of the anti-V5-tag antibody (FIG. 4).

c) Transfection of BALB-3T3 Cells with the Plasmid pcDNA3.1-DEST40-NM_031945

BALB-3T3 cells (American Type Culture Collection No. CCL-163) were cultured in three Cell Trays (culturing area: 500 $cm^2$ manufactured by Sumitomo Bakelite Co., Ltd.) for cell culture in Dulbecco's Modified Eagle Medium (hereinafter referred to as "DMEM") manufactured by Nissui Pharmaceutical Co., Ltd., containing 10% bovine serum (hereinafter referred to as "BS") manufactured by Gibco), at 37° C. in 5% $CO_2$ gas up to a semi-confluent state. Thereafter, the BALB-3T3 cells were transfected with the plasmid pcDNA3.1-DEST40-NM_031945. The transfection of the BALB-3T3 cells was performed by lipofection using Geneporter™ 2 Transfection Reagent (manufactured by Gene Therapy Systems). To explain more specifically, the cells were washed once using a serum-free medium, DMEM. To the cells, 500 ml of the serum-free medium (DMEM) was added. Then, to a 50 ml Falcon tube, 6 ml of New DNA diluent and 240 μg of plasmid DNA (pcDNA3.1-DEST40-NM_031945) recovered by the aforementioned method were added and mixed. To another 50 ml Falcon tube, 4.8 ml of serum-free medium (DMEM) and 1200 μl of Geneporter™ 2 Reagent were added and mixed. The DNA solution and the Geneporter™ 2 solution were mixed and allowed to stand still at room temperature for 20 minutes. Thereafter, the solution mixture with DNA-Geneporter™ 2 was added to the cells (4 ml/tray) and cultured at 37° C. in the presence of 5% $CO_2$. After 4 hours, DMEM containing 20% bovine serum was added in an amount of 50 ml/tray and cultured at 37° C. in 5% $CO_2$ overnight.

d) Preparation of the Cell Membrane Fraction

The cells cultured by the aforementioned method were washed with PBS (−) buffer solution (manufactured by Invitrogen). The cells were collected using a cell scraper (manufactured by Sumitomo bakelite Co., Ltd.), and suspended in 7 ml of 5 mM Tris buffer at pH 8.0. The resulting cell solution was allowed to stand still at 4° C. for 30 minutes. The cells were crushed using a Dounce Type B homogenizer (30 strokes) and centrifuged at 1000 G for 10 minutes. The supernatant was recovered and centrifuged at 78,000 G for 100 minutes using an ultracentrifugation apparatus (manufactured by Hitachi) and the precipitate was recovered. The precipitate was subjected to a sugar density gradient to concentrate the membrane fragments. More specifically, the precipitate was dissolved in 3 ml of a solution of 57% sugar and 0.25M Tris buffer, pH 8.0. The resulting solution was transferred to an ultracentrifuge tube. An aliquot of 3 ml of a solution of 57% sugar and 0.25M Tris buffer, pH 8.0 and 1.5 ml of a solution of 37.5% sugar and 0.25M Tris buffer pH 8.0 were layered sequentially onto the cell precipitate solution. Then, centrifugation was performed using an ultracentrifugation apparatus at 75,500 G for 16 hours. An aliquot of 1 ml was taken from the top of each tube. To each aliquot (fraction), 10 mL of 5 mM Tris buffer pH 8.0 was added and this was subjected to ultracentrifugation at 78,000 G for one hour to recover the precipitate. To the precipitate 500 µl of 5 mM Tris buffer, pH 8.0 was added and the cell solution was homogenized using a Dounce type B homogenizer (10 strokes). The cell membrane fraction was identified by Western Blotting method described in the Section "Confirmation of Expression" and used as an immunogen.

EXAMPLE 4

Immunization of Mice and Cell Fusion (4-1) Immunization 1 ml (total protein amount: 100 µg) of the membrane fraction solution of the human oculospanin expressing cells obtained in Example 3 was injected intraperitoneally into BALB/c mice which were 4 to 10 weeks old (purchased from Japan SLC Inc.) After two weeks, the same membrane fraction solution (20 µg protein/mouse) was injected into the abdominal cavity as a booster immunization.

(4-2) Cell Fusion

The spleen was excised from a mouse at three days after the booster immunization and added to 10 ml of a serum-free RPMI 1640 medium (10.4 g/l, RPMI 1640 "Nissui"(1): manufactured by Nissui Pharmaceutical Co., Ltd., hereinafter referred to as "serum-free RPMI medium") containing 20 mM HEPES buffer (pH 7.3), 350 mg/ml sodium hydrogen carbonate, 0.05 mM β-mercaptoethanol, 50 units/ml penicillin, 50 µg/ml streptomycin, and 300 µg/ml L glutamic acid, and the spleen was crushed on the mesh of a cell strainer (cell strainer; manufactured by Falcon) using a spatula. The cell suspension solution passed through the mesh was centrifuged to collect the spleen cells. The spleen cells were washed twice with serum-free RPMI medium, suspended in serum-free RPMI medium and the number of cells was counted.

Myeloma cells NSI (American Type Culture Collection TIB-18) were cultured in ASF 104 medium (manufactured by Ajinomoto; hereinafter referred to as the "serum-containing ASF medium") containing 10% FCS (manufactured by Gibco BRL) at 37° C. in 5% $CO_2$ gas such that the cell density did not exceed $1\times10^8$ cells/ml. The inyeloma cells thus prepared were washed with serum-free RPMI medium in the same manner as above and suspended in serum-free RPMI medium and the number of cells was counted.

The NSI cell suspension solution containing about $3\times10^7$ cells and the spleen cell suspension solution containing about $3\times10^8$ cells were mixed and subjected to centrifugation, and thereafter the supernatant was completely removed. The cell fusion operation below was performed whilst maintaining the plastic centrifuge tube containing the pellet in a beaker containing hot water at 37° C. To the pellet, 1 ml of 50% (w/v) polyethylene glycol 1500 (manufactured by Boehringer Mannheim) was slowly added by pipette whilst agitating the pellet using the tip. Thereafter, 1 ml of the serum-free RPMI medium, previously warmed to 37° C., was gently added in twice and a further 7 ml of serum-free RPMI medium was added. After centrifugation, the supernatant was removed and 10 ml of hypoxanthine aminopterin thymidine medium (hereinafter referred to as "HAT medium"; manufactured by Boehringer Mannheim) containing 10% FCS was added by pipette whilst gently agitating using the tip. After 20 ml of the HAT medium containing 10% FCS was added, the resulting solution was dispensed to a 96-well cell culture microplate at an amount of 100 µl/well and cultured at 37° C. in 5% $CO_2$ gas. Seven to eight days later, to wells containing medium with a tinge of yellow, fresh HAT medium was added in an amount of 100 µl/well. The fused cells thus obtained were subjected to screening by limiting dilution analysis as mentioned below.

(4-3) Limiting Dilution

The thymus gland was excised from female BALB/c mouse which were 4 to 10 weeks old (purchased from Japan SLC Inc.) and crushed on the mesh of a cell strainer (Cell Strainer, manufactured by Falcon) using a spatula. The cells passed through the mesh were washed twice with hypoxanthine thymidine medium (hereinafter referred to as the "HT medium", manufactured by Boehringer Mannheim) containing 10% FCS. The thymus gland cells of the mouse were suspended in 30 ml of the HT medium containing 10% FCS. The suspension solution thus obtained was used as a feeder cell solution. The culture solution containing the fused cells obtained in Section (4-2) was diluted 10 to 100 fold with the feeder cell solution depending upon the cell density and further serially diluted with the feeder cell solution until the density of the fused cells was 5 cells/ml, 1 cell/ml and 0.5 cells/ml. Each of the samples thus prepared was dispensed into a 96-well cell culture microplate in an amount of 100 µl per well and cultured at 37° C. in 5% $CO_2$ gas for 5 days.

(4-4) Screening (4-4-1) Cell ELISA

Human oculospanin expressing cells were maintained by culturing them in RPMI 1640 medium (manufactured by Invitrogen) supplemented with 10% fetal calf serum (manufactured by Moregate Biotech), 20 mM HEPES (manufactured by Sigma) and 55 µM 2-mercaptoethanol (manufactured by Invitrogen) at 37° C. in 5% $CO_2$ gas. Human oculospanin expressing cells in the logarithmic growth phase were seeded into a cell culture flask at a density of $2\times10^4$ cells/cm$^2$ and cultured for 3 days. The human oculospanin expressing cells thus prepared were transferred to a 50 ml tube and centrifuged using a HITACHI himac CF8DL at 1,000 rpm for 5 minutes (Centrifugation condition 1). The supernatant was removed and the human oculospanin expressing cells were suspended in a medium. Thereafter, the number of living cells was counted using 0.4% tryphan blue solution (manufactured by Sigma). The density of the live human oculospanin expressing cells was adjusted using the medium to be $10^7$ cells per ml and the resultant medium was dispensed to a 96-well U-bottom plate in an amount of 100 µl/well. The 96-well U-bottom plate was centrifuged using a HITACHI himac CF8DL at 15,000 rpm for one minute (Centrifugation condition 2). The supernatant was removed using a 200 µl tip. The 96-well U-bottom plate was tapped on the side surface to suspend the human oculospanin expressing cells. To the suspension, hybridoma culture supernatant solutions whose concentrations were adjusted to 10 µg/ml, 5 µg/ml, 2.5 µg/ml with a medium cooled on ice, were added in an amount of 100 µl/well. Whilst the 96-well U-bottom plate was stirred using a plate mixer (manufactured by Fujirebio Inc.) at intervals of 15 minutes, a reaction was performed at 4° C. for 1.5 hours. After completion of the reaction, the 96-well U-bottom plate was centrifuged under Centrifugation condition 2, and the supernatant was removed using a 200 µl tip. A solution (PBS-5% FBS) prepared by adding 5% fetal calf serum to PBS(−)(manufactured by Nissui Pharmaceutical Co., Ltd.) was added to the wells in an amount of 200 µl per well. After stirring using a plate mixer, centrifugation was performed under Centrifugation condition 2 and the supernatant was removed using a 200 µl tip. Thereafter, the aforementioned operation was repeated twice. The 96-well U-bottom plate was tapped on the side surface to suspend the human oculospanin expressing cells. To the suspension, peroxidase-labeled anti-human IgG antibody (manufactured by Kirkegaad & Perry Laboratories) diluted 500 fold with PBS-5%FBS cooled in ice was added in an amount of 100 μl/well. While the 96-well U-bottom plate was stirred using a plate mixer at intervals of 15 minutes, a reaction was performed at 4° C. for 1.5 hours. After completion of the reaction, the 96-well U-bottom plate was centrifuged under Centrifugation condition 2 and the supernatant was removed using a 200 μl tip. Then, PBS-5% FBS was added in an amount of 200 μl/well and stirred using a plate mixer, centrifuged under Centrifugation condition 2, and then the supernatant was removed using a 200 μl tip. Thereafter, the aforementioned operation was repeated twice. The 96-well U-bottom plate was tapped on the side surface to suspend the human oculospanin expressing cells. To the suspension, a color development substrate for peroxidase (manufactured by Nacalai Tesque Inc.) adjusted to room temperature was added in an amount of 100 μl/well and stirred using a plate mixer for 10 minutes. After centrifugation was performed under Centrifugation condition 2, the supernatant was transferred to 96-well flat-bottomed plate in an amount of 50 μl/well and absorbance was measured at 405 nm using a plate reader (1420 ARVO multilabel counter, manufactured by PerkinElmer Inc.)

(4-4-2) Flow Cytometry

The human oculospanin expressing cells obtained in Example 3 were cultured and grown in RPMI 1640 medium containing 10% FCS at 37° C. in 5% $CO_2$ gas. A cell suspension solution, prepared so as to contain $1 \times 10^7$ cells/ml, was dispensed into 96-well U-bottom microplate (manufactured by Nunk) in an amount of 50 μl/well and centrifuged (at 90×g, 4° C. for 10 minutes). The supernatant was removed and the supernatant of the fused cells cultured in Section (4-3) above was added in an amount of 50 μl/well and stirred. The plate was allowed to stand for one hour on ice, subjected to centrifugation (at 90×g, 4° C. for 10 minutes) and the supernatant was removed. The pellet was washed twice with a flow cytometric buffer solution (PBS containing 5% FCS and 0.04% (w/v) sodium azide) in an amount of 100 μl/well and 50 μl of 500-fold diluted goat anti-mouse IgG antibody IgG fraction (manufactured by Organon Technica) labeled with fluorescein-5-isothiocyanate (hereinafter referred to as "FITC") was added as a secondary antibody and allowed to stand still on ice for one hour. After centrifugation (at 90×g, 4° C. for 10 minutes), the supernatant was removed. The pellet was washed twice with 100 μl of the flow cytometric buffer solution per well, and thereafter 50 μl of a 3.7% formalin solution was added and the resulting solution mixture was allowed to stand for 10 minutes on ice. In this manner, the cells were immobilized. After centrifugation (at 90×g, 4° C. for 10 minutes), the supernatant was removed. The pellet was washed again with 100 μl of the flow cytometric buffer solution per well and suspended in 100 μl of the flow cytometric buffer per well. This was used as a sample for flow cytometry. The intensity of FITC fluorescence emitted from the cells in each sample was measured using a flow cytometer (Epics Elite manufactured by Coulter) at an excitation wavelength of 488 nm and a detection wavelength of 530 nm. When the FITC fluorescence intensity of the human oculospanin expressing cells exposed to supernatant from the fusion cell culture was much higher (about 100 to 1,000) than that (about 0.3) of the human oculospanin expressing cells unexposed to the supernatant from the fusion cell culture, the corresponding fusion cells were selected.

(4-5) Cloning

The cells selected in Section (4-4) above were subjected to a series of steps (4-3) to (4-4), five times. In this way, several hybridoma clones were obtained which were capable of producing a single antibody capable of binding to human oculospanin expressing cells but incapable of binding to the non-transfected parent cells.

EXAMPLE 5

Purification of Human Oculospanin Monoclonal Antibody

Mouse-mouse hybridoma cells constructed in Example 4 were cultured in 1 liter of ASF medium containing 10% FCS at 37° C. in 5% $CO_2$ gas until the cell density reached $1 \times 10^6$ cells/ml. The culture solution was centrifuged (at 1,000 rpm for 2 minutes), the supernatant was discarded, and the cells collected were washed once using serum-free ASF medium. Thereafter, the cells were resuspended in 1 litre of serum-free ASF medium and cultured at 37° C. in 5% $CO_2$ gas for 48 hours. The culture solution was centrifuged (at 1,000 rpm for 2 minutes) and the supernatant was recovered and transferred into a dialysis tube (exclusion limit molecular weight: 12,000 to 14,000, manufactured by Gibco BRL). Dialysis was performed against a 10-fold amount of 10 mM sodium phosphate buffer solution (pH 8.0). The IgG contained in the solution within the dialysis tube was crudely purified using high performance liquid chromatographic apparatus (FPLC system, manufactured by Pharmacia) under the conditions described below:

Column: DEAE Sepharose CL-6B column (Column size 10 ml, manufactured by Pharmacia)
Solvent: 10 mM sodium phosphate buffer solution (pH 8.0)
Flow rate: 1 ml/minute
Elution: 1M sodium chloride linear concentration gradient (0-50%, 180 minutes)

The eluate was fractionated into 5 ml samples. The antibody titer of the anti-human oculospanin antibody in each fraction was checked by the ELISA method using human oculospanin protein. First, a membrane fraction solution prepared from human oculospanin expressing cells prepared in Example 3 was added to a 96-well microplate for ELISA in an amount of 100 μl/well and kept warm at 37° C. for one hour. Then the membrane fraction solution was discarded and each well was washed three times with 100 μl of PBS-Tween per well. Then, 100 μl of PBS containing 2% bovine serum albumin was added per well and kept warm at 37° C. for one hour. After washing three times with 100 μl of PBS-Tween per well, 100 μl of the elution fraction was added and kept warm at 37° C. for one hour. Furthermore, after wells were washed three times with 100 μl of PBS-Tween per well, horseradish peroxidase-labeled anti-mouse immunoglobulin antibody (manufactured by Amersham) diluted 2000 fold in PBS-Tween was added in an amount of 100 μl/well and allowed to react at 37° C. for one hour, and then washed three times with 100 μl of PBS-Tween per well. Subsequently, a substrate for horseradish peroxidase (manufactured by BioRad) was added in an amount of 100 μl/well and allowed to stand still for 5 minutes, and thereafter, the absorbance of each well at 415 nm was measured using a microplate reader.

Consequently, the fractions exhibiting high absorbance were collected and loaded onto two antibody affinity purification columns (Hitrap Protein G column, column volume: 5 ml, manufactured by Pharmacia). After washing the inside of the columns with 25 ml of equilibrium buffer (20 mM, sodium phosphate buffer (pH 7.0) per column, the antibody was eluted using 15 ml of an elution buffer (0.1M glycine-hydrochloride (pH 2.7)) per column. Each eluate was collected in a test tube containing 1.125 ml of 1M Tris-hydrochloride (pH 9.0). Immediately after completion of the elution, the eluate was loaded onto the upper portion of an ultrafilter of centrifugation-tube form (Centriprep 10 manufactured by Grace Japan) and centrifuged at 3000×g at 4° C. for 2 hours. After the filtrate collected in the lower portion of the filter was removed, 15 ml of PBS was added to the upper portion and again centrifuged at 3000×g, and 4° C. for 2 hours. In all, this operation was repeated five times. At the 5th time of operation, the centrifugation operation was performed until the liquid amount in the upper portion of the filter reached 0.5 ml. The liquid left in the upper portion of the filter was used as a sample of the anti-human oculospanin antibody.

EXAMPLE 6

Cytotoxic Activity

Antibody-dependent cytotoxic activity was measured as an index of bioactivity.

The number of human oculospanin expressing cells (Example 3) was counted by the tryphan blue staining method, the concentration of the cells was adjusted to $1 \times 10^6$ cells/ml with RPMI 1640 medium (manufactured by Invitrogen, hereinafter referred to as the "RPMI medium") containing 10% fetal bovine serum (manufactured by Moregate). To the cells, 2.5 µl of bis(acetoxymethyl)2,2':6'2"-terpyridine-6,6"-dicarboxylic acid (BATDA labeling agent, manufactured by PerkinElmer) was added, stirred well and incubated at 37° C. in 5% carbon dioxide for 30 minutes while mixing at intervals of 15 minutes by inverting the culture. To the culture medium, 10 ml of the RPMI medium was added, stirred and centrifuged at 1,500 rpm for 5 minutes. This washing operation was repeated a further two times. The BATDA labeled human oculospanin expressing cells thus obtained were resuspended in 10 ml of RPMI 1640 medium. An aliquot of 50 µl ($5 \times 10^3$ cells) of the suspension solution was seeded in each well of a 96-well round bottom microplate, which was previously prepared by adding a purified mouse anti-human oculospanin antibody previously adjusted with RPMI 1640 medium to a concentration of 1 µg/ml, or the supernatant of the hybridoma culture medium, and leaving it stand still at 4° C. for 30 minutes. The microplate was allowed to stand still at 4° C. for a further 30 minutes. To a negative control well there was added either the purified mouse anti-human oculospanin antibody or RPMI 1640 medium in place of the hybridoma supernatant.

Effector cells were prepared as follows. J774A.1 cells (available from Dainippon Pharmaceutical Co., Ltd.) were cultured in the presence of 100 ng/ml macrophage colony stimulating factor (manufactured by Sigma) for 3 days. The number of J774A.1 cells was counted by the tryphan blue staining method and then adjusted with RPMI medium to a concentration of $1 \times 10^6$ cells/ml. To each well of the 96-well round-bottom microplate mentioned above, an 100 µl aliquot ($1 \times 10^5$ cells) of the cells was seeded. The microplate was centrifuged at 1,500 rpm for 5 minutes and incubated at 37° C. in 5% $CO_2$ gas for 4 hours. To a positive control well, 1% Triton-X-100 was added in place of the effector cells, in order to completely kill the BATDA-labeled human oculospanin expressing cells. After a 4 hour incubation, 20 µl of the culture supernatant was taken from each well and transferred to 96-well white plate. To the plate, 200 µl of a europium solution (manufactured by PerkinElmer) was added. The plate was shaken at room temperature for 15 minutes and the decomposition of fluorescence with time was measured.

The rate of cell death induction in each well was calculated based on the equation below:

Cell death induction rate (%)=(fluorescent count for each test well−background count for the negative control well)/(the fluorescent count for the positive control well−background count for the negative control well)×100.

By comparison with a control containing only RPMI 1640 medium, it was confirmed that cell death of the human oculospanin expressing cells was induced by addition of the purified mouse anti-human oculospanin antibody or the hybridoma supernatant.

EXAMPLE 7

Preparation of Human Oculospanin Expressing Cells and Their Membrane Fraction as Immunogen and Antigen for Detecting Antibody a) Construction of Plasmid pEF/DEST51-NM_031945

The NM_031945 cDNA obtained in Example 2a) was cloned into the pENTR/D-TOPO vector by using the pENTR Directional TOPO cloning kit (manufactured by Invitrogen) in accordance with the protocol provided. The NM_031945 cDNA was mixed with pENTR/D-TOPO vector having Topoisomerase bound thereto, in a reaction buffer provided with the kit and incubated at room temperature for 30 minutes. Using the reaction product obtained, Oneshot TOP10 chemically competent E. coli. (manufactured by Invitrogen) were transformed and cultured in LB agar medium containing 50 µg/ml kanamycin. The resulting E. coli colonies, resistant to kanamycin, were selected and cultured in 1 ml of liquid TB medium containing 50 µg/ml of kanamycin at 37° C. overnight. The plasmid DNA was isolated and purified using a Montage Plasmid Miniprep$_{96}$ Kit (manufactured by Millipore). Next, the plasmid DNA thus obtained was subjected to a sequencing reaction performed using a BigDye Terminator v3.0 Cycle Sequencing Ready Reaction Kit in accordance with the protocol provided, the nucleotide sequence was analyzed using an ABI PRISM 3100 DNA Analyzer (manufactured by Applied Biosystem). As a result, it was confirmed that the cDNA (Sequence ID No. 1 of the sequence listing) having an open reading frame of the nucleotide sequence represented by Accession No. NM_031945 was integrated in the pENTR/D-TOPO vector.

Then, the gene was transferred into expression vector pcDNA3.1/DEST40 (manufactured by Invitrogen) by use of the GATEWAY™ system. More specifically, 4 µl of GATEWAY™ LR Clonase™ Enzyme Mix (manufactured by Invitrogen), 4 µl of LR Reaction Buffer, 0.3 µg of pENTR/D-TOPO-NM_031945, 0.3 µg of pcDNA3.1/DEST40, were mixed with TE buffer to prepare a 20 µl solution, which was allowed to react at 25° C. for one hour. After completion of the reaction, 2 µl of Proteinase K was added and a reaction was performed at 37° C. for 10 minutes. OneShot TOP10 Chemically Competent E. coli (manufactured by Invitrogen) were transfected with the reaction product and cultured on LB agar medium containing 50 µg/ml of ampicillin. The resulting E. coli colonies, resistant to ampicillin, were selected and incubated in 100 ml of liquid LB medium containing 50 μg/ml of ampicillin at 37° C. overnight. As a result, plasmid DNA (pcDNA3.1-DEST40-NM_031945) was isolated and purified using the Plasmid MAXI Kit (manufactured by Qiagen).

Similarly, the gene was transferred to the expression vector pEF/DEST51 (manufactured by Invitrogen) by use of the Gateway™ system. To explain more specifically, 4 μl of GATEWAY™ LR Clonase™ Enzyme Mix (manufactured by Invitrogen), 4 μl of LR Reaction Buffer, 0.3 μg of pENTR/D-TOPO-NM_031945 and 0.3 μg of pEF/DEST51 were mixed with TE buffer to prepare a 20 μl solution and allowed to react at 25° C. for one hour. After the reaction, 2 μl of proteinase K was added and allowed to react at 37° C. for 10 minutes. OneShot TOP10 Chemically Competent *E. coli* (manufactured by Invitrogen) were transformed with the reaction product obtained and cultured on LB agar medium containing 50 μg/ml ampicillin. The resulting *E. coli* colonies, resistant to ampicillin, were selected and cultured in 100 ml of liquid LB medium, containing 50 μg/ml ampicillin, at 37° C. overnight. As a result, plasmid DNA (pEF-DEST51-NM-031945) was isolated and purified using the Plasmid MAXI Kit (manufactured by Qiagen).

b) Transfection of BALB-3T3 Cells and 293T Cells with the Plasmid pEF-DEST51-NM_031945

BALB-3T3 cells (available from RIKEN, clone A31) were cultured in 330 150 mm cell-culture dishes (culturing area: 148 cm², manufactured by IWAKI) containing Dulbecco's Modified Eagle's medium (hereinafter referred to as the "DMEM", manufactured by SIGMA) supplemented with 10% bovine serum (manufactured by GIBCO; hereinafter referred to as "BS") at 37° C. in 5% $CO_2$ gas up to a semi-confluent state. Thereafter, the BALB-3T3 cells were transfected with plasmid pEF-DEST51-NM_031945. The Transfection of BALB-3T3 cells was performed by lipofection using the Geneporter™ 2 transfection reagent manufactured by Gene Therapy Systems. More specifically, the cells were washed once with serum-free medium (DMEM) and 20 ml of the serum-free medium (DMEM) was added. Then, to a 50 ml Falcon tube, 0.6 ml of New DNA diluent and 24 μg of plasmid DNA (pEF-DEST51-NM_031945) recovered by the aforementioned method were added and mixed. To another 50 ml Falcon tube, 0.35 ml of a serum free medium (Opti-MEM I, manufactured by GIBCO) and 84 μl of Geneporter™ 2 Reagent were added and mixed. The DNA solution and the Geneporter™ 2 solution were mixed and allowed to stand still at room temperature for 20 minutes. Thereafter, the solution mixture of DNA-Geneporter™ 2 was added to the cells (1 ml/dish) and cultured at 37° C. in 5% $CO_2$. After 3 hours, the medium was replaced with 20 ml of DMEM containing 10% bovine serum per dish and cultured at 37° C. overnight in 5% $CO_2$.

Furthermore, plasmid pEF-DEST51-NM_031945 was introduced in 293T cells as follows. Introduction into the 293T cells was performed by using LIPOFECTAMINE 2000 reagent (manufactured by Invitrogen). The 293T cells were seeded at a density of $2.5 \times 10^5$ cells/9.2 cm² and cultured at 37° C. overnight in 5% $CO_2$. In a 5 ml polypropylene tube, 10 μl of LIPOFECTAMINE 2000 reagent and 250 μl of OPTI-MEM I Reduced Serum Medium (manufactured by Invitrogen) were mixed and allowed to react with each other at room temperature for 5 minutes. In another 5 ml polyethylene tube, 4 μg of plasmid (pEF-DEST51-NM_031945) and 250 μl of OPTI-MEM I Reduced Serum Medium were mixed. The LIPOFECTAMINE solution and the DNA solution were mixed and allowed to react with each other at room temperature for 20 minutes. The supernatant was removed from the 293T cells cultured overnight and an antibiotic-free Dulbecco's Modified Eagle medium (manufactured by Gibco) containing 10% fetal calf serum (manufactured by Moregate) was added to the cells in an amount of 2 ml/9.2 cm². The LIPOFECTAMINE-DNA solution mixture was added to the 293T cells and incubated at 37° C. in 5% $CO_2$ gas for 2 days.

c) Preparation of the Cell Membrane Fraction (10 Liter)

The cells cultured by the aforementioned method were washed with a PBS (−) buffer solution (manufactured by Dainippon Pharmaceutical Co., Ltd). The cells were collected using a cell scraper (manufactured by IWAKI) and suspended in 230 ml of a 5 mM Tris buffer solution, pH 7.4. The resulting cell solution was allowed to stand still at 4° C. for 30 minutes. The cells were crushed using a Dounce Type B homogenizer (50 strokes) and centrifuged at 1000 G for 10 minutes. The supernatant was recovered and centrifuged at 1,000 G for 10 minutes using an ultracentrifugation apparatus (manufactured by KUBOTA) and the supernatant was recovered.

The supernatant was centrifuged at 78,000 G for 100 minutes using an ultracentrifugation apparatus (manufactured by BECKMAN) and the precipitate was recovered. To the precipitate, 14 ml of 57% sucrose in Tris buffer was superposed and subjected to sugar density gradient at 78,000 G for 16 hours at 4° C. As a result, the membrane fragment of the upper layer was recovered. To the membrane fraction, 55 ml of 5 mM Tris buffer, pH 7.4, was added and centrifuged at 78,000 G for 60 minutes at 4° C. The precipitate was recovered. To the precipitate, 1500 μl of 5 mM Tris buffer, pH 7.4, was added and then the cell solution was homogenized by the Dounce type B homogenizer (10 strokes). The membrane fraction was identified using a Western blotting method described in the Section "Confirmation of expression".

EXAMPLE 8

Immunization of Mouse and Cell Fusion a) Immunization $1 \times 10^7$ cells of the human oculospanin gene expressing cells obtained in Example 7 were injected intraperitoneally into BALB/c female mice which were 5 weeks old (purchased from Japan SLC Inc.) After 2, 4, 6 and 8 weeks, the human oculospanin gene expressing cells ($1 \times 10^7$ cells/mouse) were injected intraperitoneally as a booster in the same manner.

b) Cell Fusion

The spleen was excised out from a mouse on the fourth day after the booster immunization and added to 10 ml of a serum-free MEM medium (9.4 g/L, Eagle MEM medium "Nissui"(1): manufactured by Nissui Pharmaceutical Co., Ltd., hereinafter referred to as "serum-free MEM medium") containing 10 mM HEPES buffer (pH 7.4), 0.02 mg/l sodium hydrogen carbonate, and 300 μg/ml L-glutamic acid, and then the spleen cells were withdrawn using a 21 G' syringe and tweezers. The cell suspension solution was centrifuged to precipitate the spleen cells. The spleen cells were washed twice with the serum-free MEM medium and suspended in serum-free MEM medium and the number of cells was counted.

Myeloma cells SP2/0 were cultured in myeloma growth medium (hereinafter referred to as the "ME medium") containing 15% FBS (manufactured by GIBCO), 306 μg/ml glutamic acid, and 0.05 mM β-mercaptoethanol at 37° C. in the presence of 7% carbon dioxide gas such that the cell density did not exceed 1×10⁶ cells/ml. The myeloma cells SP2/0 thus cultured were washed with the serum-free MEM medium and suspended in serum-free MEM medium and the number of cells was counted.

The SP2/0 cell suspension solution containing cells, the number of which corresponded to about ⅕ of the spleen cells, and the suspension solution for the whole spleen cells were mixed. After centrifugation, the supernatant was completely removed. The cell fusion operation below was performed while keeping a plastic centrifuge tube containing the pellet at room temperature. To the pellet, 1 ml of 40% (w/v) polyethylene glycol 4000 (manufactured by Merck) was slowly added while shaking the centrifuge tube. Thereafter, 9 ml of serum-free MEM medium previously warmed at 37° C. was gently added in three times. After centrifugation, the supernatant was removed and hypoxanthine aminopterin thymidine medium (hereinafter referred to as the "HAT medium"; manufactured by SIGMA) containing 20% FBS was added using a pipette while gently stirring with the pipette tip such that the cell density became 2.5×10⁶ cells/ml. The HAT medium was dispensed to a 96-well cell-culture microplate in an amount of 100 µl/well and cultured at 37° C. in the presence of 7% carbon dioxide gas. After one day, fresh HAT medium was added to all the wells in an amount of 100 µl/well and thereafter, the medium was replaced with fresh medium at intervals of 2 to 3 days. The fused cells thus obtained were subjected to screening by limiting dilution analysis as mentioned below.

c) Limiting Dilution

The culture solution containing the fused cells obtained in Section (b) above was serially diluted such that the density of fused cells in the HT medium (HY medium in the case of 2nd cloning or later) became 1 cell/well (10 cells/ml), and 5 cells/well (50 cells/ml). Each of the samples thus prepared was dispensed in an amount of 100 µl per well, in a 96-well microplate already containing 100 µl of the HY medium, and the microplates were cultured at 37° C. in the presence of 7% carbon dioxide gas for 10 days.

d) Screening d-1) ELISA

The cell membrane fraction obtained in Example 7 was prepared in a solution of 1 µg/ml dispensed into a 96-well EIA plate (manufactured by COSTAR) in an amount of 50 µl/well. After the plate was allowed to stand at 4° C. for one day, the antigen solution within the plate was discarded by shaking well and 80 µl of a solution containing 1% BSA in PBS(−) was added per well. The plate was sealed and stored at 4° C. until use. When used, the plate was returned to room temperature and washed three times using a Serawasher (manufactured by Bio-Tec) through which PBS (PBS-T) containing 0.1% Tween 20 was supplied. As a primary antibody, 50 µl of cell culture supernatant obtained after 10 to 12 days of cell fusion was added to each well and allowed to stand at room temperature for one hour. After completion of the reaction with the primary antibody, the plate was washed three times with PBS-T and alkaline phosphatase labeled anti-mouse IgG antibody (manufactured by BIO SOURCE), diluted 5000 fold with a solution (antigen dilution solution) containing 0.5% BSA added to PBS-T, was added to the wells in an amount of 50 µl/well, and allowed to stand still at room temperature for one hour. After completion of the reaction with the secondary antibody, a color-emitting substrate for alkaline phosphatase, p-nitrophenyl phosphate, 2Na6H₂O (pNPP, manufactured by Wako Pure Chemical Industries Ltd.) returned to room temperature was dissolved to a concentration of 1 mg/ml in pNPP Buffer (97 ml/l diethanolamine, 0.1 g/l MgCl₂.6H₂O, pH 9.8) and added to the wells in an amount of 100 µl/well. The absorbance was measured at 405 nm and 630 nm using a plate reader (manufactured by Nalgene Nunc International)

d-2) Flow Cytometry

HEK293 culture cells obtained in Example 7 were cultured in DMEM medium containing 10% FBS at 37° C. in 5% $CO_2$ gas. After transfection, the cells were cultured for 24 hours and a cell suspension solution was prepared so as to contain 2×10⁷ cells/ml. The cell suspension solution was dispensed into 96-well V-shape bottom microplates (manufactured by Corning) in an amount of 50 µl/well and subjected to centrifugation (1000×g, 20° C. for 5 minutes). The supernatant was removed and the supernatant of the fused cells cultured in step (c) above was added at an amount of 50 µl/well, stirred, allowed to stand still on ice for 0.75 hours, centrifuged (1000×g, 20° C. for 5 minutes), and then the supernatant was removed. The pellet was washed twice with a flow cytometry buffer solution (MEM containing 5% FBS) in an amount of 150 µl/well. Thereafter, to the pellet, 100 µl of 33-fold diluted rabbit anti-mouse IgG antibody (manufactured by Wako Pure Chemical Industries Ltd.) labeled with fluorescein-5-isothiocyanate (hereinafter referred to as "FITC") was added as a secondary antibody, allowed to stand still on ice for 0.75 hours, and subjected to centrifugation (1000×g, 20° C. for 5 minutes). The supernatant was removed, the pellet was washed twice with flow cytometry buffer using 150 µl/well and suspended in the flow cytometry buffer in an amount of 500 µl/well. This was used as a sample for flow cytometry. In each sample, the intensity of FITC fluorescence emitted from cells was measured by flow cytometry (FC500, manufactured by BECKMAN) at an excitation wavelength of 488 nm and a detection wavelength of 530 nm. As a result, the fused cells were selected from the sample exhibiting higher FITC fluorescent intensity than those of HEK293 transient expressing cells to which the supernatant of the fusion cell culture was not added.

e) Cloning

The cells selected in the step (d) above were subjected twice to the operations of a series of steps c) to d). As a result, several hybridoma clones were obtained which produced a monoclonal antibody which binds to HEK293 transient expressing cells, but does not bind to cells into which the anti-human oculospanin expression plasmid has not been introduced. One of the hybridoma strains thus cloned was designated as O3B8-2C9-4F3 and deposited at the International Patent Organism Depositary of the National Institute of Advanced Industrial Science Technology as of Feb. 17, 2004 under deposition No. FERM BP-08627.

EXAMPLE 9

Purification of Anti-Human Oculospanin Monoclonal Antibody

The mouse-mouse hybridoma prepared in Example 8 was suspended in HY medium at a concentration of 1×10⁶ cells/ml and allowed to stand still at 37° C. in the presence of 7% carbon dioxide for 3 days. The culture solution thus obtained was centrifuged at 1,600 rpm for 5 minutes. The supernatant was recovered and IgG was roughly purified as follows:

Binding buffer: pH 7.0 (20 mM $Na_2HPO_4.12H_2O$, 20 mM $Na_2HPO_4.2H_2O$)
Elution buffer: pH 3.0, 100 mM glycine-HCl
Neutralization buffer: pH 9.0, 1M Tris-HCl A requisite aliquot of Protein G carrier (manufactured by Amersham Biosciences) was taken. After ethanol was removed, the protein G carrier aliquot was washed twice with ultra pure water and washed once with the binding buffer. The binding buffer was added to the protein G aliquot carrier to make a 50% gel slurry. The protein G gel slurry was added to the supernatant of the hybridoma. The resulting mixture was rotated at 4° C. for 24 hours and washed three times with the binding buffer. After washing, the elution buffer was added to allow antibody to elute. The eluate was received by a tube containing neutralization buffer in an amount of 1/10 of the elution buffer. The eluate was loaded onto the upper portion of an ultrafilter of a sample tube (Amicon Ultrafree-MC: manufactured by Millipore) and centrifuged at 5000×g, 4° C. for 20 minutes. While the filtrate collected in the lower portion of the filter was removed, the eluate was added such that the liquid amount in the upper portion of the filter was at least 50 µl. After the whole amount of eluate was added, PBS (−) was added in the volume 3 times as large as the eluate. In this manner, buffer exchange was performed. The liquid left in the upper portion of the filter was treated as the anti-human oculospanin antibody sample.

EXAMPLE 10

Cytotoxic Activity

As an index of biological activity, antibody-dependent cytotoxic activity was measured. The number of the human oculospanin expressing cells prepared in Example 7 was counted by the tryphan blue staining method and thereafter the concentration of the cells was adjusted with RPMI 1640 medium (manufactured by Invitrogen, hereinafter referred to as "RPMI medium") containing 10% fetal bovine serum (manufactured by Moregate) to $8 \times 10^5$ cells/0.4 ml. Then 40 µl of Chromium-51 (sodium chromate manufactured by Amersham Bioscience) was added to the cells, the cells were incubated at 37° C. in 5% $CO_2$ for 2 hours. To the cells, 8 ml of RPMI medium was added, stirred and then centrifuged at 1,500 rpm for 5 minutes. This washing operation was repeated further twice. The Chromium-51 labeled human oculospanin expressing cells thus obtained were resuspended in 4 ml of RPMI medium and seeded in a 96-well round bottom plate, in which 50 µl of 5 µl/ml purified mouse anti-human oculospanin antibody adjusted with RPMI medium was already present, in an amount of 50 µl ($1 \times 10^4$ cells) per well and allowed to stand still at 4° C. for 30 minutes. In a negative control well or background measurement well, RPMI medium was added in place of the purified mouse anti-human oculospanin antibody.

Effector cells were prepared as mentioned below. The spleen cells were taken from BALB/c-nu/nu mouse (female, 7 weeks old) in accordance with the customary method. Then, the cell number was counted by the tryphan blue staining method, the concentration of the cells was adjusted with RPMI medium to $1.5 \times 10^7$ cells/ml. The cells were seeded into 96-well round bottom microplates in an amount of 100 µl ($1.5 \times 10^6$ cells/ml) per well, centrifuged at 1,500 rpm for 5 minutes and incubated at 37° C. in 5% $CO_2$ for 4 hours. To the positive control well, 2% Triton-X-100 was added in place of the effector cells in order to completely kill the Chromium-51 labeled human oculospanin expressing cells. To the background measurement well, the RPMI medium was added in place of the effector cells. Next, incubation was performed for 4 hours, 50 µl of the culture supernatant was taken from each of the wells and transferred to a 96-well Luma Plate (manufactured by PerkinElmer). The plate was dehydrated at 50° C. overnight, the amount of Chromium-51 in each well was measured by a microplate scintillation counter (TopCourt NTX, manufactured by PerkinElmer).

The rate at which cell death was induced in each well was calculated in accordance with the following formula:

Cell death induction rate (%)=(radioactivity count for each test well−background count for the negative control well)/(the radioactivity count for the positive control well−background count for the negative control well)×100.

Figure 5:
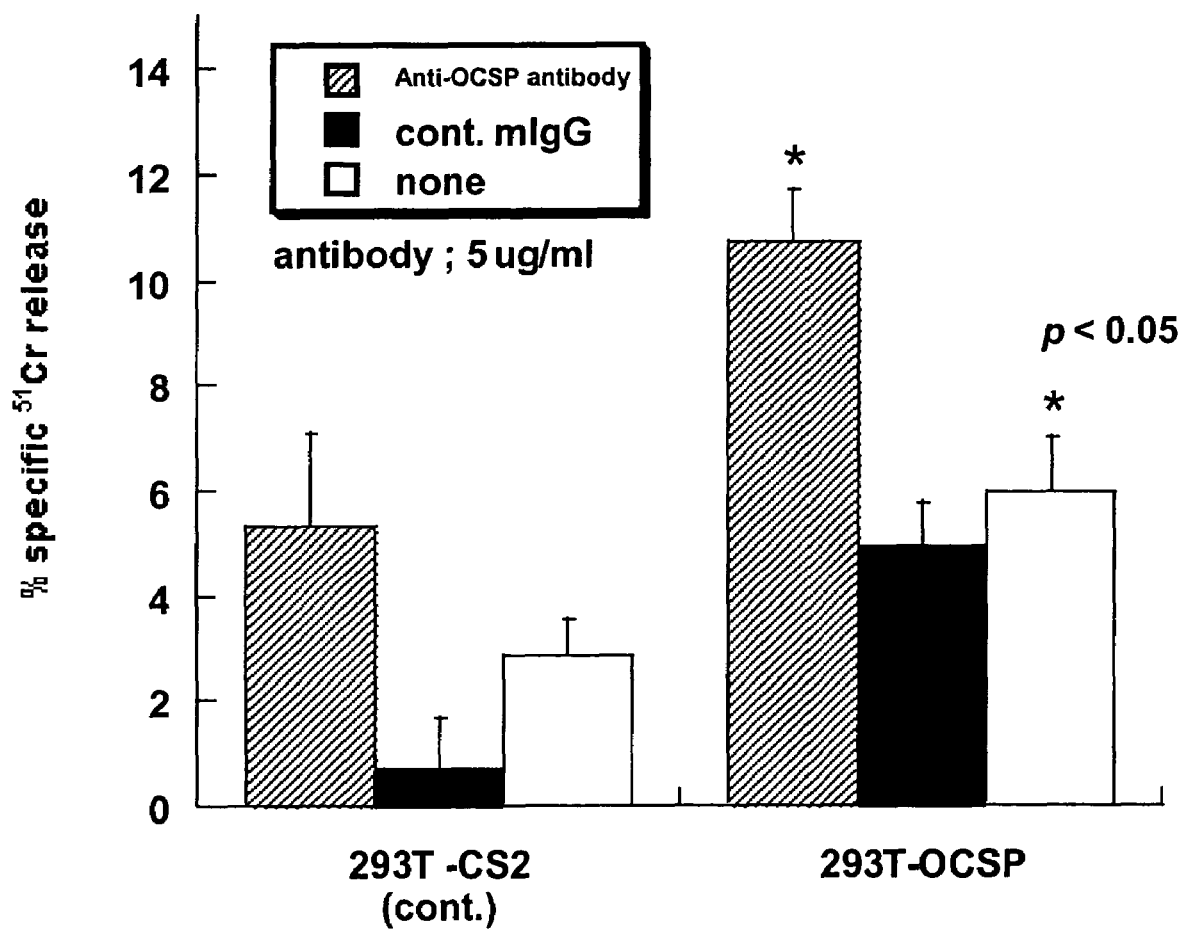
FIG. 5 is a graph showing antibody-dependent cytotoxic activity of an anti-human oculospanin antibody in a human oculospanin-expressing cell.

Compared to the negative control, it was confirmed that addition of the purified mouse anti-human oculospanin antibody (FIG. 5) induced cell death in the human oculospanin expressing cells.

INDUSTRIAL APPLICABILITY

By virtue of the present invention, it was found that the expression level of human oculospanin in melanoma is significantly high. According to the present invention, there are provided a method of detecting cancer using the human oculospanin gene and a cancer detection kit, and further provided an antibody having cytotoxic activity against oculospanin and a pharmaceutical composition for treating cancer containing the antibody.

Sequence List Free Text

Sequence ID No. 5; PCR sense primer for human oculospanin amplification.

The invention claimed is:

1. An antibody for treating cells expressing a human oculospanin protein, the antibody, characterized in that said antibody is produced by mouse hybridoma O3B8-2C9-4F3 (FERM BP-08627).

2. A pharmaceutical composition for treating cells expressing a human oculospanin protein, the composition comprising an antibody according to claim 1 and a pharmaceutically acceptable carrier.

* * * * *

UNITED STATES PATENT AND TRADEMARK OFFICE
CERTIFICATE OF CORRECTION

PATENT NO. : 7,361,340 B2  
APPLICATION NO. : 11/223812  
DATED : April 22, 2008  
INVENTOR(S) : Kimihisa Ichikawa et al.

Page 1 of 1

It is certified that error appears in the above-identified patent and that said Letters Patent is hereby corrected as shown below:

On the Title Page, Item (75)

Name of first inventor <u>reads</u>: "Kimihasa Ichikawa"  
<u>Should read</u>: -- Kimihisa Ichikawa --

| <u>Column</u> | <u>Line</u> | <u>Reads</u> | <u>Should Read</u> |
|---|---|---|---|
| 29 | 25 | "from,the donor" | -- from the donor -- |
| 43 | 45 | "inyeloma cells" | -- myeloma cells -- |

Signed and Sealed this

Sixteenth Day of September, 2008

JON W. DUDAS  
*Director of the United States Patent and Trademark Office*